(12) United States Patent
Wilson et al.

(10) Patent No.: US 6,174,527 B1
(45) Date of Patent: *Jan. 16, 2001

(54) METHODS AND COMPOSITIONS FOR GENE THERAPY FOR THE TREATMENT OF DEFECTS IN LIPOPROTEIN METABOLISM

(75) Inventors: James M. Wilson, Gladwyne; Karen Kozarsky, Philadelphia; Jerome Strauss, III, Wyndmoor, all of PA (US)

(73) Assignee: The Trustees of the University of Pennsylvania, Philadelphia, PA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/894,489

(22) PCT Filed: Feb. 23, 1996

(86) PCT No.: PCT/US96/03041

§ 371 Date: Oct. 24, 1997

§ 102(e) Date: Oct. 24, 1997

(87) PCT Pub. No.: WO96/26286

PCT Pub. Date: Aug. 29, 1996

Related U.S. Application Data

(63) Continuation-in-part of application No. 08/393,734, filed on Feb. 24, 1995, now Pat. No. 5,652,224.

(51) Int. Cl.[7] ............................ A61K 48/00; C12N 15/12; C12N 15/86; C12N 15/864
(52) U.S. Cl. ............................ 424/93.2; 424/93.1; 514/44; 435/320.1; 435/455; 435/456
(58) Field of Search ............................ 435/320.1, 69.1, 435/70.1, 455, 456, 457, 325, 370; 424/93.1, 93.2; 514/44

(56) References Cited

U.S. PATENT DOCUMENTS

| | | | |
|---|---|---|---|
| 4,658,019 | 4/1987 | Kung et al. | 530/388.75 |
| 5,017,691 | 5/1991 | Lee et al. | 530/351 |
| 5,139,941 | * 8/1992 | Muzyczka et al. | 435/456 |
| 5,166,320 | 11/1992 | Wu et al. | 530/395 |
| 5,240,846 | 8/1993 | Collins et al. | 435/371 |
| 5,580,776 | * 12/1996 | Wilson et al. | 435/456 |
| 5,652,224 | 7/1997 | Wilson et al. | 514/44 |
| 5,798,209 | * 8/1998 | Chan | 435/6 |
| 5,856,152 | * 1/1999 | Wilson et al. | 435/457 |
| 5,872,154 | * 2/1999 | Wilson et al. | 514/885 |

FOREIGN PATENT DOCUMENTS

| | | |
|---|---|---|
| 501233 | 9/1992 | (EP). |
| 555880 | 8/1993 | (EP). |
| WO90/05147 | 5/1990 | (WO). |
| WO91/18088 | 11/1991 | (WO). |
| WO93/00431 | 1/1993 | (WO). |
| WO94/12649 | 6/1994 | (WO). |
| WO94/17832 | 8/1994 | (WO). |
| WO95/06743 | 3/1995 | (WO). |
| WO95/13374 | 5/1995 | (WO). |

OTHER PUBLICATIONS

Orkin et al., "Report and recommendations of the panel to assess the NIH investment in research on gene therapy", issued by the U.S. National Institutes of Health, Dec. 1995.*

Levrero et al., "Defective and nondefective adenovirus vectors for expressing foreign genes in vitro and in vivo", Gene 101: 195–202, 1991.*

J. Wilson, "Cystic Fibrosis—Vehicles for Gene Therapy", Nature, 365:691–692 (Oct. 21, 1993) [Wilson I].

J. Wilson et al, "Correction of the Genetic Defect in Hepatocytes from the Watanabe Heritable Hyperlipidemic Rabbit", Proc. Natl. Acad. Sci. USA, 85:4421–4425 (Jun., 1988) [Wilson II].

J. Wilson et al, "Research Article—Transplantation of Allogeneic Hepatocytes into LDL Receptor Deficient Rabbits Leads to Transient Improvement in Hypercholesterolemia", Clin. Bio., 3:21–26 (Spring, 1991) [Wilson III].

J. Wilson et al, "A Novel Mechanism for Achieving Transgene Persistence in vivo after Somatic Gene Transfer into Hepatocytes", J. Biol. Chem., 267(16):11483–11489 (Jun. 5, 1992) [Wilson IV].

K. Kozarsky et al, "In Vivo Correction of Low Density Lipoprotein Receptor Deficiency in the Watanabe Heritable Hyperlipidemic Rabbit with Recombinant Adenoviruses", J. Biol. Chem., 269(18):13695–13702 (May 6, 1994) [Kozarsky I].

K. Kozarsky et al, "Adenovirus–Mediated Correction of the Genetic Defect in Hepatocytes from Patients with Familial Hypercholesterolemia", Somatic Cell and Molecular Genetics, 19(5):449–458 (Sep., 1993) [Kozarsky II].

K. Kozarsky et al, "Gene Therapy: Adenovirus Vectors", Curr. Opin. Genet. Devel., 3:499–503 (Mar., 1993) [Kozarsky III].

Y. Yang et al, "MHC Class I–Restricted Cytotoxic T Lymphocytes to Viral Antigens Destroy Hepatocytes in Mice Infected with E1–Deleted Recombinant Adenoviruses", Immunity, 1:433–442 (Aug., 1994) [Yang I].

Y. Yang et al, "Cellular Immunity to Viral Antigens Limits E1–Deleted Adenoviruses for Gene Therapy", Proc. Natl. Acad. Sci. USA, 91:4407–4411 (May, 1994) [Yang II].

(List continued on next page.)

Primary Examiner—Scott D. Priebe
(74) Attorney, Agent, or Firm—Howson and Howson

(57) ABSTRACT

The invention provides a recombinant viral vector comprising a human VLDL receptor gene operatively linked to regulatory sequences directing its expression. The vector is capable of expressing the normal VLDL receptor gene product in hepatic cells in vivo or in vitro. This viral vector is useful in the treatment of metabolic disorders caused by the accumulation of LDL in plasma, such as familial hypercholesterolemia or familial combined hyperlipidemia.

4 Claims, 26 Drawing Sheets

OTHER PUBLICATIONS

Y. Yang et al, "Inactivation of E2a in Recombinant Adenoviruses Improves the Prospect for Gene Therapy in Cystic Fibrosis", *Nature Genetics*, 7:362–369 (Jul., 1994) [Yang III].

J. Goldstein et al, "Familial Hypercholesterolemia", in *The Metabolic Basis of Inherited Disease*, Chapter 48, 6th ed., C.R. Scrivers et al (eds), McGraw–Hill Information Services Co., New York, pp. 1215–1250 (1989) [Goldstein I].

J. Goldstein et al, "Defective Lipoprotein Receptors and Atherosclerosis—Lessons from an Animal Counterpart of Familial Hypercholesterolemia", *New Engl. J. Med.*, 309(5):288–296 (Aug. 4, 1983) [Goldstein II].

J. Goldstein et al, "Disorders of the Biogenesis and Secretion of Lipoproteins", in *The Metabolic Basis of Inherited Disease*, Chapter 44B, 6th ed., C.R. Scrivers et al (eds), McGraw–Hill Information Services Co., New York, pp. 1155–1156 (1989) [Goldstein III].

S. Ishibashi et al, "Hypercholesterolemia in Low Density Lipoprotein Receptor Knockout Mice and its Reversal by Adenovirus–Mediated Gene Delivery", *J. Clin. Invest.*, 92:883–893 (Aug., 1993) [Ishibashi I].

S. Ishibashi et al, "Massive Xanthomatosis and Atherosclerosis in Cholesterol–fed Low Density Lipoprotein Receptor–negative Mice", *J. Clin. Invest.*, 93:1885–1893 (May, 1994) [Ishibashi II].

M. Gafvels et al, "Cloning of a cDNA Encoding a Putative Human Very Low Density Lipoprotein/Apolipoprotein E Receptor and Assignment of the Gene to Chromosome 9pter–p266", *Somatic Cell and Molecular Genetics*, 19(6):557–569 (Sep., 1993) [Gafvels].

M. Gafvels et al, "Cloning of a Complementary Deoxyribonucleic Acid Encoding the Murine Homolog of the Very Low Density Lipoprotein/Apolipoprotein–E Receptor: Expression Pattern and Assignment of the Gene to Mouse Chromosome 19", *Endocrinology*, 135(1):387–394 (Jul., 1994) [Gafvels II].

S. Takahashi et al, "Rabbit Very Low Density Lipoprotein Receptor: A Low Density Lipoprotein Receptor–Like Protein with Distinct Ligand Specificity", *Proc. Natl. Acad. Sci. USA*, 89:9252–9256 (Oct., 1992).

J. Engelhardt et al, "Ablation of E2A in Recombinant Adenoviruses Improves Transgene Persistence and Decreases Inflammatory Response in Mouse Liver", *Proc. Natl. Acad. Sci. USA*, 91:6196–6200 (Jun., 1994) [Engelhardt I].

J. Engelhardt et al, "Adenovirus–Mediated Transfer of the CFTR Gene to Lung of Nonhuman Primates: Biological Efficacy Study", *Human Genet. Ther.*, 4:759–769 (Dec., 1993) [Engelhardt II].

J. Engelhardt et al, "Prolonged Transgene Expression in Cotton Rat Lung with Recombinant Adenoviruses Defective in E2a", *Human Gene Ther.*, 5:1217–1229 (Oct., 1994) [Engelhardt III].

Y. Watanabe, "Serial Inbreeding of Rabbits with Hereditary Hyperlipidemia (WHHL–Rabbit)", *Atherosclerosis*, 36:261–268 (1980).

K. Tanzawa et al, "WHHL–Rabbit: A Low Density Lipoprotein Receptor–Deficient Animal Model for Familial Hypercholesterolemia", *FEBS Letters*, 118(1):81–84 (Aug., 1980).

M Horwitz, "Adenoviridae and Their Replication", *Virology*, 2d edition, ed. B. N. Fields, Raven Press, Ltd., New York, Chapter 60, pp. 1679–1721 (1990).

M. Grossman et al, "Towards Liver–Directed Gene Therapy: Retrovirus–Mediated Gene Transfer into Human Hepatocytes", *Som. Cell. and Mol. Gen.*, 17(6):601–607 (Nov., 1991).

M. Boshart et al, "A Very Strong Enhancer is Located Upstream of an Immediate Early Gene of Human Cytomegalovirus", *Cell*, 41:521–530 (Jun., 1985).

C. Wu et al, "Targeting Genes: Delivery and Persistent Expression of a Foreign Gene Driven by Mammalian Regulatory Elements in vivo", *J. Biol. Chem.*, 264(29):16985–16987 (Oct. 15, 1989).

K. Fisher et al, "Biochemical and Functional Analysis of an Adenovirus–Based Ligand Complex for Gene Transfer", *Biochem. J.*, 299:49–58 (Apr. 1, 1994).

C. Laughlin et al, "Cloning of Infectious Adeno–associated Virus Genomes in Bacterial Plasmids", *Gene*, 23:65–73 (Jul., 1983).

J. Price et al, "Lineage Analysis in the Vertebrate Nervous System by Retrovirus–mediated Gene Transfer", *Proc. Natl. Acad. Sci. USA*, 84:156–160 (Jan., 1987).

T. Kost et al, "The Nucleotide Sequence of the Chick Cytoplasmid beta–actin Gene", *Nucl. Acids Res.*, 11(23):8287–8301 (Dec. 11, 1983).

J. Schreiber et al, "Recombinant Retroviruses Containing Novel Reporter Genes", *BioTechniques*, 14(5):818–823 (May, 1993).

J. Riordan et al, "Identification of the Cystic Fibrosis Gene: Cloning and Characterization of Complementary DNA", *Science*, 245:1066–1073 (Sep. 8, 1989).

M. Brown et al, "A Receptor–Mediated Pathway for Cholesterol Homeostasis", *Science*, 232:34–46 (Apr. 4, 1986).

T. Yamamoto et al, "The Human LDL Receptor: A Cysteine–Rich Protein with Multiple Alu Sequences in its mRNA", *Cell*, 39:27–38 (Nov., 1984).

R. Samulski et al, "Helper–Free Stocks of Recombinant Adeno–Associated Viruses: Normal Integration does not Require Viral Gene Expression", *J. Virol.*, 63(9):3822–3828 (Sep., 1989).

T. Shenk et al, "Genetic Analysis of Adenoviruses", *Current Topics in Microbiol. and Immunol.*, 111:1–39 (1984).

P. Hearing et al, "Identification of a Repeated Sequence Element Required for Efficient Encapsidation of the Adenovirus Type 5 Chromosome", *J. Virol.*, 61(8):2555–2558 (Aug., 1987).

M. Grable et al, "Adenovirus Type 5 Packaging Domain is Composed of a Repeated Element that is Functionally Redundant", *J. Virol.*, 64(5):2047–2056 (May, 1990) [Grable I].

M. Grable et al, "cis and trans Requirements for the Selective Packaging of Adenovirus Type 5 DNA", *J. Virol.*, 66(2):723–731 (Feb., 1992) [Grable II].

F. Wittmaack et al, "Localization and Regulation of the Human Very Low Density Lipoprotein/Apolipoprotein–E Receptor: Trophoblast Expression Predicts a Role for the Receptor in Placental Lipid Transport", *Endocrinol.*, 136(1):340–348 (Jan., 1995).

M. Rosenfeld et al, "In Vivo Transfer of the Human Cystic Fibrosis Transmembrane Conductance Regulator Gene to the Airway Epithelium", *Cell*, 68:143–155 (Jan. 10, 1992).

J. Logan et al, "Adenovirus Tripartite Leader Sequence Enhances Translation of mRNAs Late After Infection", *Proc. Natl. Acad. Sci. USA*, 81:3655–3659 (Jun., 1984).

P. Van Der Vliet et al, "Thermolabile DNA Binding Proteins from Cells Infected with a Temperature–Sensitive Mutant of Adenovirus Defective in Viral DNA Synthesis", *J. Virol.*, 15(2):348–354 (Feb., 1975).

P. Scott, "IL–12: Initiation Cytokine for Cell–Mediated Immunity", *Science*, 260:496–497 (Apr., 1993).

R. Manetti et al, "Natural Killer Cell Stimulatory Factor (Interleukin 12 [IL–12]) Induces T Helper Type 1 (Th1)—specific Immune Responses and Inhibits the Development of IL–4–Producing Th Cells", *J. Exp. Med.*, 177:1199–1204 (Apr., 1993).

A. D'Andrea et al, "Production of Natural Killer Cell Stimulatory Factor (Interleukin 12) by Peripheral Blood Mononuclear Cells", *J. Exp. Med.*, 176:1387–1398 (Nov., 1992).

S. Morris et al, "Effects of IL–12 on in Vivo Cytokine Gene Expression and Ig Isotype Selection", *J. Immunol.*, 152:1047–1056 (Feb., 1994).

F. Heinzel et al, "Recombinant Interleukin 12 Cures Mice Infected with Leishmania major", *J. Exp. Med.*, 177:1505–1509 (May, 1993).

T. Yokota et al, "Isolation and Characterization of a Human Interleukin cDNA Clone, Homologous to Mouse B–Cell Stimulatory Factor 1, that Expresses B–cell– and T–cell–Stimulating Activities", *Proc. Natl. Acad. Sci. USA*, 83:5894–5898 (Aug., 1986).

F. Durie et al, "The Role of CD40 in the Regulation of Humoral and Cell–Mediated Immunity", *Immunol. Today*, 15(9):406–410 (Sep., 1994).

J. Cohen, "Naked DNA Points Way to Vaccines", *Science*, 259:1691–1692 (Mar. 19, 1993).

K. Kozarsky et al, "Effective Treatment of Familial Hypercholesterolaemia in the Mouse Model Using Adenovirus–Mediated Transfer of the VLDL Receptor Gene", *Nature Genetics*, 13:54–62 (May, 1996).

P. Frykman et al, "Normal Plasma Lipoproteins and Fertility in Gene–Targeted Mice Homozygous for a Distruption in the Gene Encoding Very Low Density Lipoprotein Receptor", *Proc. Natl. Acad. Sci. USA,* 92:8453–8457 (Aug., 1995).

J. Webb et al, "Characterization and Tissue–Specific Expression of the Human 'Very Low Dernsity Lipoprotein (VLDL) Receptor' mRNA", *Human Molecular Genetics,* 3(4):531–537 (Apr., 1994).

* cited by examiner

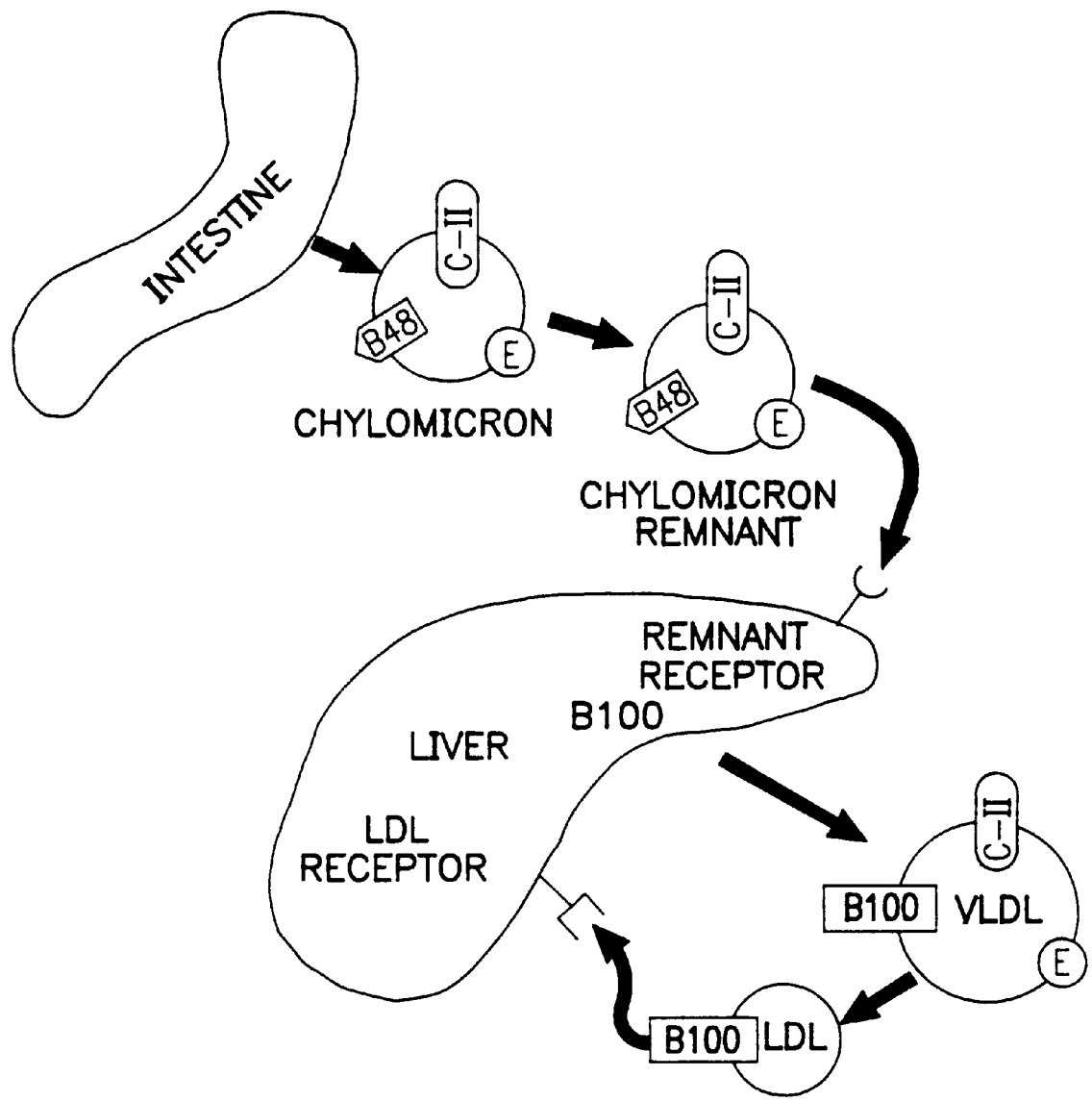
FIG. IA

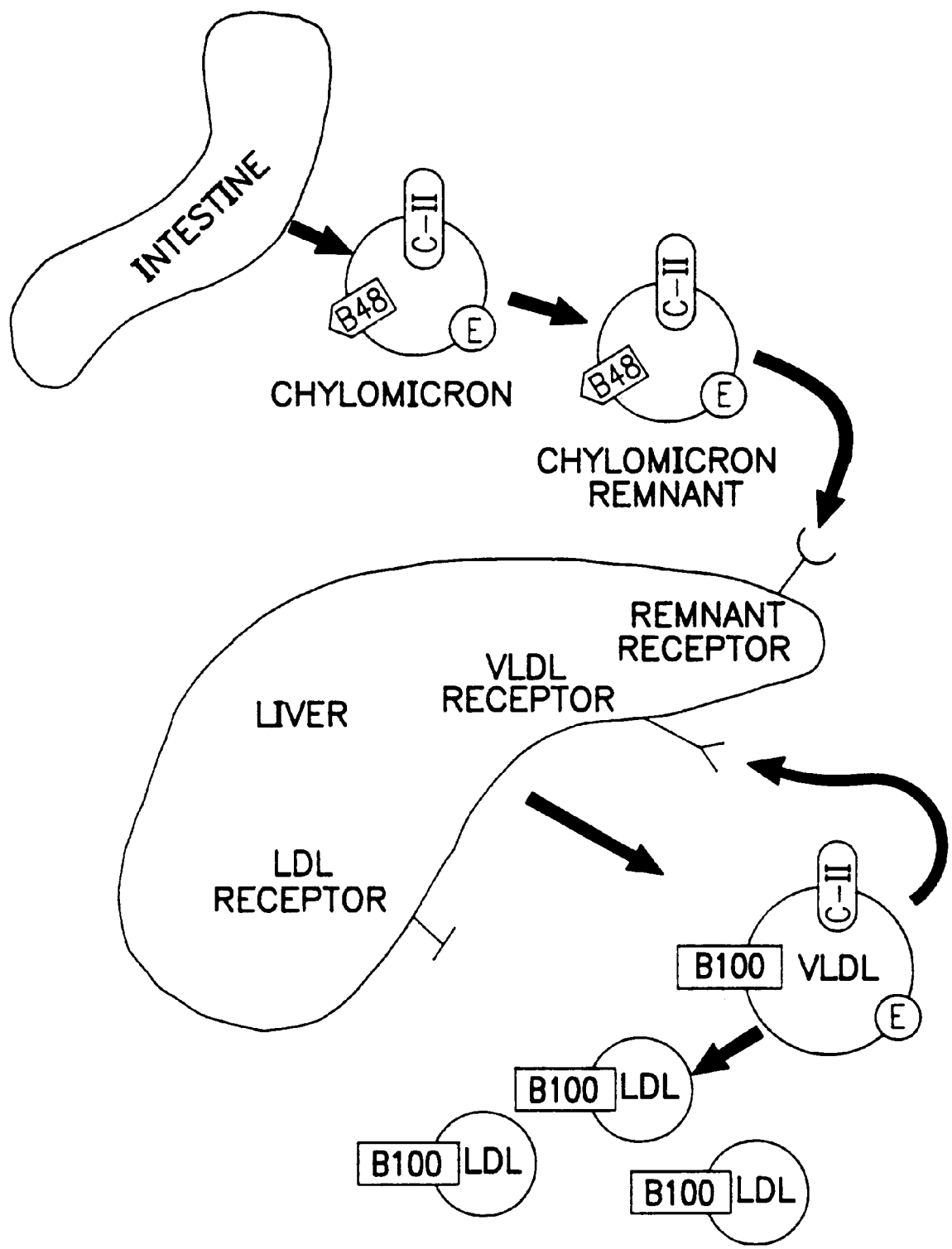
FIG. IC

FIGURE 8A

| | | | | | |
|---|---|---|---|---|---|
| CTCTGCGGGC | CGCGGGTGCG | GGTCGTCGCT | ACCGGCTCTC | TCCGTTCTGT | 50 |
| GCTCTCTTCT | GCTCTCGGCT | CCCCACCCCC | TCTCCCTTCC | CTCCTCTCCC | 100 |
| CTTGCCTCCC | CTCCTCTGCA | GCGCCTGCAT | TATTTTCTGC | CCGCAGCTCG | 150 |
| GCTTGCACTG | CTGCTGCAGC | CCGGGGAGGT | GGCTGGGTGG | GTGGGGAGGA | 200 |
| GACTGTGCAA | GTTGTAGGGG | AGGGGGTGCC | CTCTTCTTCC | CCGCTCCCTT | 250 |
| CCCCAGCCAA | GTGGTTCCCC | TCCTTCTCCC | CCTTTCCCCT | CCCAGCCCCC | 300 |
| ACCTTCTTCC | TCTTTCGGAA | GGGCTGGTAA | CTTGTCGTGC | GGAGCGAACG | 350 |
| GCGGCGGCGG | CGGCGGCGGC | GGCACCATCC | AGGCGGGCAC | C ATG GGC ACG | 400 |
| | | | | Met Gly Thr | |
| | | | | 1 | |

```
TCC GCG CTC TGG GCC GTC TGG CTG CTG CTC GCG CTG TGC TGG        442
Ser Ala Leu Trp Ala Val Trp Leu Leu Leu Ala Leu Cys Trp
        5              10                  15

GCG CCC CGG GAG AGC GGC GCC ACC GGA ACC GGG AGA AAA GCC        484
Ala Pro Arg Glu Ser Gly Ala Thr Gly Thr Gly Arg Lys Ala
        20                  25                  30

AAA TGT GAA CCC TCC CAA TTC CAG TGC ACA AAT GGT CGC TGT        526
Lys Cys Glu Pro Ser Gln Phe Gln Cys Thr Asn Gly Arg Cys
            35                  40                  45

ATT ACG CTG TTG TGG AAA TGT GAT GGG GAT GAA GAC TGT GTT        568
Ile Thr Leu Leu Trp Lys Cys Asp Gly Asp Glu Asp Cys Val
                50                  55

GAC GGC AGT GAT GAA AAG AAC TGT GTA AAG AAG ACG TGT GCT        610
Asp Gly Ser Asp Glu Lys Asn Cys Val Lys Lys Thr Cys Ala
60              65                  70

GAA TCT GAC TTC GTG TGC AAC AAT GGC CAG TGT GTT CCC AGC        652
Glu Ser Asp Phe Val Cys Asn Asn Gly Gln Cys Val Pro Ser
        75                  80                  85

CGA TGG AAG TGT GAT GGA GAT CCT GAC TGC GAA GAT GGT TCA        694
Arg Trp Lys Cys Asp Gly Asp Pro Asp Cys Glu Asp Gly Ser
        90                  95                  100

GAT GAA AGC CCA GAA CAG TGC CAT ATG AGA ACA TGC CGC ATA        736
Asp Glu Ser Pro Glu Gln Cys His Met Arg Thr Cys Arg Ile
            105                 110                 115

CAT GAA ATC AGC TGT GGC GCC CAT TCT ACT CAG TGT ATC CCA        778
His Glu Ile Ser Cys Gly Ala His Ser Thr Gln Cys Ile Pro
                120                 125
```

FIGURE 8B

| | | | | | | | | | | | | |
|---|---|---|---|---|---|---|---|---|---|---|---|---|
| GTG | TCC | TGG | AGA | TGT | GAT | GGT | GAA | AAT | GAT | TGT | GAC | AGT GGA | 820 |
| Val | Ser | Trp | Arg | Cys | Asp | Gly | Glu | Asn | Asp | Cys | Asp | Ser Gly |
| 130 | | | | 135 | | | | | 140 | | | |

```
GTG TCC TGG AGA TGT GAT GGT GAA AAT GAT TGT GAC AGT GGA         820
Val Ser Trp Arg Cys Asp Gly Glu Asn Asp Cys Asp Ser Gly
130             135                 140

GAA GAT GAA GAA AAC TGT GGC AAT ATA ACA TGT AGT CCC GAC         862
Glu Asp Glu Glu Asn Cys Gly Asn Ile Thr Cys Ser Pro Asp
        145             150                 155

GAG TTC ACC TGC TCC AGT GGC CGC TGC ATC TCC AGG AAC TTT         904
Glu Phe Thr Cys Ser Ser Gly Arg Cys Ile Ser Arg Asn Phe
            160                 165             170

GTA TGC AAT GGC CAG GAT GAC TGC AGC GAT GGC AGT GAT GAG         946
Val Cys Asn Gly Gln Asp Asp Cys Ser Asp Gly Ser Asp Glu
                175             180             185

CTG GAC TGT GCC CCG CCA ACC TGT GGC GCC CAT GAG TTC CAG         988
Leu Asp Cys Ala Pro Pro Thr Cys Gly Ala His Glu Phe Gln
                190             195

TGC AGC ACC TCC TCC TGC ATC CCC ATC AGC TGG GTA TGC GAC        1030
Cys Ser Thr Ser Ser Cys Ile Pro Ile Ser Trp Val Cys Asp
200                 205                 210

GAT GAT GCA GAC TGC TCC GAC CAA TCT GAT GAG TCC CTG GAG        1072
Asp Asp Ala Asp Cys Ser Asp Gln Ser Asp Glu Ser Leu Glu
        215                 220                 225

CAG TGT GGC CGT CAG CCA GTC ATA CAC ACC AAG TGT CCA GCC        1114
Gln Cys Gly Arg Gln Pro Val Ile His Thr Lys Cys Pro Ala
            230                 235                 240

AGC GAA ATC CAG TGC GGC TCT GGC GAG TGC ATC CAT AAG AAG        1156
Ser Glu Ile Gln Cys Gly Ser Gly Glu Cys Ile His Lys Lys
                245                 250                 255

TGG CGA TGT GAT GGG GAC CCT GAC TGC AAG GAT GGC AGT GAT        1198
Trp Arg Cys Asp Gly Asp Pro Asp Cys Lys Asp Gly Ser Asp
                260                 265

GAG GTC AAC TGT CCC TCT CGA ACT TGC CGA CCT GAC CAA TTT        1240
Glu Val Asn Cys Pro Ser Arg Thr Cys Arg Pro Asp Gln Phe
270                 275                 280

GAA TGT GAG GAT GGC AGC TGC ATC CAT GGC AGC AGG CAG TGT        1282
Glu Cys Glu Asp Gly Ser Cys Ile His Gly Ser Arg Gln Cys
        285                 290                 295

AAT GGT ATC CGA GAC TGT GTC GAT GGT TCC GAT GAA GTC AAC        1324
Asn Gly Ile Arg Asp Cys Val Asp Gly Ser Asp Glu Val Asn
            300                 305                 310
```

FIGURE 8C

```
TGC AAA AAT GTC AAT CAG TGC TTG GGC CCT GGA AAA TTC AAG        1366
Cys Lys Asn Val Asn Gln Cys Leu Gly Pro Gly Lys Phe Lys
            315             320             325

TGC AGA AGT GGA GAA TGC ATA GAT ATC AGC AAA GTA TGT AAC        1408
Cys Arg Ser Gly Glu Cys Ile Asp Ile Ser Lys Val Cys Asn
                330             335

CAG GAG CAG GAC TGC AGG GAC TGG AGT GAT GAG CCC CTG AAA        1450
Gln Glu Gln Asp Cys Arg Asp Trp Ser Asp Glu Pro Leu Lys
340             345             350

GAG TGT CAT ATA AAC GAA TGC TTG GTA AAT AAT GGT GGA TGT        1492
Glu Cys His Ile Asn Glu Cys Leu Val Asn Asn Gly Gly Cys
    355             360             365

TCT CAT ATC TGC AAA GAC CTA GTT ATA GGC TAC GAG TGT GAC        1534
Ser His Ile Cys Lys Asp Leu Val Ile Gly Tyr Glu Cys Asp
        370             375             380

TGT GCA GCT GGG TTT GAA CTG ATA GAT AGG AAA ACC TGT GGA        1576
Cys Ala Ala Gly Phe Glu Leu Ile Asp Arg Lys Thr Cys Gly
            385             390             395

GAT ATT GAT GAA TGC CAA AAT CCA GGA ATC TGC AGT CAA ATT        1618
Asp Ile Asp Glu Cys Gln Asn Pro Gly Ile Cys Ser Gln Ile
                400             405

TGT ATC AAC TTA AAA GGC GGT TAC AAG TGT GAA TGT AGT CGT        1660
Cys Ile Asn Leu Lys Gly Gly Tyr Lys Cys Glu Cys Ser Arg
410             415             420

GCC TAT CAA ATG GAT CTT GCT ACT GGC GTG TGC AAG GCA GTA        1702
Ala Tyr Gln Met Asp Leu Ala Thr Gly Val Cys Lys Ala Val
    425             430             435

GGC AAA GAG CCA AGT CTG ATC TTC ACT AAT CGA AGA GAC ATC        1744
Gly Lys Glu Pro Ser Leu Ile Phe Thr Asn Arg Arg Asp Ile
        440             445             450

AGG AAG ATT GGC TTA GAG AGG AAA GAA TAT ATC CAA CTA GTT        1786
Arg Lys Ile Gly Leu Glu Arg Lys Glu Tyr Ile Gln Leu Val
            455             460             465

GAA CAG CTA AGA AAC ACT GTG GCT CTC GAT GCT GAC ATT GCT        1828
Glu Gln Leu Arg Asn Thr Val Ala Leu Asp Ala Asp Ile Ala
                470             475

GCC CAG AAA CTA TTC TGG GCC GAT CTA AGC CAA AAG GCT ATC        1870
Ala Gln Lys Leu Phe Trp Ala Asp Leu Ser Gln Lys Ala Ile
480             485             490
```

FIGURE 8D

| | | | | | | | | | | | | |
|---|---|---|---|---|---|---|---|---|---|---|---|---|
| TTC | AGT | GCC | TCA | ATT | GAT | GAC | AAG | GTT | GGT | AGA | CAT | GTT | AAA | 1912 |
| Phe | Ser | Ala | Ser | Ile | Asp | Asp | Lys | Val | Gly | Arg | His | Val | Lys |
| | 495 | | | | 500 | | | | | 505 | | |

```
TTC AGT GCC TCA ATT GAT GAC AAG GTT GGT AGA CAT GTT AAA         1912
Phe Ser Ala Ser Ile Asp Asp Lys Val Gly Arg His Val Lys
    495             500                 505

ATG ATC GAC AAT GTC TAT AAT CCT GCA GCC ATT GCT GTT GAT         1954
Met Ile Asp Asn Val Tyr Asn Pro Ala Ala Ile Ala Val Asp
        510                 515                 520

TGG GTG TAC AAG ACC ATC TAC TGG ACT GAT GCG GCT TCT AAG         1996
Trp Val Tyr Lys Thr Ile Tyr Trp Thr Asp Ala Ala Ser Lys
            525                 530                 535

ACT ATT TCA GTA GCT ACC CTA GAT GGA ACC AAG AGG AAG TTC         2038
Thr Ile Ser Val Ala Thr Leu Asp Gly Thr Lys Arg Lys Phe
                540                 545

CTG TTT AAC TCT GAC TTG CGA GAG CCT GCC TCC ATA GCT GTG         2080
Leu Phe Asn Ser Asp Leu Arg Glu Pro Ala Ser Ile Ala Val
550             555                 560

GAC CCA CTG TCT GGC TTT GTT TAC TGG TCA GAC TGG GGT GAA         2122
Asp Pro Leu Ser Gly Phe Val Tyr Trp Ser Asp Trp Gly Glu
    565             570                 575

CCA GCT AAA ATA GAA AAA GCA GGA ATG AAT GGA TTC GAT AGA         2164
Pro Ala Lys Ile Glu Lys Ala Gly Met Asn Gly Phe Asp Arg
        580                 585                 590

CGT CCA CTG GTG ACA GCG GAT ATC CAG TGG CCT AAC GGA ATT         2206
Arg Pro Leu Val Thr Ala Asp Ile Gln Trp Pro Asn Gly Ile
            595                 600                 605

ACA CTT GAC CTT ATA AAA AGT CGC CTC TAT TGG CTT GAT TCT         2248
Thr Leu Asp Leu Ile Lys Ser Arg Leu Tyr Trp Leu Asp Ser
                610                 615

AAG TTG CAC ATG TTA TCC AGC GTG GAC TTG AAT GGC CAA GAT         2290
Lys Leu His Met Leu Ser Ser Val Asp Leu Asn Gly Gln Asp
620             625                 630

CGT AGG ATA GTA CTA AAG TCT CTG GAG TTC CTA GCT CAT CCT         2332
Arg Arg Ile Val Leu Lys Ser Leu Glu Phe Leu Ala His Pro
    635             640                 645

CTT GCA CTA ACA ATA TTT GAG GAT CGT GTC TAC TGG ATA GAT         2374
Leu Ala Leu Thr Ile Phe Glu Asp Arg Val Tyr Trp Ile Asp
        650                 655                 660

GGG GAA AAT GAA GCA GTC TAT GGT GCC AAT AAA TTC ACT GGA         2416
Gly Glu Asn Glu Ala Val Tyr Gly Ala Asn Lys Phe Thr Gly
            665                 670                 675
```

FIGURE 8E

| | | | | | | | | | | | | |
|---|---|---|---|---|---|---|---|---|---|---|---|---|
| TCA | GAG | CAT | GCC | ACT | CTA | GTC | AAC | AAC | CTG | AAT | GAT | GCC | CAA | 2458
| Ser | Glu | His | Ala | Thr | Leu | Val | Asn | Asn | Leu | Asn | Asp | Ala | Gln |
|  |  |  |  | 680 |  |  |  |  | 685 |  |  |  |  |

```
TCA GAG CAT GCC ACT CTA GTC AAC AAC CTG AAT GAT GCC CAA    2458
Ser Glu His Ala Thr Leu Val Asn Asn Leu Asn Asp Ala Gln
                680                 685

GAC ATC ATT GTC TAT CAT GAA CTT GTA CAG CCA TCA GGT AAA    2500
Asp Ile Ile Val Tyr His Glu Leu Val Gln Pro Ser Gly Lys
690             695                 700

AAT TGG TGT GAA GAA GAC ATG GAG AAT GGA GGA TGT GAA TAC    2545
Asn Trp Cys Glu Glu Asp Met Glu Asn Gly Gly Cys Glu Tyr
    705             710                 715

CTA TGC CTG CCA GCA CCA CAG ATT AAT GAT CAC TCT CCA AAA    2584
Leu Cys Leu Pro Ala Pro Gln Ile Asn Asp His Ser Pro Lys
            720             725                 730

TAT ACC TGT TCC TGT CCC AGT GGG TAC AAT GTA GAG GAA AAT    2626
Tyr Thr Cys Ser Cys Pro Ser Gly Tyr Asn Val Glu Glu Asn
                735             740                 745

GGC CGA GAC TGT CAA AGT ACT GCA ACT ACT GTG ACT TAC AGT    2668
Gly Arg Asp Cys Gln Ser Thr Ala Thr Thr Val Thr Tyr Ser
                    750             755

GAG ACA AAA GAT ACG AAC ACA ACA GAA ATT TCA GCA ACT AGT    2710
Glu Thr Lys Asp Thr Asn Thr Thr Glu Ile Ser Ala Thr Ser
760             765                 770

GGA CTA GTT CCT GGA GGG ATC AAT GTG ACC ACA GCA GTA TCA    2752
Gly Leu Val Pro Gly Gly Ile Asn Val Thr Thr Ala Val Ser
    775             780                 785

GAG GTC AGT GTT CCC CCA AAA GGG ACT TCT GCC GCA TGG GCC    2794
Glu Val Ser Val Pro Pro Lys Gly Thr Ser Ala Ala Trp Ala
        790             795                 800

ATT CTT CCT CTC TTG CTC TTA GTG ATG GCA GCA GTA GGT GGC    2836
Ile Leu Pro Leu Leu Leu Leu Val Met Ala Ala Val Gly Gly
            805             810                 815

TAC TTG ATG TGG CGG AAT TGG CAA CAC AAG AAC ATG AAA AGC    2878
Tyr Leu Met Trp Arg Asn Trp Gln His Lys Asn Met Lys Ser
                820             825

ATG AAC TTT GAC AAT CCT GTG TAC TTG AAA ACC ACT GAA GAG    2920
Met Asn Phe Asp Asn Pro Val Tyr Leu Lys Thr Thr Glu Glu
830             835                 840

GAC CTC TCC ATA GAC ATT GGT AGA CAC AGT GCT TCT GTT GGA    2962
Asp Leu Ser Ile Asp Ile Gly Arg His Ser Ala Ser Val Gly
    845             850                 855
```

FIGURE 8F

| | | | | | | | | | | | | |
|---|---|---|---|---|---|---|---|---|---|---|---|---|
| CAC | ACG | TAC | CCA | GCA | ATA | TCA | GTT | GTA | AGC | ACA | GAT GAT GAT | 3004 |
| His | Thr | Tyr | Pro | Ala | Ile | Ser | Val | Val | Ser | Thr | Asp Asp Asp | |
| | | 860 | | | | | 865 | | | | 870 | |

CTA GCT TGACTTCTGT GACAAATGTT GACCTTTGAG GTCTAAACAA    3050
Leu Ala

ATAATACCCC CGTCGGAATG GTAACCGAGC CAGCAGCTGA AGTCTCTTTT    3100

TCTTCCTCTC GGCTGGAAGA ACATCAAGAT ACCTTTGCGT GGATCAAGCT    3150

TGCTGTACTT GACCGTTTTT ATATTACTTT TGTAAATATT CTTGTCCACA    3200

TTCTACTTCA GCTTTGGATG TGGTTACCGA GTATCTGTAA CCCTTGAATT    3250

TCTAGACAGT ATTGCCACCT CTGGCCAAAT ATGCACTTTC CCTAGAAAGC    3300

CATATTCCAG CAGTGAAACT TGTGCTATAG TGTATACCAC CTGTACATAC    3350

ATTGTATAGG CCATCTGTAA ATATCCCAGA GAACAATCAC TATTCTTAAG    3400

CACTTTGAAA ATATTTCTAT GTAAATTATT GTAAACTTTT TCAATGGTTG    3450

GGACAATGGC AATAGGACAA AACGGGTTAC TAAGATGAAA TTGCCAAAAA    3500

AATTTATAAA CTAATTTTGG TACGTATGAA TGATATCTTT GACCTCAATG    3550

GAGGTTTGCA AAGACTGAGT GTTCAAACTA CTGTACATTT TTTTTCAAGT    3600

GCTAAAAAAT TAAACCAAGC AGCTTAAAAA AAAAAAAAAA AAAAAAAAA    3650

AAAAAA    3656

FIGURE 9A

```
GAATTCGCTA GCATCATCAA TAATATACCT TATTTTGGAT TGAAGCCAAT ATGATAATGA
                                                                60
GGGGGTGGAG TTTGTGACGT GGCGCGGGGC GTGGGAACGG GGCGGGTGAC GTAGTAGTGT
                                                               120
GGCGGAAGTG TGATGTTGCA AGTGTGGCGG AACACATGTA AGCGACGGAT GTGGCAAAAG
                                                               180
TGACGTTTTT GGTGTGCGCC GGTGTACACA GGAAGTGACA ATTTTCGCGC GGTTTTAGGC
                                                               240
GGATGTTGTA GTAAATTTGG GCGTAACCGA GTAAGATTTG GCCATTTTCG CGGGAAAACT
                                                               300
GAATAAGAGG AAGTGAAATC TGAATAATTT TGTGTTACTC ATAGCGCGTA ATATTTGTCT
                                                               360
AGGGAGATCA GCCTGCAGGT CGTTACATAA CTTACGGTAA ATGGCCCGCC TGGCTGACCG
                                                               420
CCCAACGACC CCCGCCCATT GACGTCAATA ATGACGTATG TTCCCATAGT AACGCCAATA
                                                               480
GGGACTTTCC ATTGACGTCA ATGGGTGGAG TATTTACGGT AAACTGCCCA CTTGGCAGTA
                                                               540
CATCAAGTGT ATCATATGCC AAGTACGCCC CCTATTGACG TCAATGACGG TAAATGGCCC
                                                               600
GCCTGGCATT ATGCCCAGTA CATGACCTTA TGGGACTTTC CTACTTGGCA GTACATCTAC
                                                               660
GTATTAGTCA TCGCTATTAC CATGGTGATG CGGTTTTGGC AGTACATCAA TGGGCGTGGA
                                                               720
TAGCGGTTTG ACTCACGGGG ATTTCCAAGT CTCCACCCCA TTGACGTCAA TGGGAGTTTG
                                                               780
TTTTGGCACC AAAATCAACG GGACTTTCCA AAATGTCGTA ACAACTCCGC CCCATTGACG
                                                               840
CAAATGGGCG GTAGGCGTGT ACGGTGGGAG GTCTATATAA GCAGAGCTCT CTGGCTAACT
                                                               900
AGAGAACCCA CTGCTTAACT GGCTTATCGA AATTAATACG ACTCACTATA GGGAGACCCA
                                                               960
AGCTTCTCTG CGGGCCGCGG GTGCGGGTCG TCGCTACCGG CTCTCTCCGT TCTGTGCTCT
                                                              1020
CTTCTGCTCT CGGCTCCCCA CCCCCTCTCC CTTCCCTCCT CTCCCCTTGC CTCCCCTCCT
                                                              1080
```

FIGURE 9B

```
CTGCAGCGCC TGCATTATTT TCTGCCCGCA GCTCGGCTTG CACTGCTGCT GCAGCCCGGG
                                                                1140

GAGGTGGCTG GGTGGGTGGG GAGGAGACTG TGCAAGTTGT AGGGGAGGGG GTGCCCTCTT
                                                                1200

CTTCCCCGCT CCCTTCCCCA GCCAAGTGGT TCCCCTCCTT CTCCCCCTTT CCCCTCCCAG
                                                                1260

CCCCCACCTT CTTCCTCTTT CGGAAGGGCT GGTAACTTGT CGTGCGGAGC GAACGGCGGC
                                                                1320

GGCGGCGGCG GCGGCGGCAC CATCCAGGCG GGCACCATGG GCACGTCCGC GCTCTGGGCC
                                                                1380

GTCTGGCTGC TGCTCGCGCT GTGCTGGGCG CCCCGGGAGA GCGGCGCCAC CGGAACCGGG
                                                                1440

AGAAAAGCCA AATGTGAACC CTCCCAATTC CAGTGCACAA ATGGTCGCTG TATTACGCTG
                                                                1500

TTGTGGAAAT GTGATGGGGA TGAAGACTGT GTTGACGGCA GTGATGAAAA GAACTGTGTA
                                                                1560

AAGAAGACGT GTGCTGAATC TGACTTCGTG TGCAACAATG GCCAGTGTGT TCCCAGCCGA
                                                                1620

TGGAAGTGTG ATGGAGATCC TGACTGCGAA GATGGTTCAG ATGAAAGCCC AGAACAGTGC
                                                                1680

CATATGAGAA CATGCCGCAT ACATGAAATC AGCTGTGGCG CCCATTCTAC TCAGTGTATC
                                                                1740

CCAGTGTCCT GGAGATGTGA TGGTGAAAAT GATTGTGACA GTGGAGAAGA TGAAGAAAAC
                                                                1800

TGTGGCAATA TAACATGTAG TCCCGACGAG TTCACCTGCT CCAGTGGCCG CTGCATCTCC
                                                                1860

AGGAACTTTG TATGCAATGG CCAGGATGAC TGCAGCGATG GCAGTGATGA GCTGGACTGT
                                                                1920

GCCCCGCCAA CCTGTGGCGC CCATGAGTTC CAGTGCAGCA CCTCCTCCTG CATCCCCATC
                                                                1980

AGCTGGGTAT GCGACGATGA TGCAGACTGC TCCGACCAAT CTGATGAGTC CCTGGAGCAG
                                                                2040

TGTGGCCGTC AGCCAGTCAT ACACACCAAG TGTCCAGCCA GCGAAATCCA GTGCGGCTCT
                                                                2100

GGCGAGTGCA TCCATAAGAA GTGGCGATGT GATGGGGACC CTGACTGCAA GGATGGCAGT
                                                                2160
```

FIGURE 9C

```
GATGAGGTCA ACTGTCCCTC TCGAACTTGC CGACCTGACC AATTTGAATG TGAGGATGGC
                                                                2220
AGCTGCATCC ATGGCAGCAG GCAGTGTAAT GGTATCCGAG ACTGTGTCGA TGGTTCCGAT
                                                                2280
GAAGTCAACT GCAAAAATGT CAATCAGTGC TTGGGCCCTG GAAAATTCAA GTGCAGAAGT
                                                                2340
GGAGAATGCA TAGATATCAG CAAAGTATGT AACCAGGAGC AGGACTGCAG GGACTGGAGT
                                                                2400
GATGAGCCCC TGAAAGAGTG TCATATAAAC GAATGCTTGG TAAATAATGG TGGATGTTCT
                                                                2460
CATATCTGCA AGACCTAGT TATAGGCTAC GAGTGTGACT GTGCAGCTGG GTTTGAACTG
                                                                2520
ATAGATAGGA AAACCTGTGG AGATATTGAT GAATGCCAAA ATCCAGGAAT CTGCAGTCAA
                                                                2580
ATTTGTATCA ACTTAAAAGG CGGTTACAAG TGTGAATGTA GTCGTGCCTA TCAAATGGAT
                                                                2640
CTTGCTACTG GCGTGTGCAA GGCAGTAGGC AAAGAGCCAA GTCTGATCTT CACTAATCGA
                                                                2700
AGAGACATCA GGAAGATTGG CTTAGAGAGG AAAGAATATA TCCAACTAGT TGAACAGCTA
                                                                2760
AGAAACACTG TGGCTCTCGA TGCTGACATT GCTGCCCAGA AACTATTCTG GGCCGATCTA
                                                                2820
AGCCAAAAGG CTATCTTCAG TGCCTCAATT GATGACAAGG TTGGTAGACA TGTTAAAATG
                                                                2880
ATCGACAATG TCTATAATCC TGCAGCCATT GCTGTTGATT GGGTGTACAA GACCATCTAC
                                                                2940
TGGACTGATG CGGCTTCTAA GACTATTTCA GTAGCTACCC TAGATGGAAC CAAGAGGAAG
                                                                3000
TTCCTGTTTA ACTCTGACTT GCGAGAGCCT GCCTCCATAG CTGTGGACCC ACTGTCTGGC
                                                                3060
TTTGTTTACT GGTCAGACTG GGGTGAACCA GCTAAAATAG AAAAGCAGG AATGAATGGA
                                                                3120
TTCGATAGAC GTCCACTGGT GACAGCGGAT ATCCAGTGGC CTAACGGAAT TACACTTGAC
                                                                3180
CTTATAAAAA GTCGCCTCTA TTGGCTTGAT TCTAAGTTGC ACATGTTATC CAGCGTGGAC
                                                                3240
```

FIGURE 9D

```
TTGAATGGCC AAGATCGTAG GATAGTACTA AAGTCTCTGG AGTTCCTAGC TCATCCTCTT
                                                                3300
GCACTAACAA TATTTGAGGA TCGTGTCTAC TGGATAGATG GGGAAAATGA AGCAGTCTAT
                                                                3360
GGTGCCAATA AATTCACTGG ATCAGAGCAT GCCACTCTAG TCAACAACCT GAATGATGCC
                                                                3420
CAAGACATCA TTGTCTATCA TGAACTTGTA CAGCCATCAG GTAAAAATTG GTGTGAAGAA
                                                                3480
GACATGGAGA ATGGAGGATG TGAATACCTA TGCCTGCCAG CACCACAGAT TAATGATCAC
                                                                3540
TCTCCAAAAT ATACCTGTTC CTGTCCCAGT GGGTACAATG TAGAGGAAAA TGGCCGAGAC
                                                                3600
TGTCAAAGTA CTGCAACTAC TGTGACTTAG AGACAAAAGA TACGAACACA ACAGAAATTT
                                                                3660
CAGCAACTAG TGGACTAGTT CCTGGAGGGA TCAATGTGAC CACAGCAGTA TCAGAGGTCA
                                                                3720
GTGTTCCCCC AAAAGGGACT TCTGCCGCAT GGGCCATTCT TCCTCTCTTG CTCTTAGTGA
                                                                3780
TGGCAGCAGT AGGTGGCTAC TTGATGTGGC GGAATTGGCA ACACAAGAAC ATGAAAAGCA
                                                                3840
TGAACTTTGA CAATCCTGTG TACTTGAAAA CCACTGAAGA GGACCTCTCC ATAGACATTG
                                                                3900
GTAGACACAG TGCTTCTGTT GGACACACGT ACCCAGCAAT ATCAGTTGTA AGCACAGATG
                                                                3960
ATGATCTAGC TTGACTTCTG TGACAAATGT TGACCTTTGA GGTCTAAACA AATAATACCC
                                                                4020
CCGTCGGAAT GGTAACCGAG CCAGCAGCTG AAGTCTCTTT TTCTTCCTCT CGGCTGGAAG
                                                                4080
AACATCAAGA TACCTTTGCG TGGATCAAGC TTGGTACCGA GCTCGGATCC ACTAGTAACG
                                                                4140
GCCGCCAGTG TGCTGGAATT CTGCAGATAT CCATCACACT GGCGGCCGCG GGATCCAGA
                                                                4200
CATGATAAGA TACATTGATG AGTTTGGACA AACCACAACT AGAATGCAGT GAAAAAAATG
                                                                4260
CTTTATTTGT GAAATTTGTG ATGCTATTGC TTTATTTGTA ACCATTATAA GCTGCAATAA
                                                                4320
```

FIGURE 9E

```
ACAAGTTAAC AACAACAATT GCATTCATTT TATGTTTCAG GTTCAGGGGG AGGTGTGGGA
                                                              4380

GGTTTTTTCG GATCCTCTAG AGTCGACCTG CAGGCTGATC TGGAAGGTGC TGAGGTACGA
                                                              4440

TGAGACCCGC ACCAGGTGCA GACCCTGCGA GTGTGGCGGT AAACATATTA GGAACCAGCC
                                                              4500

TGTGATGCTG GATGTGACCG AGGAGCTGAG GCCCGATCAC TTGGTGCTGG CCTGCACCCG
                                                              4560

CGCTGAGTTT GGCTCTAGCG ATGAAGATAC AGATTGAGGT ACTGAAATGT GTGGGCGTGG
                                                              4620

CTTAAGGGTG GGAAAGAATA TATAAGGTGG GGGTCTTATG TAGTTTTGTA TCTGTTTTGC
                                                              4680

AGCAGCCGCC GCCGCCATGA GCACCAACTC GTTTGATGGA AGCATTGTGA GCTCATATTT
                                                              4740

GACAACGCGC ATGCCCCCAT GGGCCGGGGT GCGTCAGAAT GTGATGGGCT CCAGCATTGA
                                                              4800

TGGTCGCCCC GTCCTGCCCG CAAACTCTAC TACCTTGACC TACGAGACCG TGTCTGGAAC
                                                              4860

GCCGTTGGAG ACTGCAGCCT CCGCCGCCGC TTCAGCCGCT GCAGCCACCG CCCGCGGGAT
                                                              4920

TGTGACTGAC TTTGCTTTCC TGAGCCCGCT TGCAAGCAGT GCAGCTTCCC GTTCATCCGC
                                                              4980

CCGCGATGAC AAGTTGACGG CTCTTTTGGC ACAATTGGAT TCTTTGACCC GGGAACTTAA
                                                              5040

TGTCGTTTCT CAGCAGCTGT TGGATCTGCG CCAGCAGGTT TCTGCCCTGA AGGCTTCCTC
                                                              5100

CCCTCCCAAT GCGGTTTAAA ACATAAATAA AAAACCAGAC TCTGTTTGGA TTTGGATCAA
                                                              5160

GCAAGTGTCT TGCTGTCTTT ATTTAGGGGT TTTGCGCGCG CGGTAGGCCC GGGACCAGCG
                                                              5220

GTCTCGGTCG TTGAGGGTCC TGTGTATTTT TTCCAGGACG TGGTAAAGGT GACTCTGGAT
                                                              5280

GTTCAGATAC ATGGGCATAA GCCCGTCTCT GGGGTGGAGG TAGCACCACT GCAGAGCTTC
                                                              5340

ATGCTGCGGG GTGGTGTTGT AGATGATCCA GTCGTAGCAG GAGCGCTGGG CGTGGTGCCT
                                                              5400
```

FIGURE 9F

```
AAAAATGTCT TTCAGTAGCA AGCTGATTGC CAGGGGCAGG CCCTTGGTGT AAGTGTTTAC
                                                                5460
AAAGCGGTTA AGCTGGGATG GGTGCATACG TGGGGATATG AGATGCATCT TGGACTGTAT
                                                                5520
TTTTAGGTTG GCTATGTTCC CAGCCATATC CCTCCGGGGA TTCATGTTGT GCAGAACCAC
                                                                5580
CAGCACAGTG TATCCGGTGC ACTTGGGAAA TTTGTCATGT AGCTTAGAAG GAAATGCGTG
                                                                5640
GAAGAACTTG GAGACGCCCT TGTGACCTCC AAGATTTTCC ATGCATTCGT CCATAATGAT
                                                                5700
GGCAATGGGC CCACGGGCGG CGGCCTGGGC GAAGATATTT CTGGGATCAC TAACGTCATA
                                                                5760
GTTGTGTTCC AGGATGAGAT CGTCATAGGC CATTTTTACA AAGCGCGGGC GGAGGGTGCC
                                                                5820
AGACTGCGGT ATAATGGTTC CATCCGGCCC AGGGGCGTAG TTACCCTCAC AGATTTGCAT
                                                                5880
TTCCCACGCT TTGAGTTCAG ATGGGGGGAT CATGTCTACC TGCGGGGCGA TGAAGAAAAC
                                                                5940
GGTTTCCGGG GTAGGGGAGA TCAGCTGGGA AGAAAGCAGG TTCCTGAGCA GCTGCGACTT
                                                                6000
ACCGCAGCCG GTGGGCCCGT AAATCACACC TATTACCGGG TGCAACTGGT AGTTAAGAGA
                                                                6060
GCTGCAGCTG CCGTCATCCC TGAGCAGGGG GGCCACTTCG TTAAGCATGT CCCTGACTCG
                                                                6120
CATGTTTTCC CTGACCAAAT CCGCCAGAAG GCGCTCGCCG CCCAGCGATA GCAGTTCTTG
                                                                6180
CAAGGAAGCA AAGTTTTTCA ACGGTTTGAG ACCGTCCGCC GTAGGCATGC TTTTGAGCGT
                                                                6240
TTGACCAAGC AGTTCCAGGC GGTCCCACAG CTCGGTCACC TGCTCTACGG CATCTCGATC
                                                                6300
CAGCATATCT CCTCGTTTCG CGGGTTGGGG CGGCTTTCGC TGTACGGCAG TAGTCGGTGC
                                                                6360
TCGTCCAGAC GGGCCAGGGT CATGTCTTTC CACGGGCGCA GGGTCCTCGT CAGCGTAGTC
                                                                6420
TGGGTCACGG TGAAGGGGTG CGCTCCGGGC TGCGCGCTGG CCAGGGTGCG CTTGAGGCTG
                                                                6480
```

FIGURE 9G

```
GTCCTGCTGG TGCTGAAGCG CTGCCGGTCT TCGCCCTGCG CGTCGGCCAG GTAGCATTTG
                                                             6540

ACCATGGTGT CATAGTCCAG CCCCTCCGCG GCGTGGCCCT TGGCGCGCAG CTTGCCCTTG
                                                             6600

GAGGAGGCGC CGCACGAGGG GCAGTGCAGA CTTTTGAGGG CGTAGAGCTT GGGCGCGAGA
                                                             6660

AATACCGATT CCGGGGAGTA GGCATCCGCG CCGCAGGCCC CGCAGACGGT CTCGCATTCC
                                                             6720

ACGAGCCAGG TGAGCTCTGG CCGTTCGGGG TCAAAAACCA GGTTTCCCCC ATGCTTTTTG
                                                             6780

ATGCGTTTCT TACCTCTGGT TTCCATGAGC CGGTGTCCAC GCTCGGTGAC GAAAAGGCTG
                                                             6840

TCCGTGTCCC CGTATACAGA CTTGAGAGGC CTGTCCTCGA CCGATGCCCT TGAGAGCCTT
                                                             6900

CAACCCAGTC AGCTCCTTCC GGTGGGCGCG GGGCATGACT ATCGTCGCCG CACTTATGAC
                                                             6960

TGTCTTCTTT ATCATGCAAC TCGTAGGACA GGTGCCGGCA GCGCTCTGGG TCATTTTCGG
                                                             7020

CGAGGACCGC TTTCGCTGGA GCGCGACGAT GATCGGCCTG TCGCTTGCGG TATTCGGAAT
                                                             7080

CTTGCACGCC CTCGCTCAAG CCTTCGTCAC TGGTCCCGCC ACCAAACGTT TCGGCGAGAA
                                                             7140

GCAGGCCATT ATCGCCGGCA TGGCGGCCGA CGCGCTGGGC TACGTCTTGC TGGCGTTCGC
                                                             7200

GACGCGAGGC TGGATGGCCT TCCCCATTAT GATTCTTCTC GCTTCCGGCG GCATCGGGAT
                                                             7260

GCCCGCGTTG CAGGCCATGC TGTCCAGGCA GGTAGATGAC GACCATCAGG GACAGCTTCA
                                                             7320

AGGATCGCTC GCGGCTCTTA CCAGCCTAAC TTCGATCACT GGACCGCTGA TCGTCACGGC
                                                             7380

GATTTATGCC GCCTCGGCGA GCACATGGAA CGGGTTGGCA TGGATTGTAG GCGCCGCCCT
                                                             7440

ATACCTTGTC TGCCTCCCCG CGTTGCGTCG CGGTGCATGG AGCCGGGCCA CCTCGACCTG
                                                             7500

AATGGAAGCC GGCGGCACCT CGCTAACGGA TTCACCACTC CAAGAATTGG AGCCAATCAA
                                                             7560
```

FIGURE 9H

```
TTCTTGCGGA GAACTGTGAA TGCGCAAACC AACCCTTGGC AGAACATATC CATCGCGTCC
                                                                7620

GCCATCTCCA GCAGCCGCAC GCGGCGCATC TCGGGCAGCG TTGGGTCCTG GCCACGGGTG
                                                                7680

CGCATGATCG TGCTCCTGTC GTTGAGGACC CGGCTAGGCT GGCGGGGTTG CCTTACTGGT
                                                                7740

TAGCAGAATG AATCACCGAT ACGCGAGCGA ACGTGAAGCG ACTGCTGCTG CAAAACGTCT
                                                                7800

GCGACCTGAG CAACAACATG AATGGTCTTC GGTTTCCGTG TTTCGTAAAG TCTGGAAACG
                                                                7860

CGGAAGTCAG CGCCCTGCAC CATTATGTTC CGGATCTGCA TCGCAGGATG CTGCTGGCTA
                                                                7920

CCCTGTGGAA CACCTACATC TGTATTAACG AAGCCTTTCT CAATGCTCAC GCTGTAGGTA
                                                                7980

TCTCAGTTCG GTGTAGGTCG TTCGCTCCAA GCTGGGCTGT GTGCACGAAC CCCCGTTCA
                                                                8040

GCCCGACCGC TGCGCCTTAT CCGGTAACTA TCGTCTTGAG TCCAACCCGG TAAGACACGA
                                                                8100

CTTATCGCCA CTGGCAGCAG CCACTGGTAA CAGGATTAGC AGAGCGAGGT ATGTAGGCGG
                                                                8160

TGCTACAGAG TTCTTGAAGT GGTGGCCTAA CTACGGCTAC ACTAGAAGGA CAGTATTTGG
                                                                8220

TATCTGCGCT CTGCTGAAGC CAGTTACCTT CGGAAAAAGA GTTGGTAGCT CTTGATCCGG
                                                                8280

CAAACAAACC ACCGCTGGTA GCGGTGGTTT TTTTGTTTGC AAGCAGCAGA TTACGCGCAG
                                                                8340

AAAAAAAGGA TCTCAAGAAG ATCCTTTGAT CTTTTCTACG GGTCTGACG CTCAGTGGAA
                                                                8400

CGAAAACTCA CGTTAAGGGA TTTTGGTCAT GAGATTATCA AAAGGATCT TCACCTAGAT
                                                                8460

CCTTTTAAAT TAAAAATGAA GTTTTAAATC AATCTAAAGT ATATATGAGT AAACTTGGTC
                                                                8520

TGACAGTTAC CAATGCTTAA TCAGTGAGGC ACCTATCTCA GCGATCTGTC TATTTCGTTC
                                                                8580

ATCCATAGTT GCCTGACTCC CCGTCGTGTA GATAACTACG ATACGGGAGG GCTTACCATC
                                                                8640
```

FIGURE 9I

```
TGGCCCCAGT GCTGCAATGA TACCGCGAGA CCCACGCTCA CCGGCTCCAG ATTTATCAGC
                                                                8700

AATAAACCAG CCAGCCGGAA GGGCCGAGCG CAGAAGTGGT CCTGCAACTT TATCCGCCTC
                                                                8760

CATCCAGTCT ATTAATTGTT GCCGGGAAGC TAGAGTAAGT AGTTCGCCAG TTAATAGTTT
                                                                8820

GCGCAACGTT GTTGCCATTG CTGCAGGCAT CGTGGTGTCA CGCTCGTCGT TTGGTATGGC
                                                                8880

TTCATTCAGC TCCGGTTCCC AACGATCAAG GCGAGTTACA TGATCCCCCA TGTTGTGCAA
                                                                8940

AAAAGCGGTT AGCTCCTTCG GTCCTCCGAT CGTTGTCAGA AGTAAGTTGG CCGCAGTGTT
                                                                9000

ATCACTCATG GTTATGGCAG CACTGCATAA TTCTCTTACT GTCATGCCAT CCGTAAGATG
                                                                9060

CTTTTCTGTG ACTGGTGAGT ACTCAACCAA GTCATTCTGA GAATAGTGTA TGCGGCGACC
                                                                9120

GAGTTGCTCT TGCCCGGCGT CAACACGGGA TAATACCGCG CCACATAGCA GAACTTTAAA
                                                                9180

AGTGCTCATC ATTGGAAAAC GTTCTTCGGG GCGAAAACTC TCAAGGATCT TACCGCTGTT
                                                                9240

GAGATCCAGT TCGATGTAAC CCACTCGTGC ACCCAACTGA TCTTCAGCAT CTTTTACTTT
                                                                9300

CACCAGCGTT TCTGGGTGAG CAAAAACAGG AAGGCAAAAT GCCGCAAAAA AGGGAATAAG
                                                                9360

GGCGACACGG AAATGTTGAA TACTCATACT CTTCCTTTTT CAATATTATT GAAGCATTTA
                                                                9420

TCAGGGTTAT TGTCTCATGA GCGGATACAT ATTTGAATGT ATTTAGAAAA ATAAACAAAT
                                                                9480

AGGGGTTCCG CGCACATTTC CCCGAAAAGT GCCACCTGAC GTCTAAGAAA CCATTATTAT
                                                                9540

CATGACATTA ACCTATAAAA ATAGGCGTAT CACGAGGCCC TTTCGTCTTC AA
                                                            9592
```

METHODS AND COMPOSITIONS FOR GENE THERAPY FOR THE TREATMENT OF DEFECTS IN LIPOPROTEIN METABOLISM

CROSS-REFERENCE TO RELATED APPLICATIONS

This is a national phase pursuant to 35 USC §371 of PCT/US96/03041, filed Feb. 23, 1996, which claims priority of U.S. patent application Ser. No. 08/393,734, filed Feb. 24, 1995, now issued as U.S. Pat. No. 5,652,224.

This invention was supported by the National Institute of Health Grant Nos. DK 42193-05 and HD 29946. The United States government has rights in this invention.

FIELD OF THE INVENTION

The present invention relates to the field of somatic gene therapy and the treatment of genetic disorders related to lipoprotein metabolism.

BACKGROUND OF THE INVENTION

The metabolism of lipids, particularly cholesterol, involves the interaction of a number of lipoproteins and apolipoproteins. Very low density lipoprotein (VLDL) and apolipoprotein E (apoE) are key precursor molecules in the production of low density lipoprotein (LDL) and in the overall metabolism of lipids, including cholesterol. LDL is the major cholesterol-transport lipoprotein in human plasma.

The VLDL/apoE receptors are expressed in heart, skeletal muscle, and adipose tissue [F. M. Wittmaack et al, *Endocrinol.*, 136(1):340–348 (1995)] with lower levels of expression in the kidney, placenta, pancreas, and brain. This receptor has been suggested to play a role in the uptake of triglyceride-rich lipoprotein particles by specific organs. The cDNA encoding the putative human VLDL receptor was recently cloned [M. E. Gafvels et al, *Som. Cell Mol. Genet.*, 19:557–569 (1993), incorporated by reference herein]. The receptor for LDL is located in coated pits on the surfaces of cells in the liver and other organs.

As depicted in FIG. 1A, in a normal healthy human, the molecules apolipoprotein B48 (Apo-B48), apolipoprotein C-II (Apo-C-II) and Apo E form a chylomicron particle in plasma passing through the intestines, which interacts with a chylomicron remnant receptor in the liver. After metabolism of the chylomicrons taken up by the remnant receptor, the liver produces the primary lipoprotein, VLDL, which contains Apo-E, Apo-C-II and apolipoprotein B100 (Apo B100). VLDL is metabolized into LDL, which binds to the LDL receptor in the liver via Apo B100. The LDL receptor in the liver facilitates the uptake of LDL by receptor-mediated endocytosis. LDL is degraded in lysosomes, and its cholesterol is released for metabolic use.

Defects in the metabolism of such lipoproteins and/or receptors result in several serious metabolic disorders. The human disease familial hyper-cholesterolemia (FH) is caused primarily by one or more mutations in the gene encoding the LDL receptor. FH is characterized clinically by (1) an elevated concentration of LDL; (2) deposition of LDL-derived cholesterol in tendons and skin (xanthomas) and in arteries (atheromas); and (3) inheritance as an autosomal dominant trait with a gene dosage effect. Individuals with FH develop premature coronary heart disease, usually in childhood. Heterozygotes number about 1 in 500 persons, placing FH among the most common inborn errors of metabolism. Heterozygotes have twofold elevations in plasma cholesterol (350 to 550 mg/dl) from birth and tend to develop tendon xanthomas and coronary atherosclerosis after age 20. Homozygotes number 1 in 1 million persons and are characterized by severe hypercholesterolemia (650 to 1000 mg/dl), cutaneous xanthomas which appear within the first 4 years of life, and coronary heart disease which begins in childhood and frequently causes death before age 20. [J. Goldstein et al, "Familial Hypercholesterolemia", Chapter 48, in *The Metabolic Basis of Inherited Disease*, 6th ed., C. R. Scrivers et al (eds), McGraw-Hill Information Services Co., NY, N.Y., (1989) pp. 1215–1250].

Another metabolic disorder is familial combined hyperlipidemia (FCH) which was first associated with hyperlipidemia in survivors of myocardial infarction and their relatives. FCH patients generally have one of three phenotypes: (1) elevated levels of VLDL, (2) elevated levels of LDL, or (3) increases in the levels of both lipoproteins in plasma. Unlike FH, FCH appears in only 10 to 20 percent of patients in childhood, usually in the form of hypertriglyceridemia. Homozygosity for the trait may result in severe hypertriglyceridemia. [J. Goldstein et al, "Disorders of the Biogenesis and Secretion of Lipoproteins", Chapter 44B in *The Metabolic Basis of Inherited Disease*, 6th ed., C. R. Scrivers et al (eds), McGraw-Hill Information Services Co., NY, N.Y., (1989) pp. 1155–1156]. This disorder is also associated with the appearance of glucose intolerance and obesity in a number of individuals.

The most striking abnormality of FCH is marked elevation of VLDL content of plasma. Increased production of VLDL leads to an expanded plasma pool of VLDL in some individuals, but in others with more efficient lipolysis, it results in increased levels of LDL. FCH is characterized by an excess production of LDL, rather than a genetic defect in the LDL receptor. The LDL receptors of cultured fibroblasts appear to be normal in FCH patients.

Clinical experience suggests that FCH is at least five times as prevalent as FH, occurring in about 1 percent of the North American population. The predilection toward coronary artery disease among patients with this disorder makes it the most prominent known metabolic cause of premature atherosclerosis [J. Goldstein et al, cited above].

When LDL receptors are deficient as in FH (see FIG. 1B), or excess LDL is produced due to excess VLDL as in FCH, the efficient removal of LDL from plasma by the liver declines, and the level of LDL rises in inverse proportion to the receptor number. The excess plasma LDL is deposited in connective tissues and in scavenger cells, resulting in the symptoms of either disorder.

Presently, treatment for FH and FCH is directed at lowering the plasma level of LDL by the administration of drugs, i.e., combined administration of a bile acid-binding resin and an inhibitor of 3-hydroxy-3-methylglutaryl CoA reductase for treatment of FH and niacin for treatment of FCH. However, FH homozygotes with two nonfunctional genes are resistant to drugs that work by stimulating LDL receptors. Similarly, such drugs are not particularly effective in FCH. In FH homozygotes, plasma LDL levels can be lowered only by physical or surgical means.

Administration of normal LDL receptor genes by gene therapy using an adenovirus vector has been contemplated for the treatment of FH. Adenovirus vectors are capable of providing extremely high levels of transgene delivery to virtually all cell types, regardless of the mitotic state. The efficacy of this system in delivering a therapeutic transgene in vivo that complements a genetic imbalance has been demonstrated in animal models of various disorders [K. F. Kozarsky et al, *Somatic Cell Mol. Genet.*, 19:449–458

(1993) ("Kozarsky I"); K. F. Kozarsky et al, *J. Biol. Chem.*, 269:13695–13702 (1994) ("Kozarsky II"); Y. Watanabe, *Atherosclerosis*, 36:261–268 (1986); K. Tanzawa et al, *FEBS Letters*, 118(1):81–84 (1980); J. L. Golasten et al, *New Engl. J. Med.*, 309:288–296 (1983); S. Ishibashi et al, *J. Clin. Invest.*, 92:883–893 (1993); and S. Ishibashi et al, *J. Clin. Invest.*, 93:1885–1893 (1994)]. The use of adenovirus vectors in the transduction of genes into hepatocytes in vivo has previously been demonstrated in rodents and rabbits [see, e.g., Kozarsky II, cited above, and S. Ishibashi et al, *J. Clin. Invest.*, 92:883–893 (1993)].

Recent research has shown that introduction of a recombinant adenovirus encoding the human LDL receptor ("LDLR") cDNA into the livers of LDL receptor-deficient Watanabe heritable hyperlipidemic (WHHL) rabbits, which mimic the condition of FH, resulted in large, transient reductions in plasma cholesterol. The transient nature of the effect of recombinant adenoviruses in most situations is attributed to the development of cellular immune responses to the virus-infected cells and their subsequent elimination. Antigenic targets for immune mediated clearance are viral proteins expressed from the recombinant viral genome and/or the product of the transgene, which in this case, is the LDL receptor protein [Y. Yang et al, *Proc. Natl. Acad. Sci., USA*, 91:4407–4411 (May 1994); Y. Yang et al, *Immun.*, 1:433–442 (August 1994)].

Additionally, repeated reinfusions of the LDLR gene-containing adenovirus did not produce similar, subsequent cholesterol reductions due to the development of neutralizing anti-adenovirus antibodies [Kozarsky I and Kozarsky II, cited above; see also Y. Yang et al, *Immun.*, 1:433–442 (August 1994), all incorporated by reference herein].

There remains a need in the art for therapeutic compositions and gene therapy strategies which enable effective treatment and/or prevention of FH and FCH, as well as other defects in lipoprotein metabolism.

SUMMARY OF THE INVENTION

In one aspect, the invention provides a recombinant viral vector comprising the DNA of, or corresponding to, at least a portion of the genome of an adenovirus, which portion is capable of infecting a hepatic cell; and a human VLDL receptor ("VLDLR") gene operatively linked to regulatory sequences directing its expression, the vector capable of expressing the VLDLR gene product in the hepatic cell in vivo or in vitro.

In another aspect, the invention provides a mammalian cell infected with the viral vector described above.

In still a further aspect, the invention provides a method for delivering and stably integrating a VLDLR gene into the chromosome of a mammalian hepatocyte cell comprising introducing into said cell an effective amount of a recombinant viral vector described above.

Another aspect of this invention is a method for treating a patient having a metabolic disorder comprising administering to the patient by an appropriate route an effective amount of an above described vector containing a normal VLDLR gene, wherein said VLDLR gene is integrated into the chromosome of said patient's hepatocytes and said receptor is expressed stably in vivo at a location in the body where it is not normally expressed.

Other aspects and advantages of the present invention are described further in the following detailed description of the preferred embodiments thereof.

BRIEF DESCRIPTION OF THE DRAWINGS

FIG. 1A is a schematic drawing of normal human and rabbit lipoprotein metabolism. The apolipoproteins are referred to as B48, B100, C-II, and E. LDL and VLDL are identified.

FIG. 1C is a schematic drawing of lipoprotein metabolism in rabbits infused with the recombinant VLDLR gene according to the invention.

FIGS. 8A–8F are the DNA sequence [SEQ ID NO: 1] with encoded amino acid sequence [SEQ ID NO: 2] of the human VLDL receptor gene, as reported by Gafvels et al, cited above.

FIGS. 9A–9I are the DNA sequence of pAd.CMVVLDLR [SEQ ID NO: 3], in which Ad 0–1 spans nucleotides 12–364, CMV ehn/prom spans nucleotides 381–862; nucleotides 966–4107 encode VLDLR, pA spans nucleotides 4192–4390; Ad 9.2–16.1 span nucleotides 4417–6880 and nucleotides 6881–9592 are pAT153 sequences.

DETAILED DESCRIPTION OF THE INVENTION

The present invention provides novel compositions and methods which enable the therapeutic treatment of metabolic disorders, such as FH and FCH, characterized by the accumulation of LDL in human plasma. This invention provides for the use of a viral vector to introduce and stably express a gene normally expressed in mammals, i.e., the gene encoding a normal receptor for very low density lipoprotein (VLDLR), in a location in the body where that gene is not naturally present, i.e., in the liver.

The methods and compositions of the present invention overcome the problems previously identified in the gene therapy treatment of LDL receptor-deficient individuals. As described in detail below, by use of a viral vector capable of targeting cells of the liver, the VLDL receptor gene is introduced into and stably expressed in liver cells. The present invention differs from direct gene replacement in that the VLDL receptor protein is expressed normally in LDL receptor deficient individuals, e.g., the macrophages. Thus, gene therapy using a liver-directed viral vector carrying a VLDLR gene would result not in expression of a new gene product, but rather, in de novo expression in an organ which otherwise does not express the gene product. Importantly, the patient does not mount an immune response against the VLDLR gene product expressed in the liver because the vector-delivered VLDLR gene is not recognized as a foreign antigen, and there is no induction of CTL-mediated elimination of the transfected cell. In contrast, CTL-mediated elimination of viral vectors is a problem when an LDLR gene is administered to an LDLR-deficient individual with FH [see, e.g., Kozarsky I and II, cited above].

Due to this recognition of the VLDLR gene by the patient's immune system as a known gene, and to the tendency of hepatocytes to have a long life in circulation, the hepatocytes transfected with the vector of this invention, which express the VLDLR gene, tend to be stable and VLDLR expression is not transient. VLDLR gene expression in transfected hepatocytes occurs for the duration of the hepatocyte's life. The lipoprotein metabolic disorder may be treated for longer times without the need for reinfusing the viral vector, thus limiting the number of viral exposures and potential immune reactions to vector-encoded viral proteins.

The vectors and methods of this invention can provide gene therapy useful to treat and/or supplement current treatments for lipoprotein metabolic disorders. The presence of the VLDL receptor gene in the transfected hepatocytes according to this invention permits the binding of VLDL, a precursor of LDL, from the plasma at the site of the liver, thereby decreasing the amount of VLDL in plasma. The decrease in VLDL in the plasma consequently decreases the production of plasma LDL.

Figure 1B:
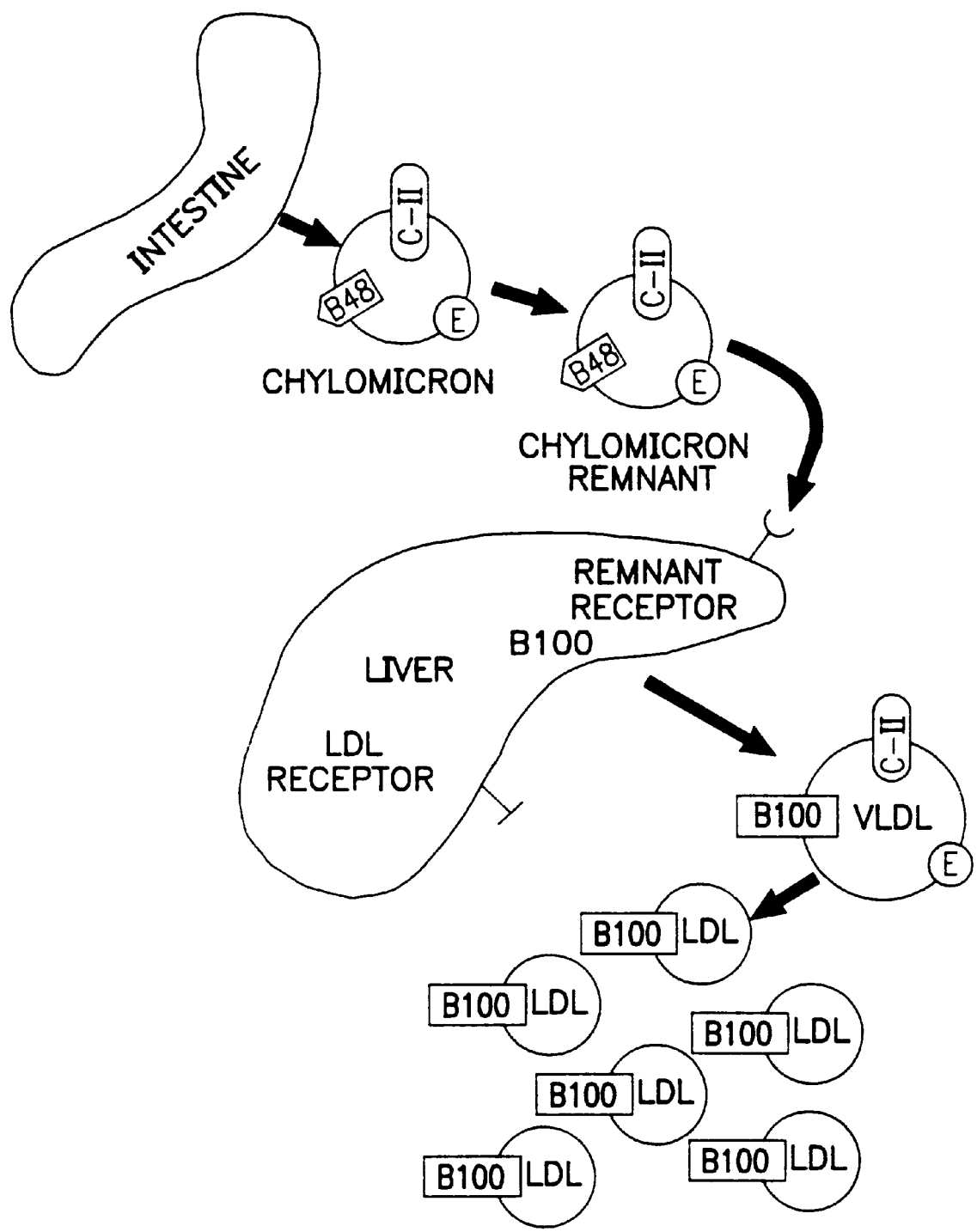
FIG. 1B is a schematic drawing of lipoprotein metabolism in FH patients and WHHL rabbits. The abbreviations are as described in FIG. 1A.

For example, in FH, this reduction in plasma LDL can compensate for the defective LDL receptors in the liver. In FCH, this reduced production of plasma LDL from VLDL prevents the normal LDL receptors in the liver from becoming overloaded by excess LDL, and reduces the excess VLDL which contributes to the disorder. Compare, for example, the schematic representations of the normal operation of lipid metabolism (FIG. 1A) to the abnormal metabolism caused by FH (FIG. 1B) and then to the method of this invention (FIG. 1C).

I. Recombinant Viral Particles as Gene Therapy Vectors

The compositions of this invention involve the construction of desirable gene therapy vectors, which are capable of delivering and stably integrating a functional, normal VLDL receptor gene to hepatocytes. Such gene therapy vectors include a selected virus vector, desirably deleted in one or more viral genes, a minigene containing the VLDLR gene under the control of regulatory sequences, and optional helper viruses and/or packaging cell lines which supply to the viral vectors any necessary products of deleted viral genes.

The viral sequences used in the vectors, helper viruses, if needed, and recombinant viral particles, and other vector components and sequences employed in the construction of the vectors described herein are obtained from commercial or academic sources based on previously published and described sequences. These viral materials may also be obtained from an individual patient. The viral sequences and vector components may be generated by resort to the teachings and references contained herein, coupled with standard recombinant molecular cloning techniques known and practiced by those skilled in the art. Modifications of existing nucleic acid sequences forming the vectors, including sequence deletions, insertions, and other mutations taught by this specification may be generated using standard techniques.

The methods employed for the selection of viral sequences useful in a vector, the cloning and construction of VLDLR "minigene" and its insertion into a desired viral vector and the production of a recombinant infectious viral particle by use of helper viruses and the like are within the skill in the art given the teachings provided herein.

A. Construction of the "Minigene"

By "minigene" is meant the combination of the VLDLR gene and the other regulatory elements necessary to transcribe the gene and express the gene product in vivo. The human VLDL receptor sequence has been provided [see, Gafvels et al, cited above; SEQ ID NOS: 1 and 2]. Generally, the entire coding region of this receptor sequence is used in the minigene; the 5' and 3' untranslated sequences of SEQ ID NO: 1 are not essential to the minigene. VLDL receptor genes of other mammalian origins, e.g., rabbit, monkey, etc., may also be useful in this invention.

The VLDL receptor gene (VLDLR) is operatively linked to regulatory components in a manner which permits its transcription. Such components include conventional regulatory elements necessary to drive expression of the VLDLR transgene in a cell transfected with the viral vector. Thus the minigene also contains a selected promoter which is linked to the transgene and located, with other regulatory elements, within the selected viral sequences of the recombinant vector.

Selection of the promoter is a routine matter and is not a limitation of this invention. Useful promoters may be constitutive promoters or regulated (inducible) promoters, which will enable control of the amount of the transgene to be expressed. For example, a desirable promoter is that of the cytomegalovirus immediate early promoter/enhancer [see, e.g., Boshart et al, Cell, 41:521–530 (1985)]. Another desirable promoter includes the Rous sarcoma virus LTR promoter/enhancer. Still another promoter/enhancer sequence is the chicken cytoplasmic β-actin promoter [T. A. Kost et al, Nucl. Acids Res., 11(23):8287 (1983)]. Other suitable promoters may be selected by one of skill in the art.

The minigene may also desirably contain nucleic acid sequences heterologous to the viral vector sequences including sequences providing signals required for efficient polyadenylation of the transcript (poly-A or pA) and introns with functional splice donor and acceptor sites. A common poly-A sequence which is employed in the exemplary vectors of this invention is that derived from the papovavirus SV-40. The poly-A sequence generally is inserted in the minigene following the transgene sequences and before the viral vector sequences. A common intron sequence is also derived from SV-40, and is referred to as the SV-40 T intron sequence. A minigene of the present invention may also contain such an intron, desirably located between the promoter/enhancer sequence and the transgene. Selection of these and other common vector elements are conventional [see, e.g., Sambrook et al, "Molecular Cloning. A Laboratory Manual.", 2d ed., Cold Spring Harbor Laboratory, New York (1989) and references cited therein] and many such sequences are available from commercial and industrial sources as well as from Genbank.

As stated above, the minigene is located in the site of any selected deletion in the viral vector. See Example 1 below.

B. Construction of the Viral Plasmid Vector

Although a number of viral vectors have been suggested for gene therapy, the most desirable vector for this purpose is a recombinant adenoviral vector or adeno-associated vector. Adenovirus vectors as described below are preferred because they can be purified in large quantities and highly concentrated, and the virus can transduce genes into non-dividing cells. However, it is within the skill of the art for other adenovirus, or even retrovirus, vaccinia or other virus vectors to be similarly constructed.

Adenoviruses are eukaryotic DNA viruses that can be modified to efficiently deliver a therapeutic or reporter transgene to a variety of cell types. Human adenoviruses comprise a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis [see, e.g., Horwitz, Virology, 2d edit., ed. B. N. Fields, Raven Press, Ltd. , New York (1990)]. The general adenoviruses types 2 and 5 (Ad2 and Ad5, respectively), are not associated with human malignancies.

Suitable adenovirus vectors useful in gene therapy are well known [see, e.g., M. S. Horwitz et al, "Adenoviridae and Their Replication", Virology, second edition, pp. 1712, ed. B. N. Fields et al, Raven Press Ltd., New York (1990); M. Rosenfeld et al, Cell, 68:143–155 (1992); J. F. Engelhardt et al, Human Genet. Ther., 4:759–769 (1993); Y. Yang et al, Nature Genet., 7:362–269 (1994); J. Wilson, Nature, 365:691–692 (October 1993); B. J. Carter, in "Handbook of Parvoviruses", ed. P. Tijsser, CRC Press, pp. 155–168 (1990). The selection of the adenovirus type is not anticipated to limit the following invention.

Adenovirus vectors useful in this invention may include the DNA sequences of a number of adenovirus types. The adenovirus sequences useful in the vectors described herein may be obtained from any known adenovirus type, including the presently identified 41 human types [see, e.g., Horwitz, cited above]. The sequence of a strain of adenovirus type 5 may be readily obtained from Genbank Accession No. M73260. Similarly, adenoviruses known to infect other animals may also be employed in the vector constructs of this invention. A variety of adenovirus strains are available from the American Type Culture Collection, Rockville, Md., or available by request from a variety of commercial and institutional sources.

Adenovirus vectors useful in this invention include recombinant, defective adenoviruses, optionally bearing other mutations, e.g., temperature-sensitive mutations, deletions and hybrid vectors formed with adenovirus/adeno-associated virus sequences. Suitable vectors are described in the published literature [see, for example, Kozarsky I and II, cited above, and references cited therein, U.S. Pat. No. 5,240,846 and the co-pending applications incorporated herein by reference below.

Useful adenovirus vectors for delivery of the VLDLR gene to the liver, minimal adenovirus nucleic acid sequences may be used to make a vector, in which case the use of a helper virus to produce a hybrid virus particle is required. Alternatively, only selected deletions of one or more adenovirus genes may be employed to construct a viral vector. Deleted gene products can be supplied by using a selected packaging cell line which supplies the missing gene product.

1. Recombinant Minimal Adenovirus

Desirable adenovirus (Ad) vectors useful in the present invention are described in detail in co-pending, co-owned U.S. patent application Ser. No. 08/331,381, which is incorporated by reference herein for the purpose of describing these vectors.

Briefly summarized, the minimal Ad virus is a viral particle containing only the adenovirus cis-elements necessary for replication and virion encapsidation, but otherwise deleted of all adenovirus genes. That is, the vector contains only the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. This left terminal (5') sequence of the Ad5 genome spans bp 1 to about 360 of the conventional published Ad5 adenovirus genome, also referred to as map units 0–1 of the viral genome, and generally is from about 353 to about 360 nucleotides in length. This sequence includes the 5'ITR (bp 1 to about 103 of the adenovirus genome); and the packaging/enhancer domain (bp about 194 to about 358 of the adenovirus genome). The minimal 3' adenovirus sequences of the adenovirus vector may include the right terminal (3') ITR sequence of the adenoviral genome spanning about bp 35,353 to the end of the adenovirus genome, or map units ~98.4–100. This sequence is generally about 580 nucleotide in length. Between such sequences, a VLDLR minigene, as described above, is inserted.

Production of an infectious particle from this minimal Ad viral vector involves the assistance of a helper virus, as discussed below. A second type of minimal vector also disclosed in the above-incorporated reference places the 5' Ad terminal sequence in a head-to-tail arrangement relative to the 3' terminal sequence. The minimal Ad vector co-infected with a helper virus and/or a packaging cell line provides all of the viral gene products necessary to produce an infective recombinant viral particle containing the VLDLR minigene. Alternatively, this vector can contain additional adenovirus gene sequences, which then are not required to be supplied by a helper virus.

2. Other Defective Adenoviruses

Recombinant, replication-deficient adenoviruses useful for gene therapy of this invention may be characterized by containing more than the minimal adenovirus sequences defined above. These other Ad vectors can be characterized by deletions of various portions of gene regions of the virus, and infectious virus particles formed by the optional use of helper viruses and/or packaging cell lines. Suitable defective adenoviruses are described in more detail in Kozarsky and Wilson, *Curr. Opin. Genet. Devel.*, 3:499–503 (1993); Kozarsky I and II, cited above, and references cited therein, all incorporated herein by reference.

As one example, suitable vectors may be formed by deleting all or a sufficient portion of the adenoviral early immediate early gene E1a (which spans mu 1.3 to 4.5) and delayed early gene E1b (which spans mu 4.6 to 11.2) so as to eliminate their normal biological functions. These replication-defective E1-deleted viruses are capable of replicating and producing infectious virus when grown on an adenovirus-transformed, complementation human embryonic kidney cell line, the 293 cell [ATCC CRL1573], containing functional adenovirus E1a and E1b genes which provide the corresponding gene products in trans. The resulting virus is capable of infecting many cell types and can express a transgene (i.e., VLDLR gene), but cannot replicate in most cells that do not carry the E1 region DNA unless the cell is infected at a very high multiplicity of infection. Extensive experience in animals indicates that E1-deleted vectors are not particularly desirable for gene therapy because low levels of viral proteins are expressed which elicit destructive cellular immune responses.

As a preferred example, all or a portion of the adenovirus delayed early gene E3 (which spans mu 76.6 to 86.2) may be eliminated from the adenovirus sequence which forms a part of the hybrid construct. The function of E3 is irrelevant to the function and production of the recombinant virus particle. For example, Ad vectors may be constructed with a therapeutic minigene inserted into the E1-deleted region of the known mutant Ad5 sub360 backbone [J. Logan et al, *Proc. Natl. Acad. Sci. USA*, 81:3655–3659 (1984)]; or the Ad5 mutant dl7001 backbone [Dr. William Wold, Washington University, St. Louis]. Both mutant viruses also contain a deletion in the E3 region of the adenoviral genome; in sub360, at 78.5 to 84.3 mu, and in dl7001, at 78.4 to 86 mu. The life cycle of both sub360 and dl7001 display wild type characteristics.

More preferred adenovirus vectors may be constructed having a deletion of the E1 gene, at least a portion of the E3 region, and an additional deletion within adenovirus genes other than E1 and E3 to accommodate the VLDLR minigene and/or other mutations which result in reduced expression of adenoviral protein and/or reduced viral replication. For example, all or a portion of the adenovirus delayed early gene E2a (which spans mu 67.9 to 61.5) may be eliminated from the adenovirus vector. It is also anticipated that portions of the other delayed early genes E2b (which spans mu 29 to 14.2) and E4 (which spans mu 96.8 to 91.3) may also be eliminated from the adenovirus vector.

Deletions may also be made in any of the late genes L1 through L5, which span mu 16.45 to 99 of the adenovirus genome. Similarly, deletions may be useful in the intermediate genes IX (which maps between mu 9.8 and 11.2) and $IVa_2$ (which maps between 16.1 to 11.1). Other useful deletions may also be made in the other structural or non-structural adenovirus genes.

An adenovirus sequence for use in the present invention may contain deletions of E1 only. Alternatively, deletions of entire genes or portions effective to destroy their biological activity may be used in any combination. For example, in one exemplary vector, the adenovirus sequence may contain deletions of the E1 genes and the E3 gene, or of the E1, E2a and E3 genes, or of the E1 and E4 genes, or of E1, E2a and E4 genes, with or without deletion of E3, and so on.

Vectors may also contain additional mutations in genes necessary for viral replication. Adenovirus vectors may contain a mutation which produces temperature-sensitive (ts) viruses. Among such mutations include the incorporation of the missense temperature-sensitive mutation in the E2a region found in the Ad5 H5ts125 strain [P. Vander Vliet et al, *J. Virol.*, 15:348–354 (1975)] at 62.5 mu. A single amino acid substitution (62.5 mu) at the carboxy end of the 72 kd protein (DBP) produced from the E2a gene in this strain produces a protein product which is a single-stranded DNA binding protein and is involved in the replication of adenoviral genomic DNA. At permissive temperatures (approximately 32° C.) the ts strain is capable of full life cycle growth on HeLa cells, while at non-permissive temperatures (approximately 38° C.), no replication of adenoviral DNA is seen. In addition, at non-permissive temperatures, decreased immunoreactive 72 kd protein is seen in HeLa cells.

Exemplary vectors for use in this invention, for example, may be obtained by combining fragments from three independent DNA constructs, including sub360 or dl7001, H5ts125, and a cDNA plasmid with E1a sequences placed 5' to a therapeutic minigene. This type of vector is described, for example, by J. F. Engelhardt et al, *Proc. Natl. Acad. Sci. USA*, 91:6196–6200 (June 1994); Y. Yang et al, *Nature Genet.*, 7: 362–369 (July, 1994) and references cited therein, all references incorporated herein by reference. Due to the mutations in the vector, there is reduced viral replication, reduction in expressed protein and an increase in the persistence of transgene expression. Other preferred adenovirus vectors contain the H5ts125 mutation in addition to E3 deletions of sub360 and dl7001. The minigene containing VLDLR as the transgene may be inserted into any deleted region of the selected Ad virus.

An exemplary Ad virus vector used to demonstrate this invention is the defective adenovirus vector H5.010CMVVLDLR, which contains adenovirus sequences Ad m.u. 0–1, followed by a VLDLR minigene, and the sequence Ad m.u.9 to 100 with small deletions in E3. See FIG. 3, described above. The recombinant adenovirus was fully deleted of E1a, E1b and partially deleted of E3. This recombinant virus vector is described in detail in Example 1.

3. Ad/AAV Hybrid Vectors

Another preferred vector is a hybrid Ad/AAV vector, which is the subject of co-owned, co-pending U.S. patent application Ser. No. 08/331,384, now U.S. Pat. No. 5,856,152 which is incorporated by reference herein.

At a minimum, the adenovirus nucleic acid sequences employed in the hybrid vector of this invention are the minimal adenovirus genomic sequences required for packaging adenoviral genomic DNA into a preformed capsid head, as described above. The entire adenovirus 5' sequence containing the 5' ITR and packaging/enhancer region can be employed as the 5' adenovirus sequence in the hybrid vector. The 3' adenovirus sequences of the vector include the right terminal (3') ITR sequence of the adenoviral genome discussed above. Some modifications to these sequences which do not adversely affect their biological function may be acceptable.

Also part of the hybrid vectors of this invention are sequences of an adeno-associated virus. The AAV sequences useful in the hybrid vector are the viral sequences from which the rep and cap polypeptide encoding sequences are deleted. More specifically, the AAV sequences employed are the cis-acting 5' and 3' inverted terminal repeat (ITR) sequences [See, e.g., B. J. Carter, cited above]. The AAV ITR sequences are about 143 bp in length. Substantially the entire sequences encoding the ITRs are used in the vectors, although some degree of minor modification of these sequences is expected to be permissible for this use. The ability to modify these ITR sequences is within the skill of the art. See, e.g., Sambrook et al, cited above.

In the Ad/AAV hybrid vector construct, the AAV sequences are flanked by the adenovirus sequences discussed above. The 5' and 3' AAV ITR sequences themselves flank a VLDLR minigene sequence as described above. Thus, the sequence formed by the VLDLR minigene and flanking 5' and 3' AAV sequences may be inserted at any deletion site in the adenovirus sequences of the vector. For example, the AAV sequences are desirably inserted at the site of deleted E1a/E1b genes of the adenovirus, i.e., after map unit 1. Alternatively, the AAV sequences may be inserted at an E3 deletion, E2a deletion, and so on. If only the adenovirus 5' ITR/packaging sequences and 3' ITR sequences are used in the vector, the AAV sequences are inserted between them.

As described above for the minimum adenovirus sequences, those gene sequences not present in the adenovirus portion of the hybrid vector must be supplied by either a packaging cell line and/or a helper adenovirus to generate the recombinant hybrid viral particle. Uptake of this hybrid virus by the cell is caused by the infective ability contributed to the vector by the adenovirus and AAV sequences. Once the virus or virus conjugate is taken up by a cell, the AAV ITR flanked transgene must be rescued from the parental adenovirus backbone. Rescue of the transgene is dependent upon supplying the infected cell with an AAV rep gene.

The AAV rep gene can be supplied to the hybrid virus by several methods described in the above-incorporated application. One embodiment for providing rep proteins in trans is by transfecting into the target monolayer of cells previously infected with the hybrid vector, a liposome enveloped plasmid containing the genes encoding the AAV rep 78 kDa and 52 kDa proteins under the control of the AAV P5 promoter. More preferably for in vivo use, the AAV rep gene may also be delivered as part of the hybrid virus. One embodiment of this single particle concept is supplied by a polycation conjugate of hybrid virus. Infection of this modified virus conjugate is accomplished in the same manner and with regard to the same target cells as identified above. However, the polylysine conjugate of the hybrid virus onto which was directly complexed a plasmid that encoded the rep 78 and 52 proteins, combines all of the functional components into a single particle structure. Thus, the hybrid virus conjugate permits delivery of a single particle to the cell, which is considerably more desirable for therapeutic use. In another embodiment, the hybrid virus is modified by cloning the rep cDNA directly into the adenovirus genome portion of the hybrid vector.

These and additional aspects of this hybrid vector are provided by the above-incorporated by reference application.

C. Production of the Recombinant Viral Particle

1. Helper Viruses/Packaging Cell Lines

Depending upon the adenovirus gene content of the plasmid vectors employed to carry the VLDLR minigene, a packaging cell line or a helper adenovirus or both may be necessary to provide sufficient adenovirus gene sequences necessary to produce an infective recombinant viral particle containing the VLDLR minigene.

Useful helper viruses contain selected adenovirus gene sequences not present in the adenovirus vector construct or expressed by the cell line in which the vector is transfected. A preferred helper virus is desirably replication defective and contains a variety of adenovirus genes in addition to the modified sequences described above. In this setting, the helper virus is desirably used in combination with a packaging cell line that stably expresses adenovirus genes. Helper viruses may also be formed into poly-cation conjugates as described in Wu et al, *J. Biol. Chem.*, 264:16985–16987 (1989); K. J. Fisher and J. M. Wilson, *Biochem. J.*, 299:49 (Apr. 1, 1994), and in U.S. patent application Ser. No. 08/331,381, incorporated by reference herein.

Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification. The construction of desirable helper cells is within the skill of the art.

As one example, if the cell line employed to produce the viral vector is not a packaging cell line, and the vector contains only the minimum adenovirus sequences identified above, the helper virus may be a wild type Ad vector supplying the necessary adenovirus early genes E1, E2a, E4 and all remaining late, intermediate, structural and non-structural genes of the adenovirus genome. However, if, in this situation, the packaging cell line is 293, which supplies the E1 proteins, the helper cell line need not contain the E1 gene.

In another embodiment, if the adenovirus vector construct is replication defective (no E1 gene and optionally no E3 gene) and the 293 cell line is employed, no helper virus is necessary for production of the hybrid virus. E3 may be eliminated from the helper virus because this gene product is not necessary for the formation of a functioning virus particle.

Preferably, to facilitate purification and reduce contamination of the viral vector particle with the helper virus, it is useful to modify the helper virus' native adenoviral gene sequences which direct efficient packaging, so as to substantially disable or "cripple" the packaging function of the helper virus or its ability to replicate.

A desirable "crippled" adenovirus is modified in its 5' ITR packaging/enhancer domain, which normally contains at least seven distinct yet functionally redundant sequences necessary for efficient packaging of replicated linear adenovirus genomes ("PAC" sequences). Within a stretch of nucleotide sequence from bp 194–358 of the Ad5 genome, five of these PAC sequences are localized: PAC I or its complement at bp 241–248 [SEQ ID NO: 4], PAC II or its complement at bp 262–269 [SEQ ID NO: 5], PAC III or its complement at bp 304–311 (SEQ ID NO: 6], PAC IV or its complement at bp 314–321 [SEQ ID NO: 7], and PAC V or its complement at bp 339–346 [SEQ ID NO: 8].

Mutations or deletions may be made to one or more of these PAC sequences in an adenovirus helper virus to generate desirable crippled helper viruses. Modifications of this domain may include 5' adenovirus sequences which contain less than all five of the native adenovirus PAC sequences, including deletions of contiguous or non-contiguous PAC sequences. An alternative modification may be the replacement of one or more of the native PAC sequences with one or more repeats of a consensus sequence containing the most frequently used nucleotides of the five native PAC sequences. Alternatively, this adenovirus region may be modified by deliberately inserted mutations which disrupt one or more of the native PAC sequences. One of skill in the art may further manipulate the PAC sequences to similarly achieve the effect of reducing the helper virus packaging efficiency to a desired level.

It should be noted that one of skill in the art may design other helper viruses or develop other packaging cell lines to complement the adenovirus deletions in the vector construct and enable production of the recombinant virus particle, given this information. Therefore, the use or description of any particular helper virus or packaging cell line is not limiting.

In the presence of other packaging cell lines which are capable of supplying adenoviral proteins in addition to the E1, the helper virus may accordingly be deleted of the genes encoding these adenoviral proteins. Such additionally deleted helper viruses also desirably contain crippling modifications as described above.

Poly-cation helper virus conjugates, which may be associated with a plasmid containing other adenoviral genes, which are not present in the helper virus may also be useful. The helper viruses described above may be further modified by resort to adenovirus-polylysine conjugate technology. See, e.g., Wu et al, cited above; and K. J. Fisher and J. M. Wilson, cited above.

Using this technology, a helper virus containing preferably the late adenoviral genes is modified by the addition of a poly-cation sequence distributed around the capsid of the helper virus. Preferably, the poly-cation is poly-lysine, which attaches around the negatively-charged vector to form an external positive charge. A plasmid is then designed to express those adenoviral genes not present in the helper virus, e.g., the E1, E2 and/or E4 genes. The plasmid associates to the helper virus-conjugate through the charges on the poly-lysine sequence. This conjugate permits additional adenovirus genes to be removed from the helper virus and be present on a plasmid which does not become incorporated into the virus during production of the recombinant viral vector. Thus, the impact of contamination is considerably lessened.

2. Assembly of Viral Particle and Infection of a Cell Line

Assembly of the selected DNA sequences of the adenovirus, the AAV and the reporter genes or therapeutic genes and other vector elements into the hybrid vector and the use of the hybrid vector to produce a hybrid viral particle utilize conventional techniques. Such techniques include conventional cloning techniques of cDNA such as those described in texts [Sambrook et al, cited above], use of overlapping oligonucleotide sequences of the adenovirus and AAV genomes, polymerase chain reaction, and any suitable method which provides the desired nucleotide sequence. Standard transfection and co-transfection techniques are employed, e.g., $CaPO_4$ transfection techniques using the complementation 293 cell line. Other conventional methods employed include homologous recombination of the viral genomes, plaquing of viruses in agar overlay, methods of measuring signal generation, and the like.

For example, following the construction and assembly of the desired minigene-containing plasmid vector, the vector is infected in vitro in the presence of an optional helper virus and/or a packaging cell line. Homologous recombination occurs between the helper and the vector, which permits the adenovirus-transgene sequences in the vector to be replicated and packaged into virion capsids, resulting in the recombinant vector viral particles. The current method for producing such virus particles is transfection-based. Briefly, helper virus is used to infect cells, such as the packaging cell line human HEK 293, which are then subsequently transfected with an adenovirus plasmid vector containing a VLDLR transgene by conventional methods. About 30 or more hours post-transfection, the cells are harvested, an extract prepared and the recombinant virus vector containing the VLDLR transgene is purified by buoyant density ultracentrifugation in a CsCl gradient.

The yield of transducing viral particles is largely dependent on the number of cells that are transfected with the plasmid, making it desirable to use a transfection protocol with high efficiency. One such method involves use of a poly-L-lysinylated helper adenovirus as described above. A plasmid containing the VLDLR minigene is then completed directly to the positively charged helper virus capsid, resulting in the formation of a single transfection particle containing the plasmid vector and the helper functions of the helper virus.

II. Use of the Recombinant Virus Vectors in Gene Therapy

The resulting recombinant adenoviral vector containing the VLDLR minigene produced by cooperation of the adenovirus vector and helper virus or adenoviral vector and packaging cell line, as described above, thus provides an efficient gene transfer vehicle which can deliver the VLDLR gene to a patient in vivo or ex vivo and provide for integration of the gene into a liver cell.

The above-described recombinant vectors are administered to humans in a conventional manner for gene therapy and serve as an alternative or supplemental gene therapy for LDL receptor deficiencies or other lipoprotein metabolic disorders. A viral vector bearing the VLDLR gene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The viral vectors are administered in sufficient amounts to transfect the liver cells and provide sufficient levels of transfer and expression of the VLDLR gene to provide a therapeutic benefit without undue adverse or with medically acceptable physiological effects which can be determined by those skilled in the medical arts. Conventional and pharmaceutically acceptable routes of administration include direct delivery to the liver, intranasal, intravenous, intramuscular, subcutaneous, intradermal, oral and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 20 to about 100 ml of saline solution containing concentrations of from about $1\times10^9$ to $1\times10^{11}$ pfu/ml virus vector. A preferred human dosage is estimated to be about 50 ml saline solution at $2\times10^{10}$ pfu/ml. The dosage will be adjusted to balance the therapeutic benefit against any adverse side effects. The levels of expression of the VLDLR gene can be monitored to determine the frequency of dosage administration.

An optional method step involves the co-administration to the patient, either concurrently with, or before or after administration of the viral vector, of a suitable amount of an immune modulator, which is preferably short-acting. The selected immune modulator is defined herein as an agent capable of inhibiting the formation of neutralizing antibodies directed against products of the recombinant vector of this invention and/or capable of inhibiting cytolytic T lymphocyte (CTL) elimination of the vector containing cells. The immune modulator may interfere with the interactions between the T helper subsets ($T_{H1}$ or $T_{H2}$) and B cells to inhibit neutralizing antibody formation. Alternatively, the immune modulator may be selected to inhibit the interaction between $T_{H1}$ cells and CTLs to reduce the occurrence of CTL elimination of the vector. More specifically, the immune modulator desirably interferes with, or blocks, the function of the CD4 T cells.

Immune modulators for use in inhibiting neutralizing antibody formation may be selected based on the determination of the immunoglobulin subtype of any neutralizing antibody produced in response to the VLDLR-containing adenovirus vector. For example, if the neutralizing antibody is a $T_{H2}$ mediated antibody, such as IgA, the immune modulator desirably suppresses or prevents the interaction of $T_{H2}$ with B cells. Alternatively, if the induced neutralizing antibody is a $T_{H1}$ mediated antibody, such as $IgG_2A$, the immune modulator desirably suppresses or prevents the interaction of $T_{H1}$ with B cells.

The neutralizing antibody which develops in response to administration of a viral vector of this invention can be based on what vehicle is being used to deliver the vector and/or the location of delivery. For instance, administration of adenoviral vectors via the lungs generally induces production of IgA neutralizing antibody. Administration of adenoviral vectors via the blood generally induces $IgG_1$ neutralizing antibody. The determination of the neutralizing antibody is readily determined in trials of the selected viral vector in animal models. Where the reduction of CTL elimination of the viral vectors is desired, the immune modulator is selected for its ability to suppress or block $CD4^+$ $T_{H1}$ cells to permit prolonged residence of the viral vector in vitro.

Selection of the immune modulator thus may be based upon the mechanism sought to be interrupted or blocked. The immune modulators may be soluble proteins or naturally occurring proteins, including cytokines, monoclonal antibodies. The immune modulators may be conventional pharmaceuticals. The immune modulators identified herein may be used alone or in combination with one another. For example, cyclophosphamide and the more specific immune modulator anti-CD4 monoclonal antibody may be co-administered. In such a case, cyclophosphamide serves as an agent to block $T_{H1}$ activation and stabilized transgene expression beyond the period of transient immune blockade.

A suitable amount or dosage of the immune modulator will depend primarily on the amount of the recombinant vector bearing the VLDLR gene which is initially administered to the patient and the type of immune modulator selected. Other secondary factors such as the condition being treated, the age, weight, general health, and immune status of the patient, may also be considered by a physician in determining the dosage of immune modulator to be delivered to the patient.

Generally, for example, a therapeutically effective human dosage of a cytokine immune modulator, e.g., IL-12 or γ-IFN, is generally in the range of from about 0.5 µg to about 5 mg per about $1\times10^7$ pfu/ml virus vector. Various dosages may be determined by one of skill in the art to balance the therapeutic benefit against any side effects.

A. Monoclonal Antibodies and Soluble Proteins

Preferably, the method of inhibiting an adverse immune response to the gene therapy vector involves non-specific inactivation of $CD4^+$ cells. Preferably, such blocking antibodies are "humanized" to prevent the recipient from mounting an immune response to the blocking antibody. A "humanized antibody" refers to an antibody having its complementarily determining regions (CDRs) and/or other portions of its light and/or heavy variable domain framework regions derived from a non-human donor immunoglobulin, the remaining immunoglobulin-derived parts of the molecule being derived from one or more human immunoglobulins. Such antibodies can also include antibodies characterized by a humanized heavy chain associated with a donor or acceptor unmodified light chain or a chimeric light chain, or vice versa. Such "humanization" may be accomplished by methods known to the art. See, for example, G. E. Mark and E. A. Padlan, "Chap. 4. Humanization of Monoclonal Antibodies", The Handbook of Experimental Pharmacology, vol. 113, Springer-Verlag, N.Y. (1994), pp. 105–133, which is incorporated by reference herein.

Other suitable antibodies include those that specifically inhibit or deplete $CD4^+$ cells, such as an antibody directed against cell surface CD4. Depletion of $CD4^+$ cells has been shown by the inventors to inhibit the CTL elimination of the viral vector. Such modulatory agents include but are not limited to anti-T cell antibodies, such as anti-OKT3+ [see, e.g., U.S. Pat. No. 4,658,019; European Patent Application No. 501,233, published Sep. 2, 1992]. See Example 2 below, which employs the commercially available antibody GK1.5 (ATCC Accession No. TIB207) to deplete $CD4^+$ cells.

Alternatively, any agent that interferes with or blocks the interactions necessary for the activation of B cells by TH cells, and thus the production of neutralizing antibodies, is useful as an immune modulator according to these methods. For example, B cell activation by T cells requires certain interactions to occur [F. H. Durie et al, *Immunol. Today*, 15(9):406–410 (1994)], such as the binding of CD40 ligand on the T helper cell to the CD40 antigen on the B cell, and the binding of the CD28 and/or CTLA4 ligands on the T cell to the B7 antigen on the B cell. Without both -5, interactions, the B cell cannot be activated to induce production of the neutralizing antibody.

The CD40 ligand (CD40L)-CD40 interaction is a desirable point to block the immune response to gene therapy vectors because of its broad activity in both T helper cell activation and function as well as the absence of redundancy in its signaling pathway. A currently preferred method of the present invention thus involves transiently blocking the interaction of CD40L with CD40 at the time of adenoviral vector administration. This can be accomplished by treating with an agent which blocks the CD40 ligand on the $T_H$ cell and interferes with the normal binding of CD40 ligand on the T helper cell with the CD40 antigen on the B cell. Blocking CD40L-CD40 interaction prevents the activation of the T helper cells that contributes to problems with transgene stability and readministration.

Thus, an antibody to CD40 ligand (anti-CD40L) [available from Bristol-Myers Squibb Co; see, e.g., European patent application 555,880, published Aug. 18, 1993] or a soluble CD40 molecule can be a selected immune modulator in this method.

Alternatively, an agent which blocks the CD28 and/or CTLA4 ligands present on T helper cells interferes with the normal binding of those ligands with the antigen B7 on the B cell. Thus, a soluble form of B7 or an antibody to CD28 or CTLA4, e.g., CTLA4-Ig [available from Bristol-Myers Squibb Co; see, e.g., European patent application 606,217, published Jul. 20, 1994] can be the selected immune modulator in the method of this invention. This method has greater advantages than the below-described cytokine administration to prevent $T_{H2}$ activation, because it addresses both cellular and humoral immune responses to foreign antigens.

B. Cytokines

Still other immune modulators which inhibit the $T_H$ cell function may be employed in this invention.

Thus, in one embodiment, an immune modulator which selectively inhibits the function of the $T_{H1}$ subset of $CD4^+$ T helper cells may be administered at the time of primary administration of the viral vector. One such immune modulator is interleukin-4 (IL-4). IL-4 enhances antigen specific activity of $T_{H2}$ cells at the expense of the $T_{H1}$ cell function [see, e.g., Yokota et al, Proc. Natl. Acad. Sci., USA, 83:.5894–5898 (1986); U.S. Pat. No. 5,017,691]. It is envisioned that other immune modulators that can inhibit $T_{H1}$ cell function will also be useful in the methods of this invention.

In another embodiment, the immune modulator can be a cytokine that prevents the activation of the $T_{H2}$ subset of T helper cells. The success of this method depends on the relative contribution that TE dependent Ig isotypes play in virus neutralization, the profile of which may be affected by strain, the species of animal as well as the mode of virus delivery and target organ.

A desirable immune modulator which selectively inhibits the $CD4^+$ T cell subset $T_{H2}$ function at the time of primary administration of the viral vector includes interleukin-12 (IL-12). IL-12 enhances antigen specific activity of $T_{H1}$ cells at the expense of $_{H2}$ cell function [see, e.g., European Patent Application No. 441,900; P. Scott, Science, 260:496–497 (1993); R. Manetti et al, J. Exp. Med., 177:1199 (1993); A. D'Andrea et al, J. Exp. Med., 176:1387 (1992)]. IL-12 for use in this method is preferably in protein form. Human IL-12 may be recombinantly produced using known techniques or may be obtained commercially. Alternatively, it may be engineered into a viral vector (which optionally may be the same as that used to express the transgene) and expressed in a target cell in vivo or ex vivo.

$T_{H2}$ specific ablation with IL-12 is particularly effective in lung-directed gene therapies where IgA is the primary source of neutralizing antibody. In liver-directed gene therapy, both $T_{H1}$ and $T_{H2}$ cells contribute to the production of virus specific antibodies. However, the total amount of neutralizing antibody can be diminished with IL-12.

Another selected immune modulator which performs a similar function is gamma interferon (IFN-γ) [S. C. Morris et al, J. Immunol., 152:1047–1056 (1994); F. P. Heinzel et al, J. Exp. Med., 177:1505 (1993)]. IFN-γ is believed to mediate many of the biological effects of IL-12 via secretion of activated macrophages and T helper cells. IFN-γ also partially inhibits IL-4 stimulated activation of $T_{H2}$. IFN-γ may also be obtained from a variety of commercial sources.

Alternatively, it may be engineered into a viral vector and expressed in a target cell in vivo or ex vivo using known genetic engineering techniques.

Preferably, such cytokine immune modulators are in the form of human recombinant proteins. These proteins may be produced by methods extant in the art. Active peptides, fragments, subunits or analogs of the known immune modulators described herein, such as IL-12 or gamma interferon, which share the $T_{H2}$ inhibitory function of these proteins, will also be useful in this method when the neutralizing antibodies are $T_{H2}$ mediated.

C. Other Pharmaceuticals

Other immune modulators or agents that non-specifically inhibit immune function, i.e., cyclosporin A or cyclophosphamide, may also be used in the methods of the invention. For example, a short course of cyclophosphamide has been demonstrated to successfully interrupt both CD4 and CD8 T helper cell activation to adenovirus capsid protein at the time of virus delivery to the liver. As a result, transgene expression was prolonged and, at higher doses, formation of neutralizing antibody was prevented, allowing successful vector readministration. In the lung, cyclophosphamide prevented formation of neutralizing antibodies at all doses and stabilized transgene expression at high dose.

D. Administration of Immune Modulator

The optional administration of the selected immune modulator may be repeated during the treatment with the recombinant adenovirus vector carrying the human VLDLR gene, during the period of time that the VLDLR gene is expressed (as monitored by e.g., LDL levels), or with every booster of the recombinant vector.

Thus, the compositions and methods of this invention provide a desirable treatment for defects in LDL metabolism, by providing stable expression of the VLDLR gene in human hepatocytes, and the ability to re-administer the vector as desired without incurring an undesired immune response by the patient.

The following examples illustrate the construction and testing of the viral vectors and VLDL receptor gene inserts of the present invention and the use thereof in the treatment of metabolic disorders. An exemplary recombinant adenovirus encoding the human VLDL receptor was constructed as described in Example 1 below. These examples are illustrative only, and do not limit the scope of the present invention.

EXAMPLE 1

Construction and Purification of
H5.010CMVVLDLR

The cDNA for the human very low density lipoprotein (VLDL) receptor [M. E. Gafvels et al, cited above; SEQ ID NO: 1] was inserted into the polylinker region of plasmid pRc/CMV (obtained from Invitrogen Corp.). The resulting plasmid, pRc/CMVVLDLR, was digested with the restriction enzymes SnaBI and NotI and the 4 kb fragment containing the cytomegalovirus (CMV) immediate-early promoter and VLDL receptor cDNA was isolated.

Figure 2:
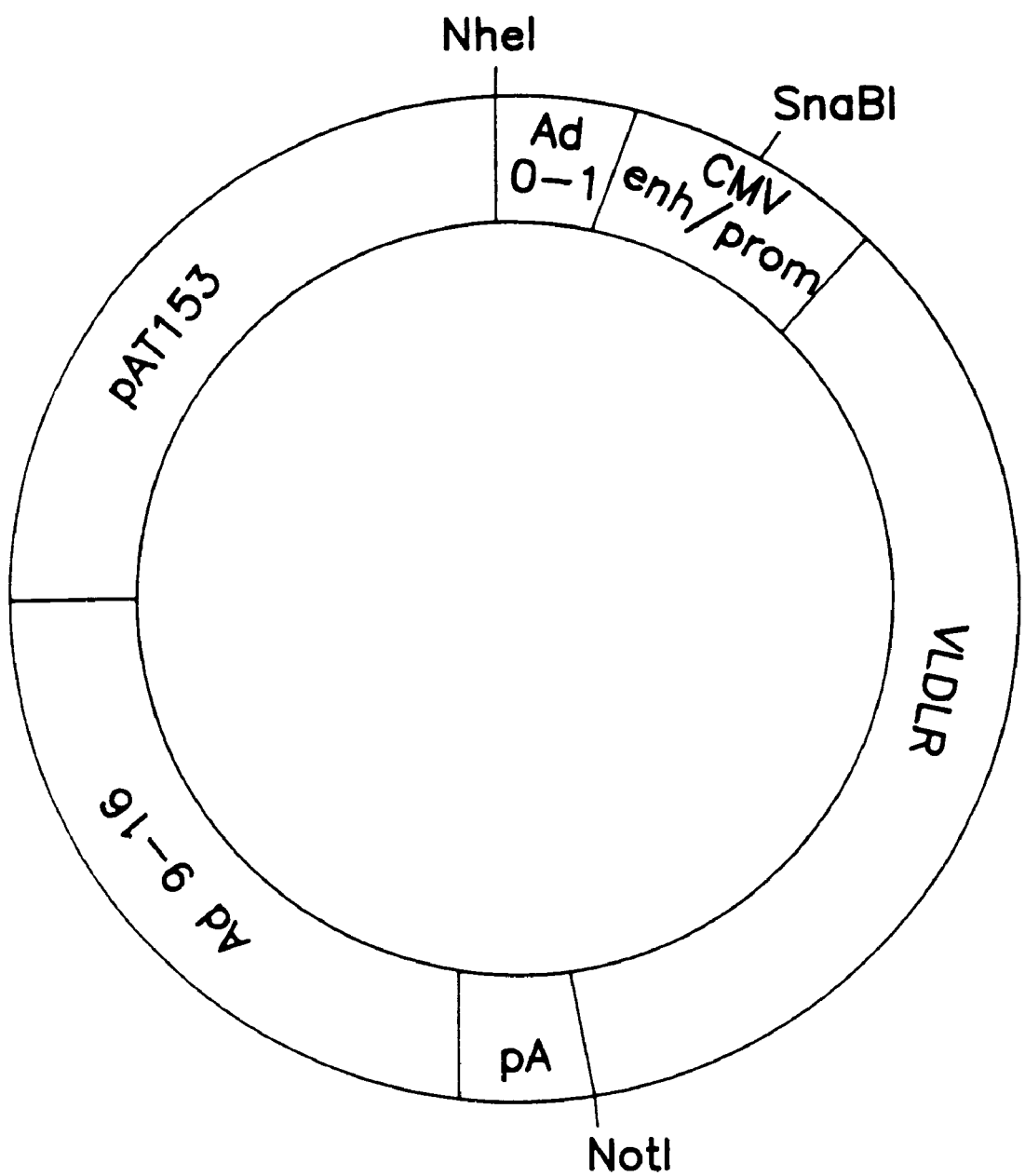
FIG. 2 is a schematic drawing of plasmid pAd.CMVVLDLR, which contains adenovirus map units 0–1 (Ad 0–1), followed by a cytomegalovirus enhancer/promoter (CMV enh/prom), a human VLDLR gene, a polyadenylation signal (pA), adenovirus map units 9–16 (Ad 9–16) and plasmid sequences from plasmid pAT153 including an origin of replication and ampicillin resistance gene. Restriction endonuclease enzymes are represented by conventional designations in the plasmid construct.

The plasmid pAd.CMVlacZ [Kozarsky II, cited above] was digested with SnaBI and NotI to remove the CMV promoter and lacZ cDNA and the 5.6 kb backbone was isolated. The two fragments were ligated to generate pAd.CMVVLDLR (FIGS. 2 and 9; SEQ ID NO: 3). pAd.CMVVLDLR was linearized with NheI and co-transfected into 293 cells with sub360 DNA (derived from adenovirus type 5) which had been digested with XbaI and ClaI as previously described [K. F. Kozarsky I and II cited above].

Figure 3:
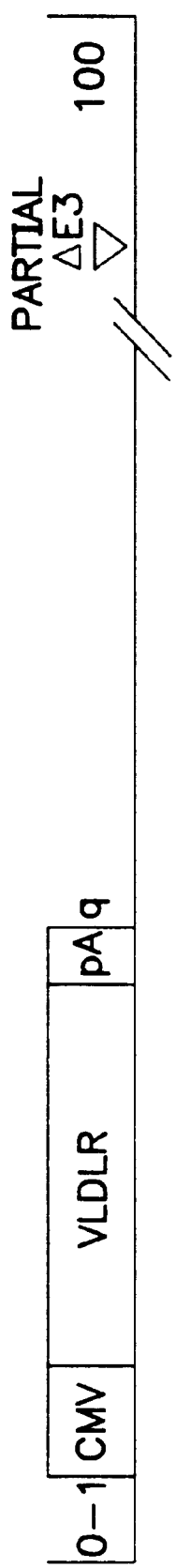
FIG. 3 is a schematic map of recombinant adenovirus H5.010CMVVLDLR, in which 0 to 100 represent the map units of an adenovirus type 5 (Genbank Accession No. M73260), and the CMV/VLDLR/pA minicassette of pAd.CMVVLDLR is inserted between adenovirus map units 1 and 9, with the remaining Ad5 map units 9–100 having a partial E3 gene deletion between about map unit 78.5 and about 84.3.

The resulting recombinant adenovirus, designated H5.010CMVVLDLR, contains the sequence from about nucleotide 12 to about 4390 of pAd.CMVVLDLR and Ad.5 map units 9–100 with a small deletion in the E3 gene (see GenBank Accession No. M73260 and discussion of FIG. 3). This recombinant adenovirus was isolated following two rounds of plaque purification. H5.010CMVVLDLR was grown on 293 cells and purified by two rounds of cesium chloride density centrifugation as previously described [K. F. Kozarsky I and II cited above]. Cesium chloride was removed by passing the virus over a BioRad 1ODG desalting column equilibrated with phosphate-buffered saline.

For rabbit experiments, virus was used freshly purified; for mouse experiments, virus was either used fresh, or after column purification glycerol was added to a final concentration of 10% (v/v), and virus was stored at −70° C. until use.

As described in the following examples, this recombinant adenovirus vector was introduced into the livers of WHHL rabbits and into the livers of LDL receptor knockout mice to determine the in vivo function of the VLDL receptor, and to determine its usefulness as an alternative or supplemental gene therapy for LDL receptor deficiency.

EXAMPLE 2

Other Recombinant Adenoviruses

H5.010CMVlacZ, encoding the lacZ gene under the control of the CMV enhancer/promoter, and H5.010CBhLDLR, encoding the human low density lipoprotein (LDL) receptor cDNA under the control of the CMV-enhanced chicken β-actin promoter, were prepared as previously described [K. F. Kozarsky I and II, cited above].

EXAMPLE 3

Effects of Hepatic Expression of the VLDL Receptor in the WHHL Rabbit

H5.010CMVVLDLR or H5.010CMVlacZ (encoding β-galactosidase), obtained as described in Examples 1 and 2, was infused intravenously into WHHL rabbits [Camm Research] as follows. Rabbits were infused with 7.5×10$^{12}$ particles of either recombinant adenovirus through a marginal ear vein on day 0. In addition, two New Zealand White (NZW) rabbits [Hazleton, Inc.] were infused with each virus and sacrificed on day 5 post-infusion to document the extent of gene transfer in the liver.

Rabbits were maintained in a 12 hour light/dark cycle on a diet of Purina laboratory chow, delivered each day at approximately 11:00 am. Venous samples were obtained through a marginal ear vein at approximately 10:00 am on the days indicated.

A. Plasma Analyses

Plasma samples were analyzed for total cholesterol using the Cholesterol HP kit and Precise standards (Boehringer Mannheim). Briefly, FPLC analysis was performed on 50 μl of plasma from individual mice adjusted to a volume of 250 μl in FPLC column buffer (1 mM EDTA, 154 mM NaCl, pH 8.0). Diluted samples (200 μl) were loaded onto two Superose 6 columns (Pharmacia) in series at a flow rate of 0.4 ml/min, and 1 ml fractions were collected. Cholesterol content was analyzed in a microplate assay on 100 μl samples. 100 μl of a freshly prepared solution containing 50 mM PIPES, pH 6.9, 7.8 g/L HDCBS, 0.51 g/L 4-AAT, 1.27 g/L cholic acid, 0.245% Triton X-100, 7.31 g/L KCl and supplemented with 1.22 U/ml cholesterol oxidase, 7.64 U/ml cholesterol esterase, and 245 U/ml peroxidase was added to samples, incubated overnight at room temperature, and the O.D. at 490 nm was determined.

Figure 4A:
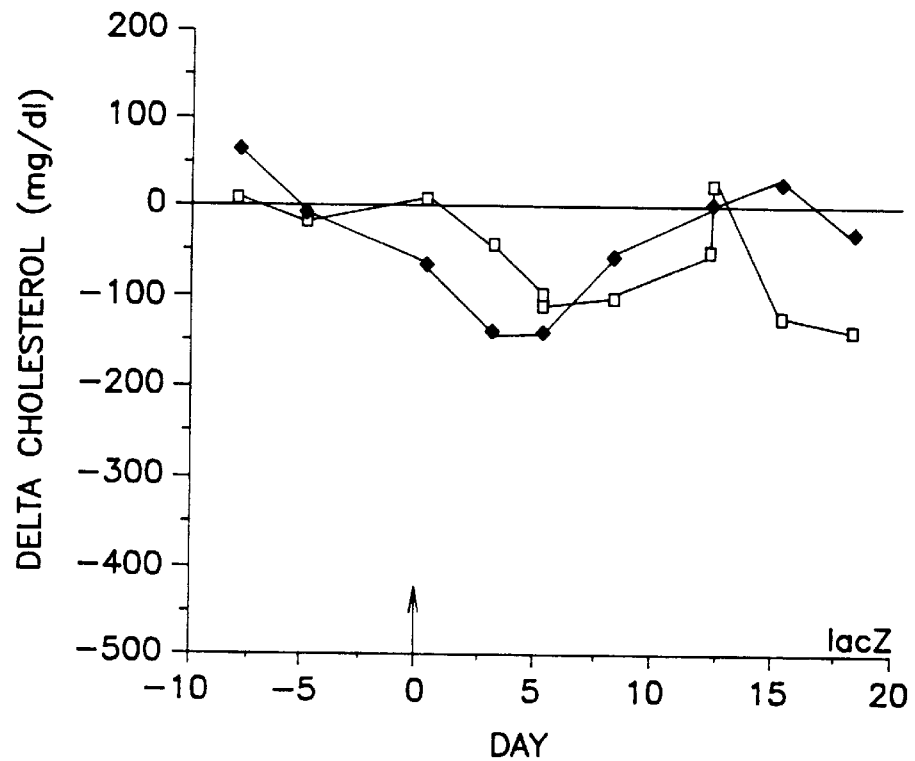
FIG. 4A is a graph plotting changes in plasma cholesterol levels in mg/dl for WHHL rabbits as a function of days before and after receiving recombinant adenovirus H5.010CMVlacZ. The symbols represent individual animals. See Example 3.
Figure 4B:
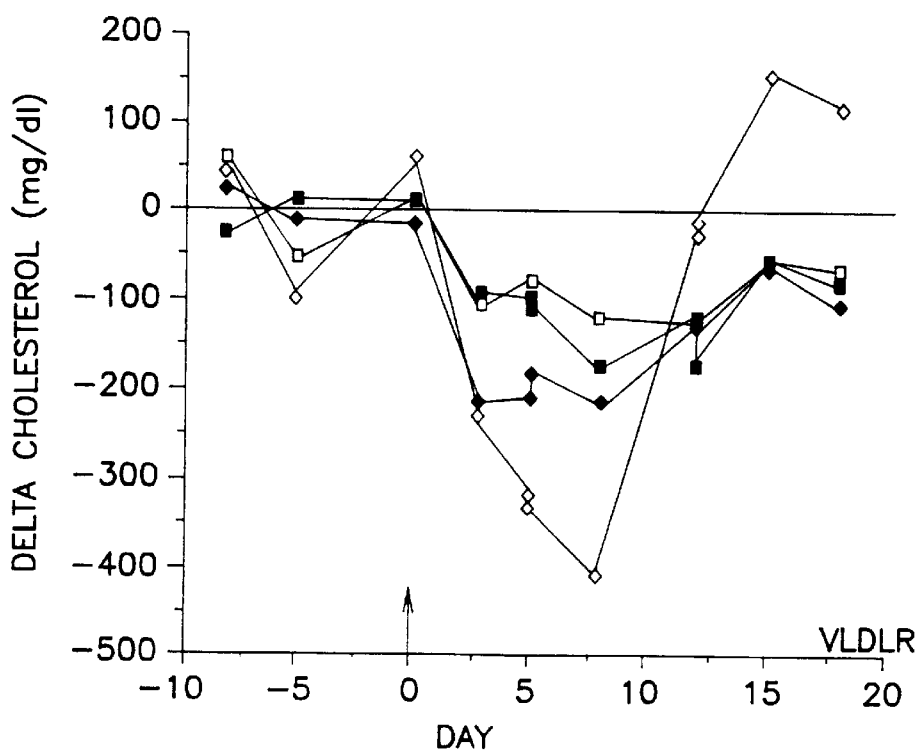
FIG. 4B is a graph plotting changes in plasma cholesterol levels in mg/dl for WHHL rabbits as a function of days before and after receiving recombinant adenovirus H5.010CMVVLDLR. The symbols represent the response of four individual animals. See Example 3.

Plasma cholesterol levels were evaluated in each of the WHHL rabbits before and after receiving recombinant adenovirus. FIG. 4A shows that rabbits infused with H5.010CMVlacZ had no significant changes in cholesterol levels. However, following infusion with H5.010CMVVLDLR, cholesterol levels dropped, with maximum decreases that ranged from 140 to 420 mg/dl (FIG. 4B). This demonstrated that expression of the VLDL receptor results in decreased cholesterol levels in LDL receptor-deficient rabbits.

B. Histochemical Analysis

Portions of liver were paraffin embedded, sectioned, and stained with hematoxylin and eosin. Some portions were fresh-frozen, sectioned, fixed in glutaraldehyde, stained with X-gal and lightly counterstained with hematoxylin. Some fresh-frozen sections were fixed in methanol, and then stained with either a polyclonal anti-o-galactosidase antibody (5 prime-3 prime), a polyclonal anti-human LDL receptor antibody, or with a polyclonal anti-VLDL receptor antibody, followed by a fluorescein isothiocyanate-conjugated anti-rabbit antibody (Jackson Immunoresearch) as previously described [K. F. Kozarsky I and II cited above]. Oil Red O staining was performed on fresh-frozen sections fixed for 1 minute in 37% formaldehyde, then rinsed and stained in Oil Red O (3 parts 0.5% Oil Red O in isopropyl alcohol/2 parts water) for 10 minutes. Slides were counterstained in hematoxylin and mounted in aqueous solution.

Immunofluorescence analysis of the infused rabbits showed that approximately 50% of hepatocytes from the rabbit infused with H5.010CMVlacZ expressed β-galactosidase, liver tissue from the rabbit infused with H5.010CMVVLDLR had a slightly higher percentage of hepatocytes expressing the VLDL receptor. In agreement with Northern blot analysis showing little or no VLDL receptor mRNA expression [M. E. Gafvels et al, cited above], liver from the lacZ-infused rabbit showed no reactivity with the anti-VLDL receptor antibody.

EXAMPLE 4

Effects of Short-Term Hepatic Expression of the VLDL Receptor in LDL Receptor Knockout Mice C57BL/6 mice and LDL receptor knockout mice (Jackson Labs) were infused intravenously with 0.5 or 1.0×10$^{10}$ particles of recombinant adenovirus through the tail vein and cholesterol levels were monitored before and after infusion.

Specifically, three mice each were infused with either H5.010CMVlacZ, H5.010CMVVLDLR, or H5.010CBhLDLR (encoding the human LDL receptor cDNA). This last virus was included as a control to confirm published results [Kozarsky I and II cited above]. Plasma samples were obtained by retro-orbital bleeds using heparinized capillary tubes. The LDL receptor knockout mice were maintained upon a high cholesterol diet composed of Purina mouse chow supplemented with 1.25% cholesterol, 7.5% cocoa butter, 7.5% casein, and 0.5% cholate (1.25% cholesterol diet) for at least 3 weeks immediately following weaning before experiments were initiated. Mice were sacrificed on day 5 post-infusion.

Liver tissues were analyzed by immunofluorescence for transgene expression by the techniques described in Example 3, and plasma cholesterol levels were measured as similarly described. For lipoprotein fractionations, plasma from triplicate LDL receptor knockout mice were pooled, subjected to density ultracentrifugation, fractions were collected, and the cholesterol content was determined by conventional means.

Immunofluorescence analysis revealed moderate levels of β-galactosidase expression in H5.010CMVlacZ-infused mice, and higher levels of either human LDL receptor and VLDL receptor expression in H5.010CBhLDLR-and in H5.010CMVVLDLR-infused mice, respectively.

Figure 5:
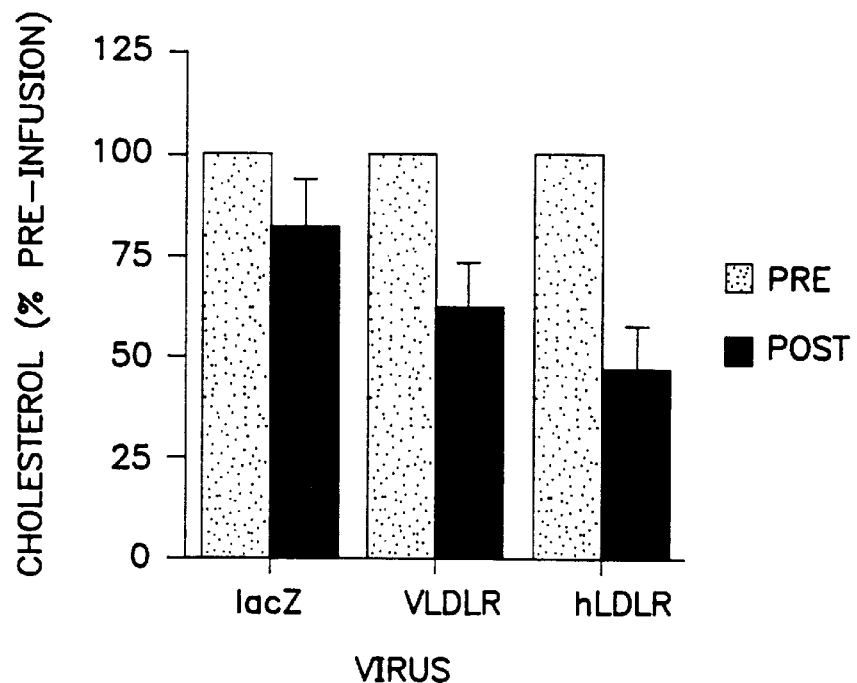
FIG. 5 is a bar graph representing cholesterol levels (measured as % pre-infusion) in mice infused with recombinant adenovirus H5.010CMVlacZ (lacZ), recombinant adenovirus H5.010CMVVLDLR and recombinant adenovirus H5.010CBhLDLR. The dotted bars represent pre-infusion levels and the solid bars represent post-infusion levels. See Example 4.
Figure 6:
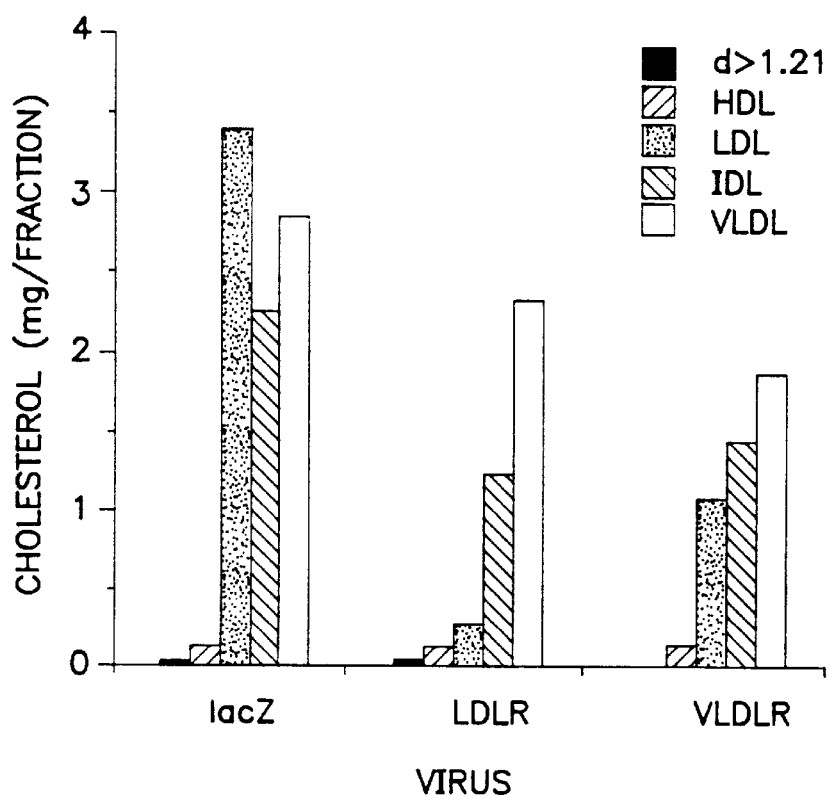
FIG. 6 is a bar graph representing cholesterol levels, specifically the levels of the fractions of plasma lipoproteins (measured as mg/fraction) in mice infused with recombinant adenovirus H5.010CMVlacZ (lacZ), recombinant adenovirus H5.010CMVVLDLR and recombinant adenovirus H5.010CBhLDLR. The solid bars represent proteins or fragments falling within a density (d) >1.21; the thickly cross-hatched bars represent HDL; the closely cross-hatched bars represent LDL, the spaced apart slanted hatched bars represent intermediate density lipoprotein (IDL), and the clear bars represent VLDL levels. See Example 4.

Cholesterol levels decreased slightly in the control, H5.010CMVlacZ-infused mice (FIG. 5), probably due to non-transgene-related effects of infusion of recombinant adenovirus, which can result in hepatotoxicity in mice [Y. Yang et al, *Proc. Natl. Acad. Sci., USA*, 91:4407–4411 (May 1994)]. However, in contrast to the decrease observed in the control mice, cholesterol levels dropped significantly to 50% of pre-infusion values in the H5.010CBhLDLR-infused mice on day 5 post-infusion. Cholesterol levels in the H5.010CMVVLDLR-infused mice also decreased, to approximately 60% of pre-infusion levels. Further analysis of plasma lipoproteins showed that in the H5.010CBhLDLR-treated mice, LDL levels plummeted, with additional decreases in IDL and VLDL fractions (FIG. 6). The H5.010CMVVLDLR-infused mice showed a larger decrease in the VLDL fraction with less of a decrease in LDL.

Taken together, these data indicate that hepatic expression of VLDL receptor results in increased clearance of VLDL from the plasma, resulting in decreases in the amounts of lipoproteins for which VLDL is the precursor (i.e., IDL and LDL), and an overall drop in total plasma cholesterol.

EXAMPLE 5

Effects of Long-Term Hepatic Expression of the VLDL Receptor in LDL Receptor Knockout Mice In order to achieve cholesterol levels closer to those observed in both FH patients and WHHL rabbits, LDL receptor knockout mice (Jackson Labs) were maintained on a high cholesterol diet composed of Purina mouse chow supplemented with 0.2% cholesterol, 10% coconut oil, and 0.05% cholate (0.2% cholesterol diet). Cholesterol levels in these mice ranged from 930 to 1550 mg/dl, whereas the mice on the 1.25% cholesterol (Example 4) diet had levels of 1900 to 3100 mg/dl.

Virus was thawed immediately before use and diluted with PBS to a concentration of $1\times10^{12}$ particles/ml. Three mice were each infused intravenously with 0.1 ml of virus containing $1\times10^{11}$ particles of an E1-deleted recombinant adenovirus encoding either β-galactosidase (H5.010CMVlacZ) or human LDL receptor (H5.010CBhLDLR), and serum lipids were followed over time. On the days indicated, mice were anesthetized with methoxyflurane and blood was collected into heparinized capillary tubes by puncture of the retro-orbital venous plexus.

Immunofluorescence staining showed that most of the hepatocytes expressed the transgene product, either β-galactosidase, human LDL receptor, or VLDL receptor. Hematoxylin and eosin staining of sections of liver revealed essentially normal morphology in the H5.010CMVlacZ-infused mouse. However, for both the H5.010CBhLDLR- and H5.010CMVVLDLR-infused mice, hepatocytes appeared to have internal vacuoles. When tissue was analyzed with Oil Red O staining, a stain for neutral lipids, liver from the receptor-infused animals clearly showed accumulation of large droplets of lipid when compared with the H5.010CMVlacZ-infused control. This suggested that short-term, high level expression of the LDL receptor or VLDL receptor in these LDL receptor-deficient mice resulted in intracellular accumulation of lipids.

Figure 7A:
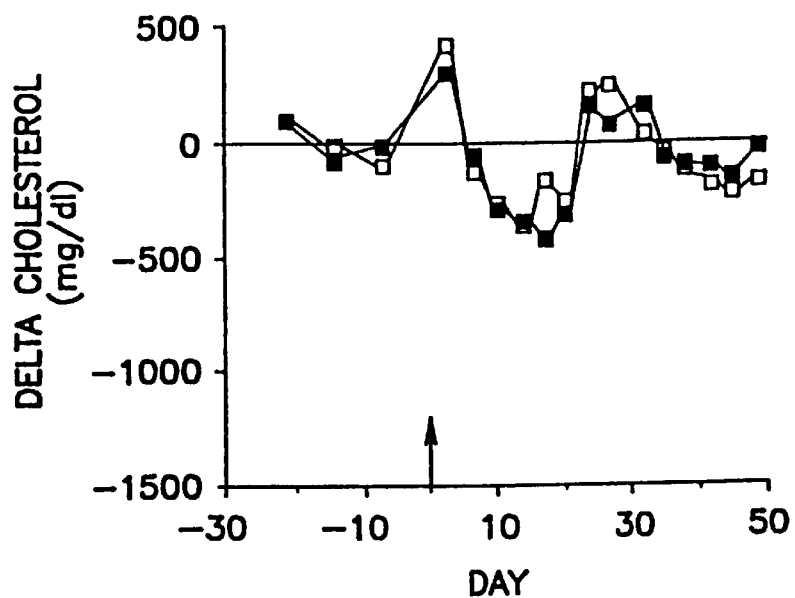
FIG. 7A is a graph plotting changes in cholesterol levels (measured in mg/dl) as a function of days pre- and post-infusion for LDL receptor knock out mice infused with H5.010CMVlacZ. The symbols represent the responses of individual animals. See Example 5.
Figure 7B:
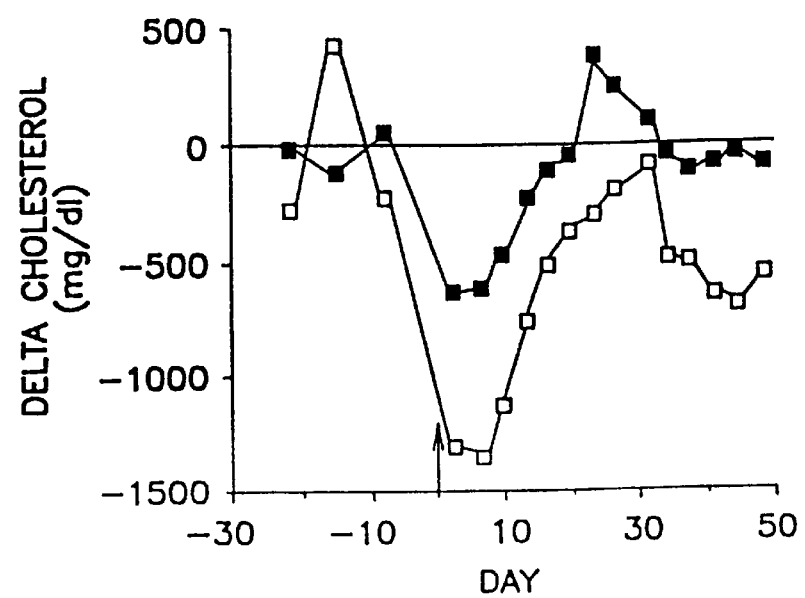
FIG. 7B is a graph plotting changes in cholesterol levels (measured in mg/dl) as a function of days pre- and post-infusion for LDL receptor knock out mice infused with H5.010CBhLDLR. The symbols are the same as for FIG. 7A. See Example 5.
Figure 7C:
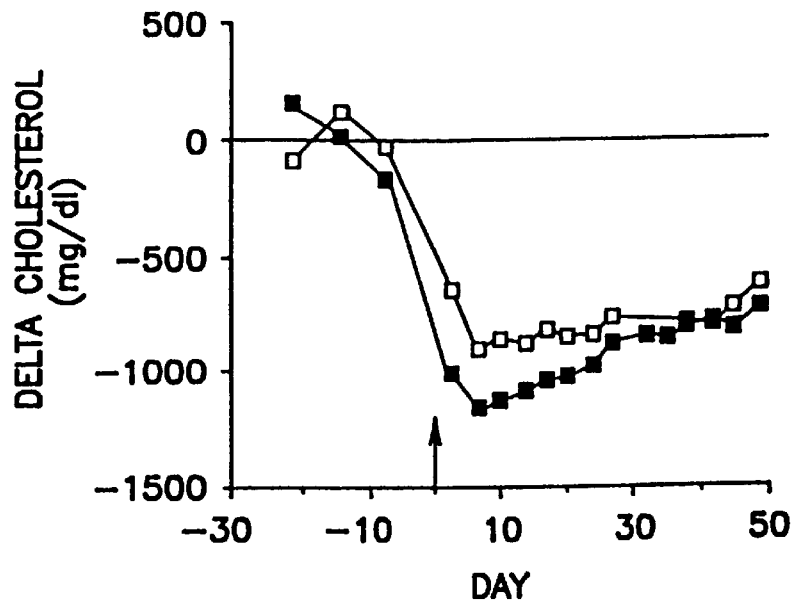
FIG. 7C is a graph plotting changes in cholesterol levels (measured in mg/dl) vs. days pre and post-infusion for LDL receptor knock out mice infused with H5.010CMVVLDLR. The symbols are the same as for FIG. 7A. See Example 5.
Figure 7D:
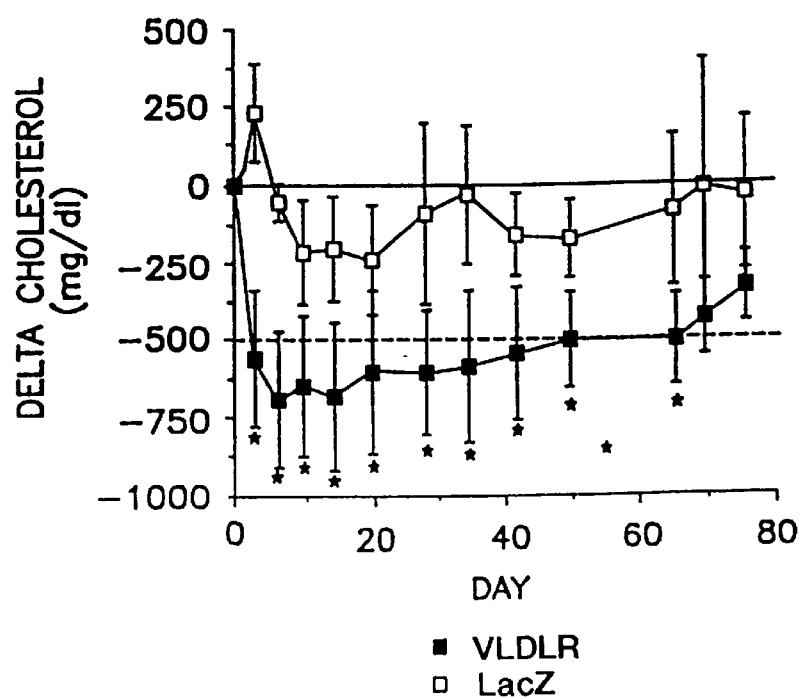
FIG. 7D is a graph providing the average results ± standard deviation from two experiments for mice infused with H5.010CMVLacZ (n=9) or with H5.010CMVVLDLR (n=10). Average pre-infusion cholesterol levels were 870 mg/dl and 946 mg/dl, respectively. Asterisks indicate p<0.05.

To confirm the biological activities of the transgene products, plasma cholesterol levels were followed before and after recombinant adenovirus administration. FIG. 7A shows that serum cholesterol levels in H5.010CMVlacZ-infused mice demonstrated a characteristic but not significant fluctuation over time, reflected in minor changes of all lipoprotein fractions (HDL, IDL/VLDL, and LDL). In contrast, mice infused with H5.010CBhLDLR have a large but transient decrease in cholesterol (see, FIG. 7B). Particularly, these mice demonstrated large plasma cholesterol decreases which lasted for approximately 2 weeks. Cholesterol levels decreased 3-fold (from 966 to 353 mg/dl) and 7-fold (from 1554 to 219 mg/dl) and returned to baseline by 3 weeks post-infusion. The decrease in serum cholesterol is reflected in coordinate diminution in serum LDL. This nonspecific effect of the adenovirus infection when immune modulators are not coordinately administered has been described previously and is likely due to changes in hepatic function that occur as a result of the associated inflammation. Mice infused with H5.010CMVVLDLR showed large decreases in plasma cholesterol (FIG. 1C) which were similar in magnitude to those seen in the H5.010CBhLDLR-infused mice (FIG. 7B), with maximum decreases of more than 4-fold (from 1186 to 288 mg/dl and from 1453 to 299 mg/dl). surprisingly, plasma cholesterol levels did not return to baseline by 3 weeks post-infusion. The change in plasma cholesterol levels in the H5.010CMVVLDLR-infused mice (FIG. 7D) were statistically significant (p<0.05) through 9 weeks following infusion (the current duration of the experiment).

Sera from individual mice was analyzed by FPLC to determine the effects of VLDL receptor expression on lipoprotein fractions. On day 3 post-infusion, VLDL and LDL fractions were undetectable; over time, the LDL fraction slowly recovered, although even at 10 weeks post-infusion, the LDL peak height was slightly lower than the HDL peak height. VLDL remained undetectable although minor differences may escape detection because of limitations in the sensitivity of the cholesterol assay. The LDL peaks mirrored the total plasma cholesterol levels, and confirmed that the prolonged lowering of plasma cholesterol was accompanied by sustained decreases in VLDL and LDL levels. These data suggest that expression of the VLDL receptor in the liver is an effective therapy for hypercholesterolemia.

At the same time of infusion of the LDL receptor knockout mice, normal C57Bl/6 mice were infused with each of the recombinant adenoviruses. These mice were sacrificed at various times post-infusion, and liver tissues were harvested for direct analysis of transgene expression using X-gal histochemistry to detect β-galactosidase expression and immunofluorescence performed to measure LDL receptor expression. Tissues harvested three days after infusion of virus demonstrated either expression of β-galactosidase or the human LDL receptor in at least 80% of hepatocytes.

In each experiment, the vector specific signal was substantially higher than that seen in animals before gene transfer or following infusion with identical quantities of an adenovirus expressing an irrelevant gene. For both lacZ and LDL receptor, transgene expression diminished to undetectable levels by day 21 and was associated with the development of a self limited mononuclear infiltrate in liver that peaked at day 10. The infiltrate consisted of portal as well as lobular inflammation, accompanied by the presence of apoptic bodies. The extent of pathology was indistinguishable between the lacZ and LDL receptor infused mice. The time course of LDL receptor expression is consistent with the initial large decline in plasma cholesterol and subsequent return to baseline.

In contrast, two mice infused with H5.010CMVVLDLR expressed the VLDL receptor at high levels. The percent of hepatocytes may have decreased slightly as compared to the day 5 mice. These data suggest that the sustained decrease in plasma cholesterol levels in the H5.010CMVVLDLR-infused mice was due to sustained expression of the VLDL receptor.

EXAMPLE 6

Turnover Studies

To further characterize the effects of hepatic VLDL receptor expression on lipoprotein metabolism, turnover studies were performed as follows.

LDL receptor knockout mice were infused with recombinant adenovirus after 3 weeks on the high cholesterol diet as described in Example 4. Three mice each were injected with the lacZ and VLDL receptor adenoviruses; one mouse was injected with the LDL receptor adenovirus. On day 5 post-infusion, mice were injected via the tail vein with approximately $8 \times 10^6$ cpm of $^{125}$I-labeled human LDL, and $1.6 \times 10^5$ cpm of $^{131}$I-labeled human VLDL in a total volume of 0.2 ml. A blood sample was obtained 1 minute following injection of radiolabel, and designated the "time zero" sample. Blood was collected into heparinized capillary tubes at the indicated times, and radioactivity remaining was determined using a gamma counter.

Infusion of LDL receptor adenovirus led to accelerated clearance of LDL as compared to infusion of lacZ adenovirus, consistent with a previous study in LDL receptor knockout mice [S. Ishibashi et al, *J. Clin. Invest.*, 92:883–893(1993)]. Similarly, VLDL clearance was accelerated in LDL receptor treated animals as compared to lacZ infused mice. LDL turnover in VLDL receptor-infused mice was indistinguishable from lacz infused mice, consistent with in vitro data which indicates that LDL is not a ligand for the VLDL receptor [T. Yamamoto et al, Trends in *Cardiovascular Medicine*, 3:144–148 (1993); F. Batley et al, *J. Biol. Chem.*, 269:23268–23273 (1994)]. VLDL clearance in VLDL receptor infused mice was slightly faster than n lacZ infused mice, but significantly slower than in LDL receptor infused mice.

As discussed above, VLDL turnover in mice infused with the VLDL receptor adenovirus was significantly faster than in lacZ infused mice although the magnitude of this effect was far less than that seen in animals treated with LDL receptor virus. This suggests that VLDL receptor-mediated clearance of circulating VLDL may not be the only pathway leading to diminished serum VLDL. One potential mechanism is secretion-recapture, which occurs with hepatic uptake of chylomicron remnants [T. Willnow & J. Herz, *J. Mol. Med.*, 73:213–220 (1995); H. Shimano et al, *J. Clin. Invest.*, 93:2215–2223 (1994)], and would result in decreased secretion of VLDL and reduced levels of plasma VLDL. A second mechanism may involve the interaction of the VLDL receptor with receptor-associated protein (RAP) [Battey, cited above; H. Mokuno et al, *J. Biol. Chem.*, 269:13238–13243 (1994)] which interacts with a variety of receptors inside the cell, apparently to prevent ligand binding before the receptor reaches the cell surface [G. Bu et al, *EMBO J*, 14:2269–2280 (1995)]. It is possible that the high levels of VLDL receptor expressed in the livers of adenovirus-infused mice overwhelms the available RAP, so that VLDL receptor is binding to newly synthesized ligand (apoE, either free or in association with lipid) within the cell, and preventing its secretion into the plasma. The effects of hepatic VLDL receptor expression on total plasma cholesterol as well as on lipoprotein cholesterol levels demonstrate that the VLDL receptor can play a major role in lipoprotein metabolism in vivo.

EXAMPLE 7

Stability of Expression of VLDL Receptor

This experiment illustrates relative transgene persistence in mice.

LDL receptor knockout mice were injected intravenously on day 0 with $1 \times 10^{11}$ particles of H5.010CMVlacZ, H5.010CBhLDLR, or H5.010CMVVLDLR. Mice were sacrificed on the indicated days after injection (3, 10 or 21), and fresh-frozen sections of liver were stained with X-gal to detect expression of the lacZ gene, and with anti-LDL receptor antibody or anti-VLDL receptor antibody, followed by a fluorescein-conjugated secondary antibody to detect LDL receptor and VLDL receptor, respectively.

Analysis of liver harvested 3 days after infusion of virus revealed VLDL receptor protein in >80% of hepatocytes; the bright fluorescent signal, which localized to the perimeter of the cell, was absent before gene transfer and in tissues of animals infected with lacZ or LDL receptor containing adenoviruses. Expression of VLDL receptor protein was remarkably stable with recombinant protein detected in approximately 5 to 10% of hepatocytes from tissue harvested 105 days after infusion of virus. This is in striking contrast to the results obtained with lacZ and LDL receptor adenovirus, where expression of the transgene extinguished to undetectable levels within three weeks of gene transfer. VLDL receptor expression remained detectable through the duration of the experiment (22 weeks).

Genomic DNA was isolated from mouse liver, digested with EcoRI, and subjected to Southern blotting [K. Kozarsky et al. *J. Biol. Chem.*, 269:13695–13702 (1994)] to monitor the presence over time of adenoviral DNA sequences. Adenovirus sequences were detected using the Genius kit from Boehringer Mannheim, followed by chemiluminescent detection. In C57BL/6 mice infused with the lacZ adenovirus, viral DNA diminished rapidly with time, plateauing at barely detectable levels (~0.05 copies/cell) through day 70 post-infusion. Mice infused with VLDL receptor had slightly higher initial levels of DNA, but a similar time course of loss of adenovirus sequences. Additional DNA hybridization studies showed that the majority of adenovirus DNA initially delivered to the liver is not integrated into the mouse genome (data not shown), however, this assay cannot rule out some level of integration.

Histopathologic analysis of liver tissue from mice infused with the VLDL receptor virus revealed inflammation and apoptotic cells at early time points. The timing and extent of the pathologic findings were indistinguishable from liver tissues of mice infused with lacZ and LDL receptor viruses. At 15 and 22 weeks post-infusion, however, liver tissue from VLDL receptor-infused mice displayed discernible accumulations of neutral lipids, as demonstrated by hematoxylin and eosin as well as oil red O staining. Similar changes were observed infrequently in LDL receptor knockout mice infused with PBS, LDL receptor and/or lacZ adenoviruses. No lipid accumulations were observed in livers of normal C57BL/6 mice infused with the VLDL receptor virus, despite long-term transgene expression indistinguishable from that observed in LDL receptor knockout mice. This indicates that VLDL receptor expression alone is not sufficient for the changes in lipid accumulation observed in LDL receptor knockout mice; instead, there is some lipid accumulation in the LDL receptor knockout mice which have been maintained on a high cholesterol diet for ≧18 weeks, that is accelerated by prolonged VLDL receptor expression.

Plasma samples from mice infused with VLDL receptor adenovirus were analyzed for the presence of antibodies directed against the VLDL receptor protein. Only one mouse out of twelve generated antibodies to the VLDL receptor despite the presence of high level antibodies to adenovirus capsid proteins in each animal that received virus. Animals infused with the VLDL receptor adenovirus mounted a CTL response to adenoviral proteins indistinguishable from that obtained from animals infused with either lacZ or LDL receptor adenoviruses. These mice, however, did not mount a CTL response to the VLDL receptor protein. Thus, the development of a CTL response to the transgene following infusion of recombinant adenovirus is dependent on the antigenicity of the specific transgene in the treated animal.

EXAMPLE 8

Humoral and Cellular Immune Response to Adenovirus and Transgenes

A. Humoral Immune Response

Two LDL receptor knockout mice (K020 and K027) or two normal C57BL/6 mice were injected via the tail vein with $1\times10^{11}$ particles of H5.010CBhLDLR at day O and serum samples were collected both before injection (pre), and on days 10, 24, 39, 52 and 70 following injection for the knockout mice and on day 21 for the C57BL/6 mice. Western blots were performed as previously described [K. Kozarsky et al, *J. Biol. Chem.*, 269:13695–13702 (1994); K. Kozarsky et al., *Som. Cell and Molec. Genet.*, 19:449–458 (1993)]. To detect anti-adenovirus antibodies, purified adenovirus was used as the antigen. The positive control (+) was rabbit antiserum isolated following intravenous infusion of purified H5.010CBhLDLR. The negative control (−) was pre-immune rabbit serum. Western blots with β-galactosidase were performed using purified protein (Sigma), with a monoclonal antibody specific for β-galactosidase (Sigma) as a positive control.

Antibodies directed against the human LDL receptor were detected using lysates prepared from 24–23 cells, a 3T3 cell line which was transduced with retrovirus encoding the human LDL receptor. For detection of anti-VLDL receptor antibodies, a lysate was prepared from HeLa cells two days following infection with H5.010 CMVVLDLR.

All mice infused with $1\times10^{11}$ particles of recombinant adenovirus developed antibodies to adenovirus capsid proteins, with major bands corresponding to hexon, penton and fiber. All mice infused with H5.010CBhLDLR developed antibodies to the human LDL receptor protein with LDL receptor knockout mice consistently developing higher titer antibodies that C57BL/6 mice. Antibodies from LDL receptor knockout mice cross-reacted with mouse LDL receptor protein, whereas antibodies from C57BL/6 mice (which express normal mouse LDL receptor) did not.

This suggests that the VLDL receptor, although the human and not the mouse sequence was used, was not immunogenic in these mice. The amino acid sequences of the human and mouse LDL receptors are approximately 78% identical, while the human and mouse VLDL receptors are >94% identical. This increased sequence similarity is likely to account for the absence of antibody development to the human VLDL receptor despite high level expression in the mouse liver as a result of infusion of H5.010CMVVLDLR.

These data demonstrate that animals can generate a humoral immune response specific for the transgene product as well as to the viral proteins encoded on the injected adenovirus. It also provides indirect evidence of antigen specific activation of T helper cells, which is normally required for development of mature, antibody-secreting B cells.

B. Cellular Immune Responses

This study analyzed animals following infusion with the LDL receptor adenovirus for activation of CTLs to both viral antigens and the transgene product, human LDL receptor.

CTL assays were performed as described in Y. Yang et al, *Immunity*, 1:433–442 (1994). Target cells expressing recombinant vaccinia proteins were generated by infecting with recombinant vaccinia were generated as follows. The VLDV receptor cDNA (in the pRC/CMV plasmid) was subcloned into the HindIII site of Bluescript KS+. The CFTR cDNA [J. R. Riordan et al, *Science*, 245:1066–1073 (1989) was cloned into the PstI site of Bluescript KS+ (Stratagene). The LDL receptor cDNA in the pUC19 vector [T. Yamamoto et al, *Cell*, 39:27–38 (1984)] was excised with the restriction enzymes HindIII and Sac 1 and ligated into the HindIII and SacI sites of Bluescript KS+. Each of the cDNAs was then excised using the enzymes SacII and KpnI and cloned into the SacII and Kpnl sites of a modified form of the vaccinia expression vector pSC11 [S. Chakrabarti et al, *Molec. Cell. Biol.*, 5:3403–3409 (1985)]. The control recombinant vaccinia, VRG, expresses a rabies virus glycoprotein and was prepared as described in T. Wiktor et al, *Proc. Natl. Acad. Sci. USA*, 81: 7194–7198 (1984).

Figure 10A:
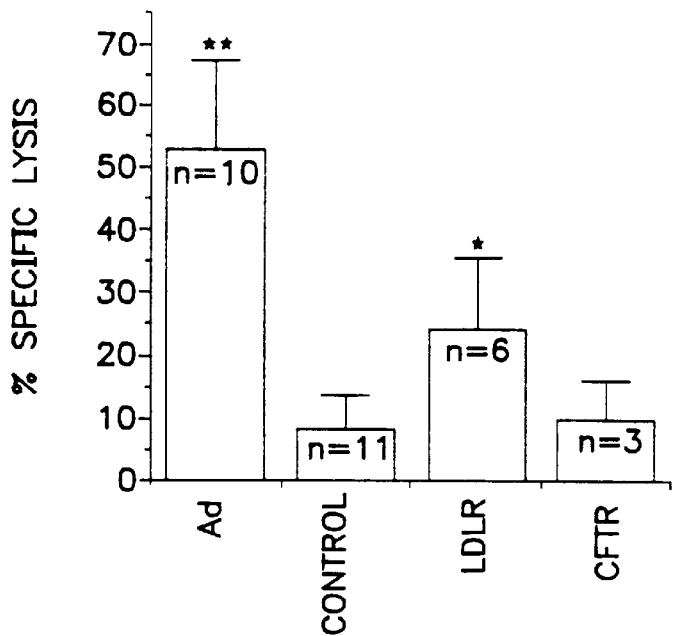
FIG. 10A is a bar chart illustrating the CTL activity (average ± standard deviation) measured at an effector:target cell ratio of 25:1. **=p<0.005; *=p<0.05.
Figure 10B:
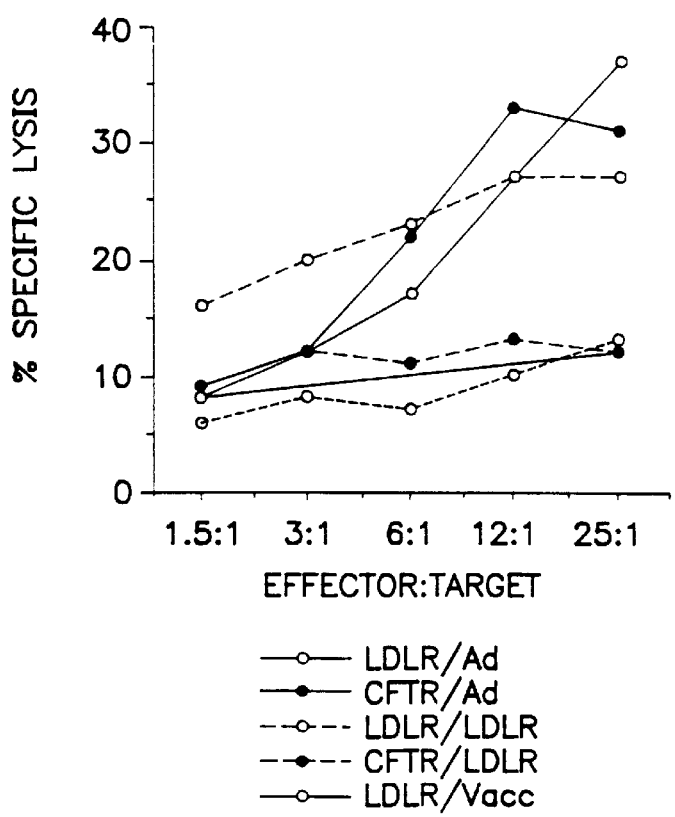
FIG. 10B is a line graph illustrating the CTL activity measured against varying effector:target ratios.

CTLs to specific targets were detected in a standard $^{51}$chromium ($^{51}$Cr) release assay in which MHC compatible target cells were infected with either recombinant adenovirus or vaccinia viruses that express single relevant gene products. FIG. 10 presents both an example of a $^{51}$Cr release assay in which % specific lysis is measured as a function of increasing the effector to target ratio (FIG. 10B), as well as a summary of the cumulative data (FIG. 10A). Splenocytes from C57BL/6 mice infused with recombinant adenovirus containing either human LDL receptor or human CFTR were evaluated for their ability to lyse targets infected with either recombinant adenovirus, to measure activity to viral proteins, or with vaccinia virus containing LDL receptor, to measure activity to LDL receptor protein. Cytolytic activity was demonstrated with lymphocytes from animals infected with the LDL receptor virus to target cells infected with the same virus. No cytolysis was detected to mock infected targets supporting the specificity of the assay. These same effector cells demonstrated significant cytolytic activity to targets infected with LDL receptor vaccinia virus that was not present when-infected with a control vaccinia. These experiments provide strong evidence for the presence of activated CTL to human LDL receptor in C57BL/6 mice following gene therapy.

EXAMPLE 9

Enhancement of Adenovirus Mediated Gene Transfer upon Second Administration by IL-12 and IFN-τ in Mouse Lung The recombinant adenoviruses H5.010CMVlacZ and H5.010CBALP (alkaline phosphatase gene expressed from the CMV enhanced B-actin promoter in the sub360 backbone) were used in this example. Each similar virus expresses a different reporter gene whose expression can be discriminated from that of the first reporter gene.

Female C57Bl/6 mice (6~8 week old) were infected with suspensions of H5.010CBALP ($1\times10^9$ pfu in 50 µl of PBS) via the trachea at day 0 and similarly with H5.010CMVlacZ at day 28. One group of such mice was used as a control. Another group of mice were acutely depleted of $CD4^+$ cells by i.p. injection of antibody to $CD4^+$ cells (GK1.5; ATCC No. TIB207, 1:10 dilution of ascites) at the time of the initial gene therapy (days −3, 0, and +3). A third group of mice were injected with IL-12 (1 µg intratracheal or 2 µg, i.p. injections) at the time of the first administration of virus (days 0 and +1). A fourth group of mice were injected with gamma interferon (1 µg intratracheal or 2 µg, i.p. injections) at the time of the first administration of virus (days 0 and +1).

When mice were subsequently euthanized and necropsied at days 3, 28, or 31, lung tissues were prepared for cryosections, while bronchial alveolar lavage (BAL) and mediastinal lymph nodes (MLN) were harvested for immunological assays.

A. Cryosections

The lung tissues were evaluated for alkaline phosphatase expression by histochemical staining following the procedures of Y. Yang et al, cited above.

Instillation of alkaline phosphatase virus ($10^9$ pfu) into the airway of all groups of the C57Bl/6 mice resulted in high level transgene expression in the majority of conducting airways that diminishes to undetectable levels by day 28. Loss of transgene expression was shown to be due to CTL mediated elimination of the genetically modified hepatocytes [Y. Yang et al, cited above].

In the control mice, no recombinant gene expression was detected three days after the second administration of virus, i.e., day 31.

Administration of virus to the $CD4^+$ depleted animals was associated with high level recombinant transgene expression that was stable for a month. Expression of the second virus was detectable on day 31.

Initial high level gene transfer diminished after about one month in the IL-12 treated mice; however, in contrast to the control, high level gene transfer to airway epithelial cells was achieved when virus was readministered to IL-12 treated animals at day 28, as seen in the day 31 results.

The gamma-interferon treated animals were virtually indistinguishable from the animals treated with IL-12 in that efficient gene transfer was accomplished upon a second administration of virus.

B. Immunological Assays—MLN

Lymphocytes from MLN of the control group and IL-12 treated group of C57Bl/6 mice harvested 28 days after administration of H5.010CBALP were restimulated in vitro with UV-inactivated H5.010CMVlacZ at 10 particles/cell for 24 hours. Cell-free supernatants were assayed for the presence of IL-2 or IL-4 on HT-2 cells (an IL-2 or IL-4-dependent cell line) [Y. Yang et al, cited above]. Presence of IFN-γ in the same lymphocyte culture supernatant was measured on L929 cells as described [Y. Yang et al, cited above]. Stimulation index (S.I.) was calculated by dividing $^3$H-thymidine cpm incorporated into HT-2 cells cultured in supernatants of lymphocytes restimulated with virus by those incorporated into HT-2 cells cultured in supernatants of lymphocytes incubated in antigen-free medium.

The results are shown in Table 1 below.

TABLE 1

|  | $^3$H-Thymidine Incorporation (cpm ± SD) | | | IFN-γ liter |
|---|---|---|---|---|
|  | Medium | H5.010CMVlacZ | S.I. | $(IU/ml)^d$ |
| C57Bl/6 | 175 ± 40 | 2084 ± 66 | 11.91 | 80 |
| anti-IL2 (1:5000) | 523 ± 81 | 2.98 | | |
| anti-IL4 (1:5000) | 1545 ± 33 | 8.83 | | |
| C57Bl/6 + IL12 | 247 ± 34 | 5203 ± 28 | 21.07 | 160 |
| anti-IL2 (1:5000) | 776 ± 50 | 3.14 | | |
| anti-IL4 (1:5000) | 4608 ± 52 | 18.66 | | |

Stimulation of lymphocytes from regional lymph nodes with both recombinant adenoviruses led to secretion of cytokines specific for the activation of both $T_{H1}$ (i.e., IL-2 and IFN-γ) and $T_{H2}$ (i.e., IL-4) subsets of T helper cells (Table 1).

Analysis of lymphocytes from the IL-12 treated animals stimulated in vitro with virus revealed an increased secretion of IL-2 and IFN-γ and a relative decreased production of IL-4 as compared to animals that did not receive IL-12 (i.e., ratio of IL-2/IL-4 was increased from 3 to 6 when IL-12 was used; Table 1).

C. Immunological Assays—BAL

BAL samples obtained from animals 28 days after primary exposure to recombinant virus were evaluated for neutralizing antibodies to adenovirus and anti-adenovirus antibody isotypes as follows. The same four groups of C57Bl/6 mice, i.e., control, $CD4^+$ depleted, IL-12 treated and IFN-γ treated, were infected with H5.010CBALP. Neutralizing antibody was measured in serially diluted BAL samples (100 µl) which were mixed with H5.010CMVlacZ ($1\times10^6$ pfu in 20 µl), incubated for 1 hour at 37° C., and applied to 80% confluent Hela cells in 96 well plates ($2\times10^4$ cells per well). After 60 minutes of incubation at 37° C., 100 µl of DMEM containing 20% FBS was added to each well. Cells were fixed and stained for β-galactosidase expression the following day.

All cells were lacZ positive in the absence of anti-adenoviral antibodies.

Adenovirus-specific antibody isotype was determined in BAL by using enzyme-linked immunosorbent assay (ELISA). Briefly, 96-well plates were coated with 100 µl of PBS containing $5\times10^9$ particles of H5.010CMVlacZ for 18 hours at 4° C. The wells were washed 5 times with PBS. After blocking with 200 µl of 2% BSA in PBS, the plates were rinsed once with PBS and incubated with 1:10 diluted BAL samples for 90 minutes at 4° C. Thereafter, the wells were extensively washed and refilled with 100 µl of 1:1000 diluted alkaline phosphatase-conjugated anti-mouse IgG or IgA (Sigma). The plates were incubated, subsequently washed 5 times, and 100 µl of the substrate solution (p-nitrophenyl phosphate, PNPP) was added to each well.

Substrate conversion was stopped by the addition of 50 μl of 0.1M EDTA. Plates were read at 405 nm.

Figure 11A:
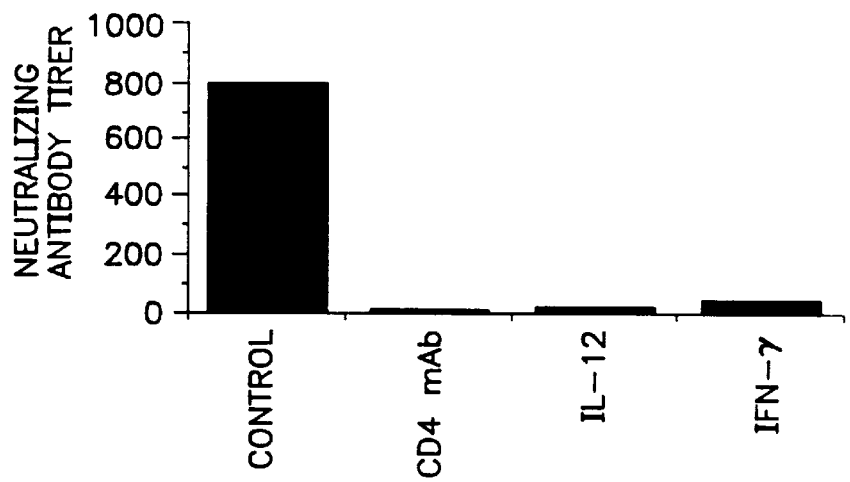
FIG. 11A is a graph summarizing neutralizing antibody titer present in BAL samples of C57BL/6 mice adenovirus-infected on day 0 and necrotized on day 28 as described in Example 9. Control represents normal mice ("control"); CD4 mAB represents CD4$^+$ cell depleted mice; IL-12 represents IL-12 treated mice and IFN-$\gamma$ represent IFN-$\gamma$ treated mice.
Figure 11B:
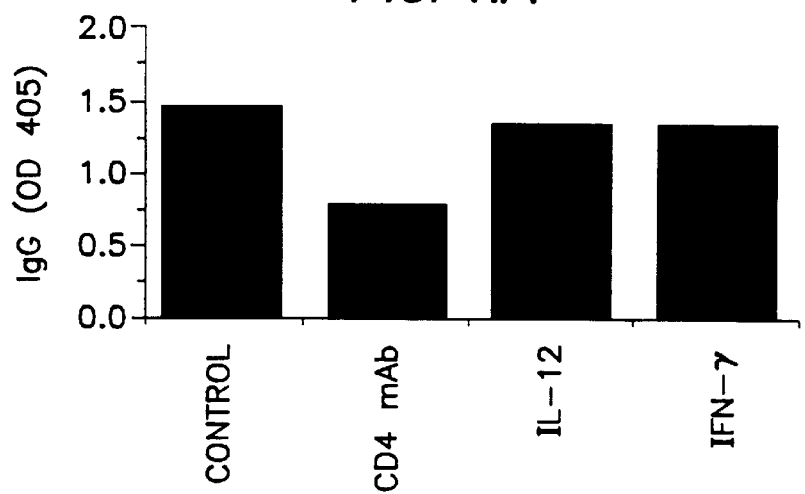
FIG. 11B is a graph summarizing the relative amounts (OD$_{405}$) of IgG present in BAL samples. The symbols are as described in FIG. 11A.
Figure 11C:
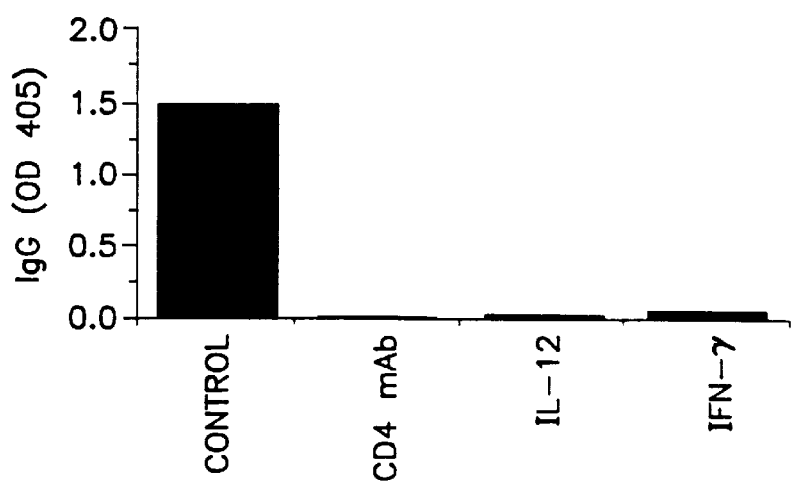
FIG. 11C is a graph summarizing the relative amounts (OD$_{405}$) of IgA present in BAL samples. The symbols are as described in FIG. 11A.

The results are shown graphically in FIGS. 11A through 11C, which summarize neutralizing antibody titer, and the relative amounts ($OD_{405}$) of IgG and IgA present in BAL samples. The titer of neutralizing antibody for each sample was reported as the highest dilution with which less than 50% of cells stained blue.

As demonstrated in the first bar of FIGS. 11A through 11C, the cytokines identified in Table 1 above were associated in the control mice with the appearance of antibodies to adenovirus proteins in BAL of both the IgG and IgA isotypes that were capable of neutralizing the human Ad5 recombinant vector in an in vitro assay out to a 1:800 dilution.

As shown in the second bar of the graphs of FIGS. 11A through 11C, transient $CD4^+$ cell depletion inhibited the formation of neutralizing antibody (FIG. 11A) and virus specific IgA antibody (FIG. 11C) by 80-fold, thereby allowing efficient gene transfer to occur following a second administration of virus. FIG. 11B shows a slight inhibition of IgG as well.

More importantly, as shown in the third bar of the three graphs, IL-12 selectively blocked secretion of antigen specific IgA (FIG. 11C), without significantly impacting on formation of IgG (FIG. 11B). This was concurrent with a 32-fold reduction in neutralizing antibody (FIG. 11A).

The gamma-interferon treated animals (fourth bar of FIGS. 11A through 11B) were virtually indistinguishable from the animals treated with IL-12 in that virus specific IgA (FIG. 11C) and neutralizing antibody (FIG. 11A) were decreased as compared to the control animals not treated with cytokine, but not to the extent obtained with those treated with IL-12.

These studies demonstrate that inhibition, of $CD4^+$ function at the time of primary exposure to virus is sufficient to prevent the formation of blocking antibodies. The concordant reduction of neutralizing antibody with antiviral IgA suggests that immunoglobulin of the IgA subtype is primarily responsible for the blockade to gene transfer.

All references recited above are incorporated herein by reference. Numerous modifications and variations of the present invention are included in the above-identified specification and are expected to be obvious to one of skill in the art. Such modifications and alterations to the compositions and processes of the present invention, such as selections of different modifications of adenovirus vectors selected to carry the VLDLR gene, or selection or dosage of the vectors or immune modulators are believed to be within the scope of the claims appended hereto.

---

What is claimed is:

1. A method for decreasing the level of plasma cholesterol of a human patient, comprising administering in vivo to said patient a composition comprising: a pharmaceutically acceptable carrier and a recombinant adeno-associated viral vector comprising a nucleic acid sequence encoding a human VLDL receptor, said sequence operatively linked to regulatory sequences directing expression of the human VLDL receptor in the hepatocytes of said patient, wherein said recombinant adeno-associated viral vector is present in an amount effective to lower plasma cholesterol levels in said patient.

2. The method according to claim 1 wherein the human VLDL receptor has the sequence of SEQ ID NO:2.

3. The method according to claim 1 wherein the nucleic acid sequence encoding the human VLDL receptor has the sequence of SEQ ID NO:1.

4. The method according to claim 1 wherein the patient has familial hypercholesterolemia or familial combined hyperlipidemia.

* * * * *

UNITED STATES PATENT AND TRADEMARK OFFICE
CERTIFICATE OF CORRECTION

PATENT NO. : 6,174,527 B1  
DATED : January 16, 2001  
INVENTOR(S) : James M. Wilson Page 1 of 1

It is certified that error appears in the above-identified patent and that said Letters Patent is hereby corrected as shown below:

<u>Title page,</u>  
Item [57] Abstract, replace "usefuil" with -- useful --.

<u>Column 14,</u>  
Line 40, replace "completed" with -- complexed --.

<u>Column 15,</u>  
Line 47, replace "IgG2A" with -- $IgG_{2A}$ --.

<u>Column 16,</u>  
Line 57, replace "TH" with -- $T_H$ --.

<u>Column 17,</u>  
Line 48, replace "TE" with -- $T_{H2}$ --.

<u>Column 22,</u>  
Line 36, replace " (FIG. 1C) with -- (FIG. 7C) --

<u>Column 23,</u>  
Line 58, Example 6, replace "faster than n lacz infused mice," with -- faster than in lacz infused mice, --.

<u>Column 26,</u>  
Line 3, replace "developing" with -- developed --.  
Line 4, replace "that" with -- than --.

Signed and Sealed this

Sixteenth Day of October, 2001

Attest:

*Attesting Officer*

NICHOLAS P. GODICI  
*Acting Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 3656 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 392..3010

(xi) SEQUENCE DESCRIPTION: SEQ ID NO:1:

```
CTCTGCGGGC CGCGGGTGCG GGTCGTCGCT ACCGGCTCTC TCCGTTCTGT GCTCTCTTCT      60

GCTCTCGGCT CCCCACCCCC TCTCCCTTCC CTCCTCTCCC CTTGCCTCCC CTCCTCTGCA     120

GCGCCTGCAT TATTTTCTGC CCGCAGCTCG GCTTGCACTG CTGCTGCAGC CCGGGGAGGT     180

GGCTGGGTGG GTGGGGAGGA GACTGTGCAA GTTGTAGGGG AGGGGGTGCC CTCTTCTTCC     240

CCGCTCCCTT CCCCAGCCAA GTGGTTCCCC TCCTTCTCCC CCTTTCCCCT CCCAGCCCCC     300

ACCTTCTTCC TCTTTCGGAA GGGCTGGTAA CTTGTCGTGC GGAGCGAACG GCGGCGGCGG     360

CGGCGGCGGC GGCACCATCC AGGCGGGCAC C ATG GGC ACG TCC GCG CTC TGG        412
                                  Met Gly Thr Ser Ala Leu Trp
                                   1               5

GCC GTC TGG CTG CTG CTC GCG CTG TGC TGG GCG CCC CGG GAG AGC GGC       460
Ala Val Trp Leu Leu Leu Ala Leu Cys Trp Ala Pro Arg Glu Ser Gly
         10                  15                  20

GCC ACC GGA ACC GGG AGA AAA GCC AAA TGT GAA CCC TCC CAA TTC CAG       508
Ala Thr Gly Thr Gly Arg Lys Ala Lys Cys Glu Pro Ser Gln Phe Gln
     25                  30                  35
```

-continued

```
TGC ACA AAT GGT CGC TGT ATT ACG CTG TTG TGG AAA TGT GAT GGG GAT        556
Cys Thr Asn Gly Arg Cys Ile Thr Leu Leu Trp Lys Cys Asp Gly Asp
 40                  45                  50                  55

GAA GAC TGT GTT GAC GGC AGT GAT GAA AAG AAC TGT GTA AAG AAG ACG        604
Glu Asp Cys Val Asp Gly Ser Asp Glu Lys Asn Cys Val Lys Lys Thr
                 60                  65                  70

TGT GCT GAA TCT GAC TTC GTG TGC AAC AAT GGC CAG TGT GTT CCC AGC        652
Cys Ala Glu Ser Asp Phe Val Cys Asn Asn Gly Gln Cys Val Pro Ser
             75                  80                  85

CGA TGG AAG TGT GAT GGA GAT CCT GAC TGC GAA GAT GGT TCA GAT GAA        700
Arg Trp Lys Cys Asp Gly Asp Pro Asp Cys Glu Asp Gly Ser Asp Glu
         90                  95                 100

AGC CCA GAA CAG TGC CAT ATG AGA ACA TGC CGC ATA CAT GAA ATC AGC        748
Ser Pro Glu Gln Cys His Met Arg Thr Cys Arg Ile His Glu Ile Ser
    105                 110                 115

TGT GGC GCC CAT TCT ACT CAG TGT ATC CCA GTG TCC TGG AGA TGT GAT        796
Cys Gly Ala His Ser Thr Gln Cys Ile Pro Val Ser Trp Arg Cys Asp
120                 125                 130                 135

GGT GAA AAT GAT TGT GAC AGT GGA GAA GAT GAA GAA AAC TGT GGC AAT        844
Gly Glu Asn Asp Cys Asp Ser Gly Glu Asp Glu Glu Asn Cys Gly Asn
                140                 145                 150

ATA ACA TGT AGT CCC GAC GAG TTC ACC TGC TCC AGT GGC CGC TGC ATC        892
Ile Thr Cys Ser Pro Asp Glu Phe Thr Cys Ser Ser Gly Arg Cys Ile
            155                 160                 165

TCC AGG AAC TTT GTA TGC AAT GGC CAG GAT GAC TGC AGC GAT GGC AGT        940
Ser Arg Asn Phe Val Cys Asn Gly Gln Asp Asp Cys Ser Asp Gly Ser
        170                 175                 180

GAT GAG CTG GAC TGT GCC CCG CCA ACC TGT GGC GCC CAT GAG TTC CAG        988
Asp Glu Leu Asp Cys Ala Pro Pro Thr Cys Gly Ala His Glu Phe Gln
    185                 190                 195

TGC AGC ACC TCC TCC TGC ATC CCC ATC AGC TGG GTA TGC GAC GAT GAT       1036
Cys Ser Thr Ser Ser Cys Ile Pro Ile Ser Trp Val Cys Asp Asp Asp
200                 205                 210                 215

GCA GAC TGC TCC GAC CAA TCT GAT GAG TCC CTG GAG CAG TGT GGC CGT       1084
Ala Asp Cys Ser Asp Gln Ser Asp Glu Ser Leu Glu Gln Cys Gly Arg
                220                 225                 230

CAG CCA GTC ATA CAC ACC AAG TGT CCA GCC AGC GAA ATC CAG TGC GGC       1132
Gln Pro Val Ile His Thr Lys Cys Pro Ala Ser Glu Ile Gln Cys Gly
            235                 240                 245

TCT GGC GAG TGC ATC CAT AAG AAG TGG CGA TGT GAT GGG GAC CCT GAC       1180
Ser Gly Glu Cys Ile His Lys Lys Trp Arg Cys Asp Gly Asp Pro Asp
        250                 255                 260

TGC AAG GAT GGC AGT GAT GAG GTC AAC TGT CCC TCT CGA ACT TGC CGA       1228
Cys Lys Asp Gly Ser Asp Glu Val Asn Cys Pro Ser Arg Thr Cys Arg
    265                 270                 275

CCT GAC CAA TTT GAA TGT GAG GAT GGC AGC TGC ATC CAT GGC AGC AGG       1276
Pro Asp Gln Phe Glu Cys Glu Asp Gly Ser Cys Ile His Gly Ser Arg
280                 285                 290                 295

CAG TGT AAT GGT ATC CGA GAC TGT GTC GAT GGT TCC GAT GAA GTC AAC       1324
Gln Cys Asn Gly Ile Arg Asp Cys Val Asp Gly Ser Asp Glu Val Asn
                300                 305                 310

TGC AAA AAT GTC AAT CAG TGC TTG GGC CCT GGA AAA TTC AAG TGC AGA       1372
Cys Lys Asn Val Asn Gln Cys Leu Gly Pro Gly Lys Phe Lys Cys Arg
            315                 320                 325

AGT GGA GAA TGC ATA GAT ATC AGC AAA GTA TGT AAC CAG GAG CAG GAC       1420
Ser Gly Glu Cys Ile Asp Ile Ser Lys Val Cys Asn Gln Glu Gln Asp
        330                 335                 340

TGC AGG GAC TGG AGT GAT GAG CCC CTG AAA GAG TGT CAT ATA AAC GAA       1468
Cys Arg Asp Trp Ser Asp Glu Pro Leu Lys Glu Cys His Ile Asn Glu
    345                 350                 355
```

```
TGC TTG GTA AAT AAT GGT GGA TGT TCT CAT ATC TGC AAA GAC CTA GTT         1516
Cys Leu Val Asn Asn Gly Gly Cys Ser His Ile Cys Lys Asp Leu Val
360                 365                 370                 375

ATA GGC TAC GAG TGT GAC TGT GCA GCT GGG TTT GAA CTG ATA GAT AGG         1564
Ile Gly Tyr Glu Cys Asp Cys Ala Ala Gly Phe Glu Leu Ile Asp Arg
                380                 385                 390

AAA ACC TGT GGA GAT ATT GAT GAA TGC CAA AAT CCA GGA ATC TGC AGT         1612
Lys Thr Cys Gly Asp Ile Asp Glu Cys Gln Asn Pro Gly Ile Cys Ser
            395                 400                 405

CAA ATT TGT ATC AAC TTA AAA GGC GGT TAC AAG TGT GAA TGT AGT CGT         1660
Gln Ile Cys Ile Asn Leu Lys Gly Gly Tyr Lys Cys Glu Cys Ser Arg
        410                 415                 420

GCC TAT CAA ATG GAT CTT GCT ACT GGC GTG TGC AAG GCA GTA GGC AAA         1708
Ala Tyr Gln Met Asp Leu Ala Thr Gly Val Cys Lys Ala Val Gly Lys
    425                 430                 435

GAG CCA AGT CTG ATC TTC ACT AAT CGA AGA GAC ATC AGG AAG ATT GGC         1756
Glu Pro Ser Leu Ile Phe Thr Asn Arg Arg Asp Ile Arg Lys Ile Gly
440                 445                 450                 455

TTA GAG AGG AAA GAA TAT ATC CAA CTA GTT GAA CAG CTA AGA AAC ACT         1804
Leu Glu Arg Lys Glu Tyr Ile Gln Leu Val Glu Gln Leu Arg Asn Thr
                460                 465                 470

GTG GCT CTC GAT GCT GAC ATT GCT GCC CAG AAA CTA TTC TGG GCC GAT         1852
Val Ala Leu Asp Ala Asp Ile Ala Ala Gln Lys Leu Phe Trp Ala Asp
            475                 480                 485

CTA AGC CAA AAG GCT ATC TTC AGT GCC TCA ATT GAT GAC AAG GTT GGT         1900
Leu Ser Gln Lys Ala Ile Phe Ser Ala Ser Ile Asp Asp Lys Val Gly
        490                 495                 500

AGA CAT GTT AAA ATG ATC GAC AAT GTC TAT AAT CCT GCA GCC ATT GCT         1948
Arg His Val Lys Met Ile Asp Asn Val Tyr Asn Pro Ala Ala Ile Ala
    505                 510                 515

GTT GAT TGG GTG TAC AAG ACC ATC TAC TGG ACT GAT GCG GCT TCT AAG         1996
Val Asp Trp Val Tyr Lys Thr Ile Tyr Trp Thr Asp Ala Ala Ser Lys
520                 525                 530                 535

ACT ATT TCA GTA GCT ACC CTA GAT GGA ACC AAG AGG AAG TTC CTG TTT         2044
Thr Ile Ser Val Ala Thr Leu Asp Gly Thr Lys Arg Lys Phe Leu Phe
                540                 545                 550

AAC TCT GAC TTG CGA GAG CCT GCC TCC ATA GCT GTG GAC CCA CTG TCT         2092
Asn Ser Asp Leu Arg Glu Pro Ala Ser Ile Ala Val Asp Pro Leu Ser
            555                 560                 565

GGC TTT GTT TAC TGG TCA GAC TGG GGT GAA CCA GCT AAA ATA GAA AAA         2140
Gly Phe Val Tyr Trp Ser Asp Trp Gly Glu Pro Ala Lys Ile Glu Lys
        570                 575                 580

GCA GGA ATG AAT GGA TTC GAT AGA CGT CCA CTG GTG ACA GCG GAT ATC         2188
Ala Gly Met Asn Gly Phe Asp Arg Arg Pro Leu Val Thr Ala Asp Ile
    585                 590                 595

CAG TGG CCT AAC GGA ATT ACA CTT GAC CTT ATA AAA AGT CGC CTC TAT         2236
Gln Trp Pro Asn Gly Ile Thr Leu Asp Leu Ile Lys Ser Arg Leu Tyr
600                 605                 610                 615

TGG CTT GAT TCT AAG TTG CAC ATG TTA TCC AGC GTG GAC TTG AAT GGC         2284
Trp Leu Asp Ser Lys Leu His Met Leu Ser Ser Val Asp Leu Asn Gly
                620                 625                 630

CAA GAT CGT AGG ATA GTA CTA AAG TCT CTG GAG TTC CTA GCT CAT CCT         2332
Gln Asp Arg Arg Ile Val Leu Lys Ser Leu Glu Phe Leu Ala His Pro
            635                 640                 645

CTT GCA CTA ACA ATA TTT GAG GAT CGT GTC TAC TGG ATA GAT GGG GAA         2380
Leu Ala Leu Thr Ile Phe Glu Asp Arg Val Tyr Trp Ile Asp Gly Glu
        650                 655                 660

AAT GAA GCA GTC TAT GGT GCC AAT AAA TTC ACT GGA TCA GAG CAT GCC         2428
Asn Glu Ala Val Tyr Gly Ala Asn Lys Phe Thr Gly Ser Glu His Ala
```

```
                665                 670                 675
ACT CTA GTC AAC AAC CTG AAT GAT GCC CAA GAC ATC ATT GTC TAT CAT        2476
Thr Leu Val Asn Asn Leu Asn Asp Ala Gln Asp Ile Ile Val Tyr His
680                 685                 690                 695

GAA CTT GTA CAG CCA TCA GGT AAA AAT TGG TGT GAA GAA GAC ATG GAG        2524
Glu Leu Val Gln Pro Ser Gly Lys Asn Trp Cys Glu Glu Asp Met Glu
                    700                 705                 710

AAT GGA GGA TGT GAA TAC CTA TGC CTG CCA GCA CCA CAG ATT AAT GAT        2572
Asn Gly Gly Cys Glu Tyr Leu Cys Leu Pro Ala Pro Gln Ile Asn Asp
                715                 720                 725

CAC TCT CCA AAA TAT ACC TGT TCC TGT CCC AGT GGG TAC AAT GTA GAG        2620
His Ser Pro Lys Tyr Thr Cys Ser Cys Pro Ser Gly Tyr Asn Val Glu
            730                 735                 740

GAA AAT GGC CGA GAC TGT CAA AGT ACT GCA ACT ACT GTG ACT TAC AGT        2668
Glu Asn Gly Arg Asp Cys Gln Ser Thr Ala Thr Thr Val Thr Tyr Ser
        745                 750                 755

GAG ACA AAA GAT ACG AAC ACA ACA GAA ATT TCA GCA ACT AGT GGA CTA        2716
Glu Thr Lys Asp Thr Asn Thr Thr Glu Ile Ser Ala Thr Ser Gly Leu
760                 765                 770                 775

GTT CCT GGA GGG ATC AAT GTG ACC ACA GCA GTA TCA GAG GTC AGT GTT        2764
Val Pro Gly Gly Ile Asn Val Thr Thr Ala Val Ser Glu Val Ser Val
                    780                 785                 790

CCC CCA AAA GGG ACT TCT GCC GCA TGG GCC ATT CTT CCT CTC TTG CTC        2812
Pro Pro Lys Gly Thr Ser Ala Ala Trp Ala Ile Leu Pro Leu Leu Leu
                795                 800                 805

TTA GTG ATG GCA GCA GTA GGT GGC TAC TTG ATG TGG CGG AAT TGG CAA        2860
Leu Val Met Ala Ala Val Gly Gly Tyr Leu Met Trp Arg Asn Trp Gln
            810                 815                 820

CAC AAG AAC ATG AAA AGC ATG AAC TTT GAC AAT CCT GTG TAC TTG AAA        2908
His Lys Asn Met Lys Ser Met Asn Phe Asp Asn Pro Val Tyr Leu Lys
        825                 830                 835

ACC ACT GAA GAG GAC CTC TCC ATA GAC ATT GGT AGA CAC AGT GCT TCT        2956
Thr Thr Glu Glu Asp Leu Ser Ile Asp Ile Gly Arg His Ser Ala Ser
840                 845                 850                 855

GTT GGA CAC ACG TAC CCA GCA ATA TCA GTT GTA AGC ACA GAT GAT GAT        3004
Val Gly His Thr Tyr Pro Ala Ile Ser Val Val Ser Thr Asp Asp Asp
                    860                 865                 870

CTA GCT TGACTTCTGT GACAAATGTT GACCTTTGAG GTCTAAACAA ATAATACCCC        3060
Leu Ala

CGTCGGAATG GTAACCGAGC CAGCAGCTGA AGTCTCTTTT TCTTCCTCTC GGCTGGAAGA        3120

ACATCAAGAT ACCTTTGCGT GGATCAAGCT TGCTGTACTT GACCGTTTTT ATATTACTTT        3180

TGTAAATATT CTTGTCCACA TTCTACTTCA GCTTTGGATG TGGTTACCGA GTATCTGTAA        3240

CCCTTGAATT TCTAGACAGT ATTGCCACCT CTGGCCAAAT ATGCACTTTC CCTAGAAAGC        3300

CATATTCCAG CAGTGAAACT TGTGCTATAG TGTATACCAC CTGTACATAC ATTGTATAGG        3360

CCATCTGTAA ATATCCCAGA GAACAATCAC TATTCTTAAG CACTTTGAAA ATATTTCTAT        3420

GTAAATTATT GTAAACTTTT TCAATGGTTG GGACAATGGC AATAGGACAA AACGGGTTAC        3480

TAAGATGAAA TTGCCAAAAA AATTTATAAA CTAATTTTGG TACGTATGAA TGATATCTTT        3540

GACCTCAATG GAGGTTTGCA AAGACTGAGT GTTCAAACTA CTGTACATTT TTTTTCAAGT        3600

GCTAAAAAAT TAAACCAAGC AGCTTAAAAA AAAAAAAAA AAAAAAAAAA AAAAAA            3656

(2) INFORMATION FOR SEQ ID NO:2:

(i) SEQUENCE CHARACTERISTICS:
        (A) LENGTH: 873 amino acids
        (B) TYPE: amino acid
```

(D) TOPOLOGY: linear (ii) MOLECULE TYPE: protein (xi) SEQUENCE DESCRIPTION: SEQ ID NO:2:

```
Met Gly Thr Ser Ala Leu Trp Ala Val Trp Leu Leu Leu Ala Leu Cys
 1               5                  10                  15
Trp Ala Pro Arg Glu Ser Gly Ala Thr Gly Thr Gly Arg Lys Ala Lys
            20                  25                  30
Cys Glu Pro Ser Gln Phe Gln Cys Thr Asn Gly Arg Cys Ile Thr Leu
            35                  40                  45
Leu Trp Lys Cys Asp Gly Asp Glu Asp Cys Val Asp Gly Ser Asp Glu
    50                  55                  60
Lys Asn Cys Val Lys Lys Thr Cys Ala Glu Ser Asp Phe Val Cys Asn
65                  70                  75                  80
Asn Gly Gln Cys Val Pro Ser Arg Trp Lys Cys Asp Gly Asp Pro Asp
                85                  90                  95
Cys Glu Asp Gly Ser Asp Glu Ser Pro Glu Gln Cys His Met Arg Thr
                100                 105                 110
Cys Arg Ile His Glu Ile Ser Cys Gly Ala His Ser Thr Gln Cys Ile
            115                 120                 125
Pro Val Ser Trp Arg Cys Asp Gly Glu Asn Asp Cys Asp Ser Gly Glu
    130                 135                 140
Asp Glu Glu Asn Cys Gly Asn Ile Thr Cys Ser Pro Asp Glu Phe Thr
145                 150                 155                 160
Cys Ser Ser Gly Arg Cys Ile Ser Arg Asn Phe Val Cys Asn Gly Gln
                165                 170                 175
Asp Asp Cys Ser Asp Gly Ser Asp Glu Leu Asp Cys Ala Pro Pro Thr
                180                 185                 190
Cys Gly Ala His Glu Phe Gln Cys Ser Thr Ser Ser Cys Ile Pro Ile
            195                 200                 205
Ser Trp Val Cys Asp Asp Asp Ala Asp Cys Ser Asp Gln Ser Asp Glu
    210                 215                 220
Ser Leu Glu Gln Cys Gly Arg Gln Pro Val Ile His Thr Lys Cys Pro
225                 230                 235                 240
Ala Ser Glu Ile Gln Cys Gly Ser Gly Glu Cys Ile His Lys Lys Trp
                245                 250                 255
Arg Cys Asp Gly Asp Pro Asp Cys Lys Asp Gly Ser Asp Glu Val Asn
                260                 265                 270
Cys Pro Ser Arg Thr Cys Arg Pro Asp Gln Phe Glu Cys Glu Asp Gly
            275                 280                 285
Ser Cys Ile His Gly Ser Arg Gln Cys Asn Gly Ile Arg Asp Cys Val
    290                 295                 300
Asp Gly Ser Asp Glu Val Asn Cys Lys Asn Val Asn Gln Cys Leu Gly
305                 310                 315                 320
Pro Gly Lys Phe Lys Cys Arg Ser Gly Glu Cys Ile Asp Ile Ser Lys
                325                 330                 335
Val Cys Asn Gln Glu Gln Asp Cys Arg Asp Trp Ser Asp Glu Pro Leu
                340                 345                 350
Lys Glu Cys His Ile Asn Glu Cys Leu Val Asn Asn Gly Gly Cys Ser
            355                 360                 365
His Ile Cys Lys Asp Leu Val Ile Gly Tyr Glu Cys Asp Cys Ala Ala
    370                 375                 380
Gly Phe Glu Leu Ile Asp Arg Lys Thr Cys Gly Asp Ile Asp Glu Cys
```

-continued

```
385                 390                 395                 400

Gln Asn Pro Gly Ile Cys Ser Gln Ile Cys Ile Asn Leu Lys Gly Gly
                405                 410                 415

Tyr Lys Cys Glu Cys Ser Arg Ala Tyr Gln Met Asp Leu Ala Thr Gly
                420                 425                 430

Val Cys Lys Ala Val Gly Lys Glu Pro Ser Leu Ile Phe Thr Asn Arg
                435                 440                 445

Arg Asp Ile Arg Lys Ile Gly Leu Glu Arg Lys Glu Tyr Ile Gln Leu
        450                 455                 460

Val Glu Gln Leu Arg Asn Thr Val Ala Leu Asp Ala Asp Ile Ala Ala
465                 470                 475                 480

Gln Lys Leu Phe Trp Ala Asp Leu Ser Gln Lys Ala Ile Phe Ser Ala
                485                 490                 495

Ser Ile Asp Asp Lys Val Gly Arg His Val Lys Met Ile Asp Asn Val
                500                 505                 510

Tyr Asn Pro Ala Ala Ile Ala Val Asp Trp Val Tyr Lys Thr Ile Tyr
            515                 520                 525

Trp Thr Asp Ala Ala Ser Lys Thr Ile Ser Val Ala Thr Leu Asp Gly
    530                 535                 540

Thr Lys Arg Lys Phe Leu Phe Asn Ser Asp Leu Arg Glu Pro Ala Ser
545                 550                 555                 560

Ile Ala Val Asp Pro Leu Ser Gly Phe Val Tyr Trp Ser Asp Trp Gly
                565                 570                 575

Glu Pro Ala Lys Ile Glu Lys Ala Gly Met Asn Gly Phe Asp Arg Arg
                580                 585                 590

Pro Leu Val Thr Ala Asp Ile Gln Trp Pro Asn Gly Ile Thr Leu Asp
            595                 600                 605

Leu Ile Lys Ser Arg Leu Tyr Trp Leu Asp Ser Lys Leu His Met Leu
    610                 615                 620

Ser Ser Val Asp Leu Asn Gly Gln Asp Arg Arg Ile Val Leu Lys Ser
625                 630                 635                 640

Leu Glu Phe Leu Ala His Pro Leu Ala Leu Thr Ile Phe Glu Asp Arg
                645                 650                 655

Val Tyr Trp Ile Asp Gly Glu Asn Glu Ala Val Tyr Gly Ala Asn Lys
            660                 665                 670

Phe Thr Gly Ser Glu His Ala Thr Leu Val Asn Asn Leu Asn Asp Ala
    675                 680                 685

Gln Asp Ile Ile Val Tyr His Glu Leu Val Gln Pro Ser Gly Lys Asn
    690                 695                 700

Trp Cys Glu Glu Asp Met Glu Asn Gly Gly Cys Glu Tyr Leu Cys Leu
705                 710                 715                 720

Pro Ala Pro Gln Ile Asn Asp His Ser Pro Lys Tyr Thr Cys Ser Cys
                725                 730                 735

Pro Ser Gly Tyr Asn Val Glu Glu Asn Gly Arg Asp Cys Gln Ser Thr
            740                 745                 750

Ala Thr Thr Val Thr Tyr Ser Glu Thr Lys Asp Thr Asn Thr Thr Glu
        755                 760                 765

Ile Ser Ala Thr Ser Gly Leu Val Pro Gly Gly Ile Asn Val Thr Thr
        770                 775                 780

Ala Val Ser Glu Val Ser Val Pro Pro Lys Gly Thr Ser Ala Ala Trp
785                 790                 795                 800

Ala Ile Leu Pro Leu Leu Leu Leu Val Met Ala Ala Val Gly Gly Tyr
                805                 810                 815
```

```
Leu Met Trp Arg Asn Trp Gln His Lys Asn Met Lys Ser Met Asn Phe
        820                 825                 830

Asp Asn Pro Val Tyr Leu Lys Thr Thr Glu Glu Asp Leu Ser Ile Asp
        835                 840                 845

Ile Gly Arg His Ser Ala Ser Val Gly His Thr Tyr Pro Ala Ile Ser
        850                 855                 860

Val Val Ser Thr Asp Asp Asp Leu Ala
865                 870
```

(2) INFORMATION FOR SEQ ID NO:3:

(i) SEQUENCE CHARACTERISTICS:
        (A) LENGTH: 9592 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:3:

```
GAATTCGCTA GCATCATCAA TAATATACCT TATTTTGGAT TGAAGCCAAT ATGATAATGA      60

GGGGGTGGAG TTTGTGACGT GGCGCGGGGC GTGGGAACGG GGCGGGTGAC GTAGTAGTGT     120

GGCGGAAGTG TGATGTTGCA AGTGTGGCGG AACACATGTA AGCGACGGAT GTGGCAAAAG     180

TGACGTTTTT GGTGTGCGCC GGTGTACACA GGAAGTGACA ATTTTCGCGC GGTTTTAGGC     240

GGATGTTGTA GTAAATTTGG GCGTAACCGA GTAAGATTTG GCCATTTTCG CGGGAAAACT     300

GAATAAGAGG AAGTGAAATC TGAATAATTT TGTGTTACTC ATAGCGCGTA ATATTTGTCT     360

AGGGAGATCA GCCTGCAGGT CGTTACATAA CTTACGGTAA ATGGCCCGCC TGGCTGACCG     420

CCCAACGACC CCCGCCCATT GACGTCAATA ATGACGTATG TTCCCATAGT AACGCCAATA     480

GGGACTTTCC ATTGACGTCA ATGGGTGGAG TATTTACGGT AAACTGCCCA CTTGGCAGTA     540

CATCAAGTGT ATCATATGCC AAGTACGCCC CCTATTGACG TCAATGACGG TAAATGGCCC     600

GCCTGGCATT ATGCCCAGTA CATGACCTTA TGGGACTTTC CTACTTGGCA GTACATCTAC     660

GTATTAGTCA TCGCTATTAC CATGGTGATG CGGTTTTGGC AGTACATCAA TGGGCGTGGA     720

TAGCGGTTTG ACTCACGGGG ATTTCCAAGT CTCCACCCCA TTGACGTCAA TGGGAGTTTG     780

TTTTGGCACC AAAATCAACG GGACTTTCCA AAATGTCGTA ACAACTCCGC CCCATTGACG     840

CAAATGGGCG GTAGGCGTGT ACGGTGGGAG GTCTATATAA GCAGAGCTCT CTGGCTAACT     900

AGAGAACCCA CTGCTTAACT GGCTTATCGA AATTAATACG ACTCACTATA GGGAGACCCA     960

AGCTTCTCTG CGGGCCGCGG GTGCGGGTCG TCGCTACCGG CTCTCTCCGT TCTGTGCTCT    1020

CTTCTGCTCT CGGCTCCCCA CCCCCTCTCC CTTCCCTCCT CTCCCCTTGC CTCCCCTCCT    1080

CTGCAGCGCC TGCATTATTT TCTGCCCGCA GCTCGGCTTG CACTGCTGCT GCAGCCCGGG    1140

GAGGTGGCTG GGTGGGTGGG GAGGAGACTG TGCAAGTTGT AGGGGAGGGG GTGCCCTCTT    1200

CTTCCCCGCT CCCTTCCCCA GCCAAGTGGT TCCCCTCCTT CTCCCCCTTT CCCTCCCAG    1260

CCCCCACCTT CTTCCTCTTT CGGAAGGGCT GGTAACTTGT CGTGCGGAGC GAACGGCGGC    1320

GGCGGCGGCG GCGGCGGCAC CATCCAGGCG GGCACCATGG GCACGTCCGC GCTCTGGGCC    1380

GTCTGGCTGC TGCTCGCGCT GTGCTGGGCG CCCCGGGAGA GCGGCGCCAC CGGAACCGGG    1440

AGAAAAGCCA AATGTGAACC CTCCCAATTC CAGTGCACAA ATGGTCGCTG TATTACGCTG    1500

TTGTGGAAAT GTGATGGGGA TGAAGACTGT GTTGACGGCA GTGATGAAAA GAACTGTGTA    1560

AAGAAGACGT GTGCTGAATC TGACTTCGTG TGCAACAATG GCCAGTGTGT TCCCAGCCGA    1620
```

-continued

```
TGGAAGTGTG ATGGAGATCC TGACTGCGAA GATGGTTCAG ATGAAAGCCC AGAACAGTGC    1680

CATATGAGAA CATGCCGCAT ACATGAAATC AGCTGTGGCG CCCATTCTAC TCAGTGTATC    1740

CCAGTGTCCT GGAGATGTGA TGGTGAAAAT GATTGTGACA GTGGAGAAGA TGAAGAAAAC    1800

TGTGGCAATA TAACATGTAG TCCCGACGAG TTCACCTGCT CCAGTGGCCG CTGCATCTCC    1860

AGGAACTTTG TATGCAATGG CCAGGATGAC TGCAGCGATG GCAGTGATGA GCTGGACTGT    1920

GCCCCGCCAA CCTGTGGCGC CCATGAGTTC CAGTGCAGCA CCTCCTCCTG CATCCCCATC    1980

AGCTGGGTAT GCGACGATGA TGCAGACTGC TCCGACCAAT CTGATGAGTC CCTGGAGCAG    2040

TGTGGCCGTC AGCCAGTCAT ACACACCAAG TGTCCAGCCA GCGAAATCCA GTGCGGCTCT    2100

GGCGAGTGCA TCCATAAGAA GTGGCGATGT GATGGGACC CTGACTGCAA GGATGGCAGT     2160

GATGAGGTCA ACTGTCCCTC TCGAACTTGC CGACCTGACC AATTTGAATG TGAGGATGGC    2220

AGCTGCATCC ATGGCAGCAG GCAGTGTAAT GGTATCCGAG ACTGTGTCGA TGGTTCCGAT    2280

GAAGTCAACT GCAAAAATGT CAATCAGTGC TTGGGCCCTG AAAATTCAA GTGCAGAAGT     2340

GGAGAATGCA TAGATATCAG CAAAGTATGT AACCAGGAGC AGGACTGCAG GGACTGGAGT    2400

GATGAGCCCC TGAAAGAGTG TCATATAAAC GAATGCTTGG TAAATAATGG TGGATGTTCT    2460

CATATCTGCA AAGACCTAGT TATAGGCTAC GAGTGTGACT GTGCAGCTGG GTTTGAACTG    2520

ATAGATAGGA AAACCTGTGG AGATATTGAT GAATGCCAAA ATCCAGGAAT CTGCAGTCAA    2580

ATTTGTATCA ACTTAAAAGG CGGTTACAAG TGTGAATGTA GTCGTGCCTA TCAAATGGAT    2640

CTTGCTACTG GCGTGTGCAA GGCAGTAGGC AAAGAGCCAA GTCTGATCTT CACTAATCGA    2700

AGAGACATCA GGAAGATTGG CTTAGAGAGG AAAGAATATA TCCAACTAGT TGAACAGCTA    2760

AGAAACACTG TGGCTCTCGA TGCTGACATT GCTGCCCAGA AACTATTCTG GGCCGATCTA    2820

AGCCAAAAGG CTATCTTCAG TGCCTCAATT GATGACAAGG TTGGTAGACA TGTTAAAATG    2880

ATCGACAATG TCTATAATCC TGCAGCCATT GCTGTTGATT GGGTGTACAA GACCATCTAC    2940

TGGACTGATG CGGCTTCTAA GACTATTTCA GTAGCTACCC TAGATGGAAC CAAGAGGAAG    3000

TTCCTGTTTA ACTCTGACTT GCGAGAGCCT GCCTCCATAG CTGTGGACCC ACTGTCTGGC    3060

TTTGTTTACT GGTCAGACTG GGGTGAACCA GCTAAAATAG AAAAAGCAGG AATGAATGGA    3120

TTCGATAGAC GTCCACTGGT GACAGCGGAT ATCCAGTGGC CTAACGGAAT TACACTTGAC    3180

CTTATAAAAA GTCGCCTCTA TTGGCTTGAT TCTAAGTTGC ACATGTTATC CAGCGTGGAC    3240

TTGAATGGCC AAGATCGTAG GATAGTACTA AAGTCTCTGG AGTTCCTAGC TCATCCTCTT    3300

GCACTAACAA TATTTGAGGA TCGTGTCTAC TGGATAGATG GGAAAATGA AGCAGTCTAT     3360

GGTGCCAATA AATTCACTGG ATCAGAGCAT GCCACTCTAG TCAACAACCT GAATGATGCC    3420

CAAGACATCA TTGTCTATCA TGAACTTGTA CAGCCATCAG GTAAAAATTG GTGTGAAGAA    3480

GACATGGAGA ATGGAGGATG TGAATACCTA TGCCTGCCAG CACCACAGAT TAATGATCAC    3540

TCTCCAAAAT ATACCTGTTC CTGTCCCAGT GGGTACAATG TAGAGGAAAA TGGCCGAGAC    3600

TGTCAAAGTA CTGCAACTAC TGTGACTTAG AGACAAAAGA TACGAACACA ACAGAAATTT    3660

CAGCAACTAG TGGACTAGTT CCTGGAGGGA TCAATGTGAC CACAGCAGTA TCAGAGGTCA    3720

GTGTTCCCCC AAAAGGGACT TCTGCCGCAT GGGCCATTCT TCCTCTCTTG CTCTTAGTGA    3780

TGGCAGCAGT AGGTGGCTAC TTGATGTGGC GGAATTGGCA ACACAAGAAC ATGAAAAGCA    3840

TGAACTTTGA CAATCCTGTG TACTTGAAAA CCACTGAAGA GGACCTCTCC ATAGACATTG    3900

GTAGACACAG TGCTTCTGTT GGACACACGT ACCCAGCAAT ATCAGTTGTA AGCACAGATG    3960
```

```
ATGATCTAGC TTGACTTCTG TGACAAATGT TGACCTTTGA GGTCTAAACA AATAATACCC    4020

CCGTCGGAAT GGTAACCGAG CCAGCAGCTG AAGTCTCTTT TTCTTCCTCT CGGCTGGAAG    4080

AACATCAAGA TACCTTTGCG TGGATCAAGC TTGGTACCGA GCTCGGATCC ACTAGTAACG    4140

GCCGCCAGTG TGCTGGAATT CTGCAGATAT CCATCACACT GGCGGCCGCG GGATCCAGA    4200

CATGATAAGA TACATTGATG AGTTTGGACA AACCACAACT AGAATGCAGT GAAAAAAATG    4260

CTTTATTTGT GAAATTTGTG ATGCTATTGC TTTATTTGTA ACCATTATAA GCTGCAATAA    4320

ACAAGTTAAC AACAACAATT GCATTCATTT TATGTTTCAG GTTCAGGGGG AGGTGTGGGA    4380

GGTTTTTTCG GATCCTCTAG AGTCGACCTG CAGGCTGATC TGGAAGGTGC TGAGGTACGA    4440

TGAGACCCGC ACCAGGTGCA GACCCTGCGA GTGTGGCGGT AAACATATTA GGAACCAGCC    4500

TGTGATGCTG GATGTGACCG AGGAGCTGAG GCCCGATCAC TTGGTGCTGG CCTGCACCCG    4560

CGCTGAGTTT GGCTCTAGCG ATGAAGATAC AGATTGAGGT ACTGAAATGT GTGGGCGTGG    4620

CTTAAGGGTG GGAAAGAATA TATAAGGTGG GGGTCTTATG TAGTTTTGTA TCTGTTTTGC    4680

AGCAGCCGCC GCCGCCATGA GCACCAACTC GTTTGATGGA AGCATTGTGA GCTCATATTT    4740

GACAACGCGC ATGCCCCCAT GGGCCGGGGT GCGTCAGAAT GTGATGGGCT CCAGCATTGA    4800

TGGTCGCCCC GTCCTGCCCG CAAACTCTAC TACCTTGACC TACGAGACCG TGTCTGGAAC    4860

GCCGTTGGAG ACTGCAGCCT CCGCCGCCGC TTCAGCCGCT GCAGCCACCG CCCGCGGGAT    4920

TGTGACTGAC TTTGCTTTCC TGAGCCCGCT TGCAAGCAGT GCAGCTTCCC GTTCATCCGC    4980

CCGCGATGAC AAGTTGACGG CTCTTTTGGC ACAATTGGAT CTTTGACCC GGGAACTTAA     5040

TGTCGTTTCT CAGCAGCTGT TGGATCTGCG CCAGCAGGTT TCTGCCCTGA AGGCTTCCTC    5100

CCCTCCCAAT GCGGTTTAAA ACATAAATAA AAAACCAGAC TCTGTTTGGA TTTGGATCAA    5160

GCAAGTGTCT TGCTGTCTTT ATTTAGGGGT TTTGCGCGCG CGGTAGGCCC GGGACCAGCG    5220

GTCTCGGTCG TTGAGGGTCC TGTGTATTTT TTCCAGGACG TGGTAAAGGT GACTCTGGAT    5280

GTTCAGATAC ATGGGCATAA GCCCGTCTCT GGGGTGGAGG TAGCACCACT GCAGAGCTTC    5340

ATGCTGCGGG GTGGTGTTGT AGATGATCCA GTCGTAGCAG GAGCGCTGGG CGTGGTGCCT    5400

AAAAATGTCT TTCAGTAGCA AGCTGATTGC CAGGGGCAGG CCCTTGGTGT AAGTGTTTAC    5460

AAAGCGGTTA AGCTGGGATG GGTGCATACG TGGGGATATG AGATGCATCT TGGACTGTAT    5520

TTTTAGGTTG GCTATGTTCC CAGCCATATC CCTCCGGGGA TTCATGTTGT GCAGAACCAC    5580

CAGCACAGTG TATCCGGTGC ACTTGGGAAA TTTGTCATGT AGCTTAGAAG GAAATGCGTG    5640

GAAGAACTTG GAGACGCCCT TGTGACCTCC AAGATTTTCC ATGCATTCGT CCATAATGAT    5700

GGCAATGGGC CCACGGGCGG CGGCCTGGGC GAAGATATTT CTGGGATCAC TAACGTCATA    5760

GTTGTGTTCC AGGATGAGAT CGTCATAGGC CATTTTTACA AAGCGCGGGC GGAGGGTGCC    5820

AGACTGCGGT ATAATGGTTC CATCCGGCCC AGGGGCGTAG TTACCCTCAC AGATTTGCAT    5880

TTCCCACGCT TTGAGTTCAG ATGGGGGGAT CATGTCTACC TGCGGGCGA TGAAGAAAAC    5940

GGTTCCGGG GTAGGGGAGA TCAGCTGGGA AGAAAGCAGG TTCCTGAGCA GCTGCGACTT    6000

ACCGCAGCCG GTGGGCCCGT AAATCACACC TATTACCGGG TGCAACTGGT AGTTAAGAGA    6060

GCTGCAGCTG CCGTCATCCC TGAGCAGGGG GGCCACTTCG TTAAGCATGT CCCTGACTCG    6120

CATGTTTTCC CTGACCAAAT CCGCCAGAAG GCGCTCGCCG CCCAGCGATA GCAGTTCTTG    6180

CAAGGAAGCA AAGTTTTTCA ACGGTTTGAG ACCGTCCGCC GTAGGCATGC TTTTGAGCGT    6240

TTGACCAAGC AGTTCCAGGC GGTCCCACAG CTCGGTCACC TGCTCTACGG CATCTCGATC    6300

CAGCATATCT CCTCGTTTCG CGGGTTGGGG CGGCTTTCGC TGTACGGCAG TAGTCGGTGC    6360
```

```
TCGTCCAGAC GGGCCAGGGT CATGTCTTTC CACGGGCGCA GGGTCCTCGT CAGCGTAGTC   6420

TGGGTCACGG TGAAGGGGTG CGCTCCGGGC TGCGCGCTGG CCAGGGTGCG CTTGAGGCTG   6480

GTCCTGCTGG TGCTGAAGCG CTGCCGGTCT TCGCCCTGCG CGTCGGCCAG GTAGCATTTG   6540

ACCATGGTGT CATAGTCCAG CCCCTCCGCG GCGTGGCCCT TGGCGCGCAG CTTGCCCTTG   6600

GAGGAGGCGC CGCACGAGGG GCAGTGCAGA CTTTTGAGGG CGTAGAGCTT GGGCGCGAGA   6660

AATACCGATT CCGGGGAGTA GGCATCCGCG CCGCAGGCCC CGCAGACGGT CTCGCATTCC   6720

ACGAGCCAGG TGAGCTCTGG CCGTTCGGGG TCAAAAACCA GGTTTCCCCC ATGCTTTTTG   6780

ATGCGTTTCT TACCTCTGGT TTCCATGAGC CGGTGTCCAC GCTCGGTGAC GAAAAGGCTG   6840

TCCGTGTCCC CGTATACAGA CTTGAGAGGC CTGTCCTCGA CCGATGCCCT TGAGAGCCTT   6900

CAACCCAGTC AGCTCCTTCC GGTGGGCGCG GGGCATGACT ATCGTCGCCG CACTTATGAC   6960

TGTCTTCTTT ATCATGCAAC TCGTAGGACA GGTGCCGGCA GCGCTCTGGG TCATTTTCGG   7020

CGAGGACCGC TTTCGCTGGA GCGCGACGAT GATCGGCCTG TCGCTTGCGG TATTCGGAAT   7080

CTTGCACGCC CTCGCTCAAG CCTTCGTCAC TGGTCCCGCC ACCAAACGTT TCGGCGAGAA   7140

GCAGGCCATT ATCGCCGGCA TGGCGGCCGA CGCGCTGGGC TACGTCTTGC TGGCGTTCGC   7200

GACGCGAGGC TGGATGGCCT TCCCCATTAT GATTCTTCTC GCTTCCGGCG GCATCGGGAT   7260

GCCCGCGTTG CAGGCCATGC TGTCCAGGCA GGTAGATGAC GACCATCAGG GACAGCTTCA   7320

AGGATCGCTC GCGGCTCTTA CCAGCCTAAC TTCGATCACT GGACCGCTGA TCGTCACGGC   7380

GATTTATGCC GCCTCGGCGA GCACATGGAA CGGGTTGGCA TGGATTGTAG CGCCGCCCT   7440

ATACCTTGTC TGCCTCCCCG CGTTGCGTCG CGGTGCATGG AGCCGGGCCA CCTCGACCTG   7500

AATGGAAGCC GGCGGCACCT CGCTAACGGA TTCACCACTC CAAGAATTGG AGCCAATCAA   7560

TTCTTGCGGA GAACTGTGAA TGCGCAAACC AACCCTTGGC AGAACATATC CATCGCGTCC   7620

GCCATCTCCA GCAGCCGCAC GCGGCGCATC TCGGGCAGCG TTGGGTCCTG GCCACGGGTG   7680

CGCATGATCG TGCTCCTGTC GTTGAGGACC CGGCTAGGCT GGCGGGGTTG CCTTACTGGT   7740

TAGCAGAATG AATCACCGAT ACGCGAGCGA ACGTGAAGCG ACTGCTGCTG CAAAACGTCT   7800

GCGACCTGAG CAACAACATG AATGGTCTTC GGTTTCCGTG TTTCGTAAAG TCTGGAAACG   7860

CGGAAGTCAG CGCCCTGCAC CATTATGTTC CGGATCTGCA TCGCAGGATG CTGCTGGCTA   7920

CCCTGTGGAA CACCTACATC TGTATTAACG AAGCCTTTCT CAATGCTCAC GCTGTAGGTA   7980

TCTCAGTTCG GTGTAGGTCG TTCGCTCCAA GCTGGGCTGT GTGCACGAAC CCCCCGTTCA   8040

GCCCGACCGC TGCGCCTTAT CCGGTAACTA TCGTCTTGAG TCCAACCCGG TAAGACACGA   8100

CTTATCGCCA CTGGCAGCAG CCACTGGTAA CAGGATTAGC AGAGCGAGGT ATGTAGGCGG   8160

TGCTACAGAG TTCTTGAAGT GGTGGCCTAA CTACGGCTAC ACTAGAAGGA CAGTATTTGG   8220

TATCTGCGCT CTGCTGAAGC CAGTTACCTT CGGAAAAAGA GTTGGTAGCT CTTGATCCGG   8280

CAAACAAACC ACCGCTGGTA GCGGTGGTTT TTTTGTTTGC AAGCAGCAGA TTACGCGCAG   8340

AAAAAAAGGA TCTCAAGAAG ATCCTTTGAT CTTTTCTACG GGGTCTGACG CTCAGTGGAA   8400

CGAAAACTCA CGTTAAGGGA TTTTGGTCAT GAGATTATCA AAAAGGATCT TCACCTAGAT   8460

CCTTTTAAAT TAAAAATGAA GTTTTAAATC AATCTAAAGT ATATATGAGT AAACTTGGTC   8520

TGACAGTTAC CAATGCTTAA TCAGTGAGGC ACCTATCTCA GCGATCTGTC TATTTCGTTC   8580

ATCCATAGTT GCCTGACTCC CCGTCGTGTA GATAACTACG ATACGGGAGG GCTTACCATC   8640

TGGCCCCAGT GCTGCAATGA TACCGCGAGA CCCACGCTCA CCGGCTCCAG ATTTATCAGC   8700
```

-continued

```
AATAAACCAG CCAGCCGGAA GGGCCGAGCG CAGAAGTGGT CCTGCAACTT TATCCGCCTC    8760

CATCCAGTCT ATTAATTGTT GCCGGGAAGC TAGAGTAAGT AGTTCGCCAG TTAATAGTTT    8820

GCGCAACGTT GTTGCCATTG CTGCAGGCAT CGTGGTGTCA CGCTCGTCGT TTGGTATGGC    8880

TTCATTCAGC TCCGGTTCCC AACGATCAAG GCGAGTTACA TGATCCCCCA TGTTGTGCAA    8940

AAAAGCGGTT AGCTCCTTCG GTCCTCCGAT CGTTGTCAGA AGTAAGTTGG CCGCAGTGTT    9000

ATCACTCATG GTTATGGCAG CACTGCATAA TTCTCTTACT GTCATGCCAT CCGTAAGATG    9060

CTTTTCTGTG ACTGGTGAGT ACTCAACCAA GTCATTCTGA GAATAGTGTA TGCGGCGACC    9120

GAGTTGCTCT TGCCCGGCGT CAACACGGGA TAATACCGCG CCACATAGCA GAACTTTAAA    9180

AGTGCTCATC ATTGGAAAAC GTTCTTCGGG GCGAAAACTC TCAAGGATCT TACCGCTGTT    9240

GAGATCCAGT TCGATGTAAC CCACTCGTGC ACCCAACTGA TCTTCAGCAT CTTTTACTTT    9300

CACCAGCGTT TCTGGGTGAG CAAAAACAGG AAGGCAAAAT GCCGCAAAAA AGGGAATAAG    9360

GGCGACACGG AAATGTTGAA TACTCATACT CTTCCTTTTT CAATATTATT GAAGCATTTA    9420

TCAGGGTTAT TGTCTCATGA GCGGATACAT ATTTGAATGT ATTTAGAAAA ATAAACAAAT    9480

AGGGGTTCCG CGCACATTTC CCCGAAAAGT GCCACCTGAC GTCTAAGAAA CCATTATTAT    9540

CATGACATTA ACCTATAAAA ATAGGCGTAT CACGAGGCCC TTTCGTCTTC AA            9592
```

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:4:

```
TAGTAAATTT GGGC                                                       14
```

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:5:

```
AGTAAGATTT GGCC                                                       14
```

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:6:

```
AGTGAAATCT GAAT                                                       14
```

(2) INFORMATION FOR SEQ ID NO:7:

(i) SEQUENCE CHARACTERISTICS:

```
        (A) LENGTH: 14 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:7:

GAATAATTTT GTGT                                                              14

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:8:

CGTAATATTT GTCT                                                              14
```